United States Patent
Omura et al.

(10) Patent No.: US 8,133,871 B2
(45) Date of Patent: Mar. 13, 2012

(54) DIHYDROPSEUDOERYTHROMYCIN DERIVATIVES

(75) Inventors: Satoshi Omura, Tokyo (JP); Toshiaki Sunazuka, Funabashi (JP); Kenichiro Nagai, Tokyo (JP); Hideaki Shima, Kobe (JP); Haruko Yamabe, Tokyo (JP)

(73) Assignees: The Kitasato Institute, Tokyo (JP); Aphoenix, Inc., Tokyo (JP)

( * ) Notice: Subject to any disclaimer, the term of this patent is extended or adjusted under 35 U.S.C. 154(b) by 730 days.

(21) Appl. No.: 12/083,484

(22) PCT Filed: Oct. 13, 2006

(86) PCT No.: PCT/JP2006/320888
§ 371 (c)(1),
(2), (4) Date: Jan. 14, 2009

(87) PCT Pub. No.: WO2007/043710
PCT Pub. Date: Apr. 19, 2007

(65) Prior Publication Data
US 2009/0131341 A1 May 21, 2009

(30) Foreign Application Priority Data

Oct. 14, 2005 (JP) ................................. 2005-301070

(51) Int. Cl.
*A61K 31/70* (2006.01)
*C07H 17/08* (2006.01)
(52) U.S. Cl. ............................. 514/28; 536/7.1; 536/7.2
(58) Field of Classification Search .................. 536/7.1, 536/7.2
See application file for complete search history.

(56) References Cited

U.S. PATENT DOCUMENTS

| | | | |
|---|---|---|---|
| 5,106,961 A | 4/1992 | Kirst et al. | |
| 2004/0067896 A1 | 4/2004 | Omura et al. | |
| 2004/0147461 A1 | 7/2004 | Ashley et al. | |
| 2005/0176655 A1 | 8/2005 | Omura et al. | |

FOREIGN PATENT DOCUMENTS

| EP | 1 256 587 A1 | 11/2002 |
|---|---|---|
| WO | 02/051855 A2 | 7/2002 |

OTHER PUBLICATIONS

Supplementary European Search Report dated Jan. 7, 2010 issued in European application corresponding to present US application.
Kibwage I. O. et al., "Translactonization in Erythromycins", Journal of Organic Chemistry, 1987, vol. 52, No. 6, pp. 990-996.
Kibwage I. O. et al., "Identification of Novel Erythromycin Derivatives in Mother Liquor Concentrates of Streptomyces Erythraeus", Journal of Antibiotics, 1987, vol. XL, No. 1, pp. 1-6.
International Search Report issued Nov. 21, 2006 in the International (PCT) Application PCT/JP2006/320888 of which the present application is the U.S. National Stage.
Ramin Faghih et al., "Preparation of 9-Deoxo-4"-Deoxy-6,9-Epoxyerythromycin Lactams "Motilactides": Potent and Orally Active Prokinetic Agents", Bioorganic & Medicinal Chemistry Letters, vol. 8, No. 7, pp. 805-810, 1998.

*Primary Examiner* — Elli Peselev
(74) *Attorney, Agent, or Firm* — Wenderoth, Lind & Ponack, LLP.

(57) ABSTRACT

A compound represented by the formula [I] wherein each symbol is as defined in the specification or a pharmacologically acceptable salt thereof, and a pharmaceutical composition containing the compound as an active ingredient.

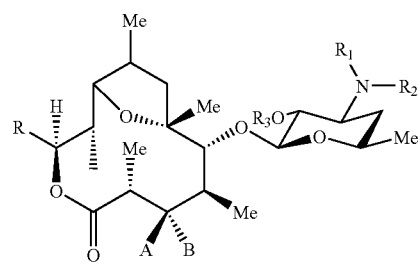

[I]

25 Claims, No Drawings

DIHYDROPSEUDOERYTHROMYCIN DERIVATIVES

TECHNICAL FIELD

The present invention relates to a novel dihydropseudoerythromycin derivative. Particularly, the present invention relates to a novel dihydropseudoerythromycin derivative, which is superior in the anti-inflammatory action and stable.

BACKGROUND ART

Erythromycin (14-membered ring macrolide) is difficult to use as an anti-inflammatory agent since it simultaneously has an anti-inflammatory action and an antibacterial action. To solve this problem, a pseudoerythromycin derivative (12-membered ring, see THE KITASATO INSTITUTE, EM700 series, WO2002/14338 and WO2004/39823) having an anti-inflammatory action but free of an antibacterial action has been reported. A representative compound is EM703 shown by the following formula:

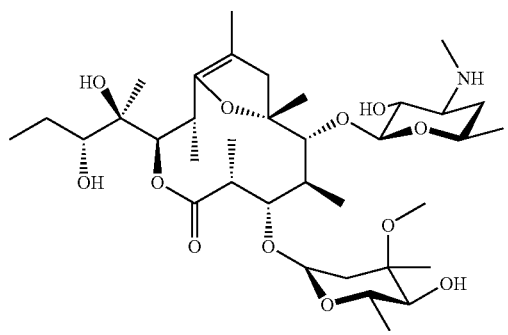

The above-mentioned pseudoerythromycin derivative has a problem in that its pharmacological action may not be sufficiently exhibited by oral administration, since the derivative is partly decomposed by an acid and becomes comparatively unstable.

A dihydro form obtained by reducing to solve the problem is stable to acid and shows good pharmacological action by oral administration. While Faghih R, Nellans H N, Lartey P A, Petersen A, Marsh K, Bennani Y L, Plattner J J. Preparation of 9-deoxo-4"-deoxy-6,9-epoxyerythromycin lactams "motilactides": potent and orally active prokinetic agents. Bioorg Med Chem. Lett. 1998, 8(7):805-10 describes dihydropseudoerythromycin derivatives, all of them are 4"-dehydroxy forms of cladinose (sugar at the 3-position). The document describes that the dihydropseudoerythromycin derivatives show a weak gastrointestinal motility-promoting activity, but does not describe an anti-inflammatory action.

DISCLOSURE OF THE INVENTION

The present invention aims to avoid the antibacterial action of erythromycin and develop a compound having an anti-inflammatory action alone, particularly, to develop a stable pseudoerythromycin derivative.

The present inventors have conducted intensive studies in an attempt to solve the aforementioned problem and succeeded in avoiding the antibacterial action by using a 12-membered ring and further reducing the compound to give a dihydro form, thereby improving the stability to an acid, which resulted in the completion of the present invention. Accordingly, the present invention provides the following.

[1] A compound represented by the following formula [I]

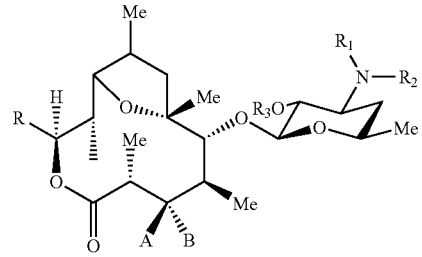

wherein Me is a methyl group, $R_1$ and $R_2$ are the same or different and each is a hydrogen atom, an alkyl group, an acyl group, a sulfonyl group, a substituted or unsubstituted aryl-substituted alkyl group, an aryl-substituted alkyloxycarbonyl group, an alkenyl group or an alkynyl group, or $R_1$ and $R_2$ in combination form, together with the adjacent nitrogen atom, a substituted or unsubstituted alicyclic heterocyclic group, $R_3$ is a hydrogen atom, a substituted or unsubstituted acyl group or an aryl-substituted alkyloxycarbonyl group, A is a hydrogen atom, B is a hydroxyl group or a group represented by the following formula [II]

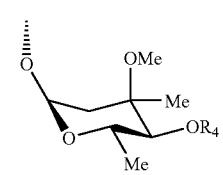

wherein Me is a methyl group and $R_4$ is a hydrogen atom or an acyl group, or A and B in combination show =O, R is a group represented by the following formula [III]

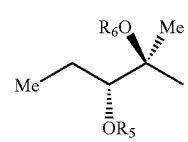

wherein Me is a methyl group, $R_5$ and $R_6$ are the same or different and each is a hydrogen atom or an acyl group, or $R_5$ and $R_6$ in combination show a carbonyl group or a substituted or unsubstituted alkylene group, a substituent represented by the following formula [IV]

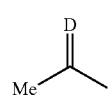

wherein Me is a methyl group, D is O or N—OH, or D is a hydrogen atom and a hydroxyl group (—H, —OH), or a substituent represented by the following formula [V]

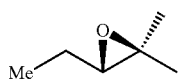

wherein Me is a methyl group,
or a pharmacologically acceptable salt thereof.

[2] The compound of the above-mentioned [1], wherein R is a group represented by the following formula [III]

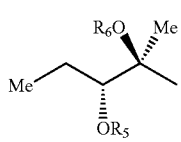

wherein Me is a methyl group, $R_5$ and $R_6$ are the same or different and each is a hydrogen atom or an acyl group, or $R_5$ and $R_6$ in combination show a carbonyl group or a substituted or unsubstituted alkylene group, or a pharmacologically acceptable salt thereof.

[3] The compound of the above-mentioned [1] or [2], wherein A and B in combination show =O, or a pharmacologically acceptable salt thereof.

[4] The compound of the above-mentioned [1] or [2], wherein A is a hydrogen atom and B is a hydroxyl group, or a pharmacologically acceptable salt thereof.

[5] The compound of the above-mentioned [1] or [2], wherein A is a hydrogen atom and B is a group represented by the following formula [II]

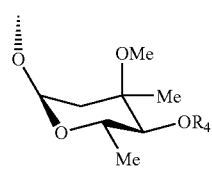

wherein Me is a methyl group and $R_4$ is a hydrogen atom or an acyl group, or a pharmacologically acceptable salt thereof.

[6] The compound of the above-mentioned [5], wherein $R_4$ is a hydrogen atom, or a pharmacologically acceptable salt thereof.

[7] The compound of any one of the above-mentioned [1] to [6], wherein $R_1$ and $R_2$ are the same or different and each is a hydrogen atom, an alkyl group, a substituted or unsubstituted benzyl group or a benzyloxycarbonyl group, or $R_1$ and $R_2$ in combination form, together with the adjacent nitrogen atom, a substituted or unsubstituted alicyclic heterocyclic group, or a pharmacologically acceptable salt thereof.

[8] The compound of the above-mentioned [7], wherein $R_1$ and $R_2$ are the same or different and each is a hydrogen atom, a lower alkyl group having 1 to 3 carbon atoms or a halogen-substituted benzyl group, or a pharmacologically acceptable salt thereof.

[9] The compound of the above-mentioned [7], wherein the substituted or unsubstituted alicyclic heterocyclic group formed by $R_1$ and $R_2$ in combination together with the adjacent nitrogen atom is a substituted or unsubstituted morpholine ring, piperidine ring, piperazine ring or pyrrolidine ring, or a pharmacologically acceptable salt thereof.

[10] The compound of any one of the above-mentioned [1] to [9], wherein $R_3$ is a hydrogen atom, an acetyl group, a substituted or unsubstituted benzoyl group or a benzyloxycarbonyl group, or a pharmacologically acceptable salt thereof.

[11] The compound of the above-mentioned [10], wherein $R_3$ is a hydrogen atom, a substituted or unsubstituted acetyl group or a benzoyl group, or a pharmacologically acceptable salt thereof.

[12] The following compound
(1) 9-dihydro-pseudoerythromycin A 6,9-epoxide
(2) de(3'-N-methyl)-9-dihydro-pseudoerythromycin A 6,9-epoxide
(3) de(3'-N-methyl)-3'-N-benzyl-9-dihydro-pseudoerythromycin A 6,9-epoxide
(4) bis-de(3'-N-methyl)-9-dihydro-pseudoerythromycin A 6,9-epoxide
(5) bis-de(3'-N-methyl)-bis-(3'-N-benzyl)-9-dihydro-pseudoerythromycin A 6,9-epoxide
(6) de(3'-N-methyl)-3'-N-(p-chlorobenzyl)-9-dihydro-pseudoerythromycin A 6,9-epoxide
(7) de[12-(1-hydroxypropyl)]-9-dihydro-12-oxo-pseudoerythromycin A 6,9-epoxide
(8) de[12-(1-hydroxypropyl)]-9-dihydro-12-hydroxyoxime-pseudoerythromycin A 6,9-epoxide
(9) de[12-(1-hydroxypropyl)]-9-dihydro-pseudoerythromycin A 6,9-epoxide
(10) 12,13-epoxy-9-dihydro-pseudoerythromycin A 6,9-epoxide
(11) de(3-O-cladinosyl)-9-dihydro-pseudoerythromycin A 6,9-epoxide
(12) 4'',13-O-diacetyl-9-dihydro-pseudoerythromycin A 6,9-epoxide
(13) 2'-O-acetyl-9-dihydro-pseudoerythromycin A 6,9-epoxide
(14) de(3'-dimethylamino)-3'-morpholino-9-dihydro-pseudoerythromycin A 6,9-epoxide
(15) 2'-O-acetyl-de(3-O-cladinosyl)-9-dihydro-3-keto-pseudoerythromycin A 6,9-epoxide 12,13-carbonate
(16) de(3-O-cladinosyl)-9-dihydro-3-keto-pseudoerythromycin A 6,9-epoxide 12,13-carbonate
(17) de(3'-N-methyl)-3'-N-(p-chlorobenzyl)-de(3-O-cladinosyl)-9-dihydro-pseudoerythromycin A 6,9-epoxide
(18) 2'-O-acetyl-de(3-O-cladinosyl)-9-dihydro-3-keto-de(3'-dimethylamino)-3'-morpholino-pseudoerythromycin A 6,9-epoxide 12,13-carbonate
(19) de(3-O-cladinosyl)-9-dihydro-3-keto-de(3'-dimethylamino)-3'-morpholino-pseudoerythromycin A 6,9-epoxide 12,13-carbonate
(20) de(3'-N-methyl)-2'-O-3'-N-bis(benzyloxycarbonyl)-de(3-O-cladinosyl)-9-dihydro-pseudoerythromycin A 6,9-epoxide 12,13-carbonate
(21) de(3'-N-methyl)-3'-N-(p-chlorobenzyl)-de(3-O-cladinosyl)-9-dihydro-3-keto-pseudoerythromycin A 6,9-epoxide 12,13-carbonate
(22) de(3-O-cladinosyl)-9-dihydro-de(3'-dimethylamino)-3'-morpholino-pseudoerythromycin A 6,9-epoxide 12,13-carbonate
(23) de(3'-N-methyl)-3'-N-(p-chlorobenzyl)-de(3-O-cladinosyl)-9-dihydro-3-keto-pseudoerythromycin A 6,9-epoxide 12,13-isopropylidene acetal or
(24) de(3'-N-methyl)-3'-N-(p-chlorobenzyl)-de(3-O-cladinosyl)-9-dihydro-3-keto-pseudoerythromycin A 6,9-epoxide, or a pharmacologically acceptable salt thereof.

[13] The following compound
(1) de(3'-N-methyl)-3'-N-(p-chlorobenzyl)-9-dihydro-pseudoerythromycin A 6,9-epoxide (2) de(3'-dimethylamino)-3'-morpholino-9-dihydro-pseudoerythromycin A 6,9-epoxide or
(3) de(3'-N-methyl)-3'-N-(p-chlorobenzyl)-de(3-O-cladinosyl)-9-dihydro-3-keto-pseudoerythromycin A 6,9-epoxide 12,13-carbonate,
or a pharmacologically acceptable salt thereof.
[14] A pharmaceutical composition comprising a compound of any one of the above-mentioned [1] to [13] or a pharmacologically acceptable salt thereof as an active ingredient.
[15] The pharmaceutical composition of the above-mentioned [14], which is used for the prophylaxis or treatment of an inflammatory disease.
[16] The pharmaceutical composition of the above-mentioned [15], wherein the inflammatory disease is an inflammatory bowel disease.
[17] A method for the prophylaxis or treatment of an inflammatory disease, which comprises administering an effective amount of a compound of any one of the above-mentioned [1] to [13] or a pharmacologically acceptable salt thereof to a patient in need thereof.
[18] The method of the above-mentioned [17], wherein the inflammatory disease is an inflammatory bowel disease.
[19] Use of a compound of any one of the above-mentioned [1] to [13] or a pharmacologically acceptable salt thereof for the production of a pharmaceutical agent for the prophylaxis or treatment of an inflammatory disease.
[20] The use of the above-mentioned [19], wherein the inflammatory disease is an inflammatory bowel disease.
[21] A commercial package comprising an agent for the prophylaxis or treatment of an inflammatory disease, which comprises a compound of any one of the above-mentioned [1] to [13] or a pharmacologically acceptable salt thereof as an active ingredient, and a written matter stating that the agent can or should be used for the prophylaxis or treatment of an inflammatory disease.

DETAILED DESCRIPTION OF THE INVENTION

In the compound represented by the above-mentioned formula [I], the steric structures at the 8-position and 9-position are not particularly limited. The compound of the present invention encompasses all stereoisomers at the 8-position and 9-position.

In the present specification, the "alkyl group" is a straight chain or branched chain alkyl group having 1 to 12 carbon atoms or a cyclic alkyl group having 3 to 10 carbon atoms. Examples thereof include a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an isopropyl group, an isobutyl group, a sec-butyl group, a tert-butyl group, an isopentyl group, a tert-pentyl group, a neopentyl group, a 2-pentyl group, a 3-pentyl group, a 2-hexyl group, a tert-octyl group, a cyclopropyl group, a cyclobutyl group, a cyclopentyl group, a cyclohexyl group, a 1-adamantyl group and the like, with preference given to a lower alkyl group having 1 to 3 carbon atoms (methyl group, ethyl group, n-propyl group etc.).

In the present specification, the "acyl group" is a formyl group, an acyl group having a straight chain or branched chain alkyl group having 1 to 12 carbon atoms or a cyclic alkyl group having 3 to 10 carbon atoms, an acyl group having a straight chain or branched chain alkenyl group having 2 to 12 carbon atoms or a cyclic alkenyl group having 3 to 10 carbon atoms, or an acyl group having an aryl group having 6 to 14 carbon atoms. As used herein, the aryl group is a monocyclic-tricyclic aromatic hydrocarbon group having 6 to 14 carbon atoms. Examples thereof include a phenyl group, a biphenyl group, a naphthyl group, an anthryl group, a phenanthryl group and the like. Examples of the acyl group include a formyl group, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a benzoyl group, a naphthoyl group and the like, with preference given to an acetyl group and a benzoyl group.

In the present specification, the "substituted or unsubstituted acyl group" means an unsubstituted acyl group (as defined above) or a substituted acyl group. Examples of the substituent include a halogen (iodine, bromine, chlorine, fluorine), an alkyl group (as defined above), an alkoxy group, a hydroxyl group, a halogen-substituted alkyl group, a halogen-substituted alkoxy group and the like, with preference given to a halogen. As used herein, the alkoxy group is an alkoxy group having a straight chain or branched chain alkyl group having 1 to 12 carbon atoms or a cyclic alkyl group having 3 to 10 carbon atoms. Examples thereof include a methoxy group, an ethoxy group, a propoxy group, a 1-methylethoxy group, a butoxy group, a 2-methylpropoxy group, a 1,1-dimethylethoxy group, a pentoxy group, a 3-methylbutoxy group, a hexoxy group, a 4-methylpentoxy group, a cyclopropyloxy group, a cyclobutyloxy group, a cyclopentyloxy group, a cyclohexyloxy group and the like. The halogen-substituted alkyl group and the halogen-substituted alkoxy group are an alkyl group (as defined above) and an alkoxy group (as defined above), which are each substituted by one or plural halogens (as defined above).

In the present specification, the "substituted or unsubstituted aryl-substituted alkyl group" means an unsubstituted aryl-substituted alkyl group or a substituted aryl-substituted alkyl group. The "aryl-substituted alkyl group" is an alkyl group (as defined above) substituted by an aryl group (as defined above), such as a phenylmethyl group (benzyl group), a diphenylmethyl group, a triphenylmethyl group (trityl group), a phenylethyl group (phenethyl group), a 3-phenylpropyl group, a 2-phenylpropyl group, a 4-phenylbutyl group, a biphenylmethyl group, a naphthylmethyl group and the like, with preference given to a benzyl group. Examples of the substituent of the aryl-substituted alkyl group include an alkoxy group (as defined above), a halogen (as defined above), an alkyl group (as defined above), a hydroxyl group, a halogen-substituted alkyl group (as defined above), a halogen-substituted alkoxy group (as defined above) and the like, with preference given to a halogen.

Unless otherwise specified, the positions and numbers of these substituents are optional and are not particularly limited. When substituted by two or more substituents, the substituents may be the same or different.

In the present specification, the "aryl-substituted alkyloxycarbonyl group" means an alkyloxycarbonyl group having a straight chain or branched chain alkyl group having 1 to 12 carbon atoms or a cyclic alkyl group having 3 to 10 carbon atoms, which is substituted by an aryl group (as defined above). Examples thereof include a benzyloxycarbonyl group, a trityloxycarbonyl group, a diphenylmethyloxycarbonyl group, a phenethyloxycarbonyl group and the like, with preference given to a benzyloxycarbonyl group.

In the present specification, the "alkenyl group" means a straight chain or branched chain alkenyl group having 2 to 12 carbon atoms, or a cyclic alkenyl group having 3 to 10 carbon atoms and one unsaturated bond (double bond). Examples thereof include an allyl group, a propenyl group, a butenyl group, a cyclohexenyl group and the like. Preferred is an allyl group.

In the present specification, the "alkynyl group" means a straight chain or branched chain alkynyl group having 2 to 12 carbon atoms, or a cyclic alkynyl group having 3 to 10 carbon atoms and one unsaturated bond (triple bond). Examples thereof include a propargyl group and a 1-pentynyl group.

In the present specification, the "substituted or unsubstituted alicyclic heterocyclic group" means an unsubstituted alicyclic heterocyclic group or a substituted alicyclic heterocyclic group. The "alicyclic heterocycle" is a monocycle free of conjugated double bonds in the maximum number, which is formed by binding of carbon atom with at least one hetero atom such as oxygen atom, nitrogen atom, sulfur atom and the like. Specific examples thereof include a pyrroline ring, a pyrrolidine ring, an imidazoline ring, an imidazolidine ring, a pyrazoline ring, a pyrazolidine ring, a piperidine ring, a piperazine ring, a morpholine ring and the like. Preferred are a morpholine ring, a piperidine ring, a piperazine ring and a pyrrolidine ring, and particularly preferred are a morpholine ring and a piperazine ring. Examples of the substituent of the alicyclic heterocyclic group include an alkyl group (as defined above), an aryl group (as defined above), a carbonyl group (e.g., the aforementioned aryl-substituted alkyloxycarbonyl group) and the like.

$R_1$ and $R_2$ are preferably the same or different and each is a hydrogen atom, an alkyl group, a substituted or unsubstituted benzyl group or a benzyloxycarbonyl group, or $R_1$ and $R_2$ in combination form, together with the adjacent nitrogen atom, a substituted or unsubstituted alicyclic heterocyclic group. More preferably, $R_1$ and $R_2$ are the same or different and each is a hydrogen atom, a lower alkyl group having 1 to 3 carbon atoms or a halogen-substituted benzyl group, or $R_1$ and $R_2$ in combination form, together with the adjacent nitrogen atom, a substituted or unsubstituted morpholine ring, a piperidine ring, a piperazine ring or a pyrrolidine ring (preferably a morpholine ring or a piperazine ring). Examples of the substituent of the alicyclic heterocyclic group include an alkyl group (as defined above), an aryl group (as defined above), a carbonyl group (as defined above) and the like. Preferred is an aryl-substituted alkyloxycarbonyl group, and more preferred is a benzyloxycarbonyl group.

$R_3$ is preferably a hydrogen atom, an acetyl group, a substituted or unsubstituted benzoyl group or a benzyloxycarbonyl group, more preferably a hydrogen atom or an acetyl group.

A is a hydrogen atom, B is a hydroxyl group or a group represented by the following formula [II]

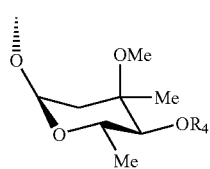

wherein Me is a methyl group, and $R_4$ is a hydrogen atom or an acyl group, or A and B in combination preferably show =O. $R_4$ is particularly preferably a hydrogen atom.

R is preferably a group represented by the following formula [III]

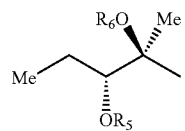

wherein Me is a methyl group, $R_5$ and $R_6$ are the same or different and each is a hydrogen atom or an acyl group, or $R_5$ and $R_6$ in combination show a carbonyl group or a substituted or unsubstituted alkylene group.

Specific examples of preferable compounds of the present invention are shown in the following Tables; however, the compound of the present invention is not limited thereto. The definition of each symbol in the present specification is as follows.

Me: methyl group, Et: ethyl group, iPr: isopropyl group, nHex: n-hexyl group, Ac: acetyl group, Bzl: benzyl group, pCl-Bzl: a benzyl group substituted by a chloro group at the para-position, pBr-Bzl: a benzyl group substituted by a bromo group at the para-position, pF-Bzl: a benzyl group substituted by a fluoro group at the para-position, pI-Bzl: a benzyl group substituted by an iodo group at the para-position, oCl-Bzl: a benzyl group substituted by a chloro group at the ortho-position, mCl-Bzl: a benzyl group substituted by a chloro group at the meta-position, pCF$_3$-Bzl: a benzyl group substituted by a trifluoromethyl group at the para-position, pOMe-Bzl: a benzyl group substituted by a methoxy group at the para-position, Cbz: a benzyloxycarbonyl group, pBr-Bz: a benzoyl group substituted by a bromo group at the para-position, pMe-Bzl: a benzyl group substituted by a methyl group at the para-position.

TABLE 1

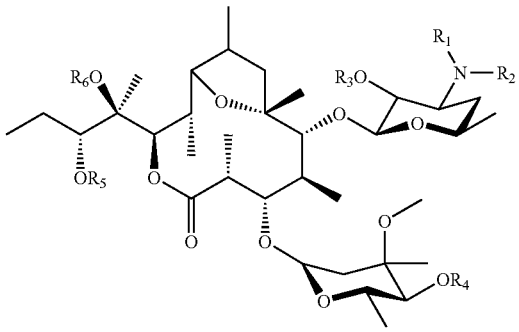

| Compound No. (EM) (Example No.) | $R_1$ | $R_2$ | $R_3$ | $R_4$ | $R_5$ | $R_6$ |
|---|---|---|---|---|---|---|
| 903 (Example 4) | H | H | H | H | H | H |
| 901 (Example 2) | H | Me | H | H | H | H |
| 912 (Example 13) | H | Bzl | H | H | H | H |
| 928 (Example 29) | H | pCl-Bzl | H | H | H | H |
| 900 (Example 1) | Me | Me | H | H | H | H |
| 933 (Example 34) | Me | Et | H | H | H | H |
| 940 (Example 41) | Me | iPr | H | H | H | H |

TABLE 1-continued

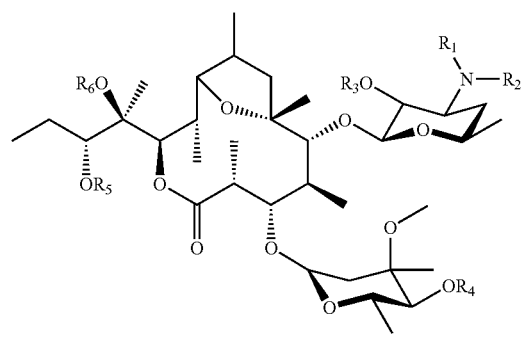

| Compound No. (EM) (Example No.) | R₁ | R₂ | R₃ | R₄ | R₅ | R₆ |
|---|---|---|---|---|---|---|
| 962 (Example 62) | Me | nHex | H | H | H | H |
| 902 (Example 3) | Me | Bzl | H | H | H | H |
| 904 (Example 5) | Bzl | Bzl | H | H | H | H |
| 905 (Example 6) | Me | pCl-Bzl | H | H | H | H |
| 919 (Example 20) | Me | pCF₃-Bzl | H | H | H | H |
| 920 (Example 21) | Me | pBr-Bzl | H | H | H | H |
| 921 (Example 22) | Me | pF-Bzl | H | H | H | H |
| 922 (Example 23) | Me | oCl-Bzl | H | H | H | H |
| 923 (Example 24) | Me | mCl-Bzl | H | H | H | H |
| 924 (Example 25) | Me | pI-Bzl | H | H | H | H |
| 959 (Example 59) | Me | pOMe-Bzl | H | H | H | H |
| 957 (Example 57) | Me | allyl | H | H | H | H |
| 929 (Example 30) | Me | propynyl | H | H | H | H |
| 958 (Example 58) | Me | pMe-Bzl | H | H | H | H |
| 961 (Example 61) | Me | SO₂Me | H | H | H | H |
| 960 (Example 60) | Me | Ac | H | H | H | H |

TABLE 2

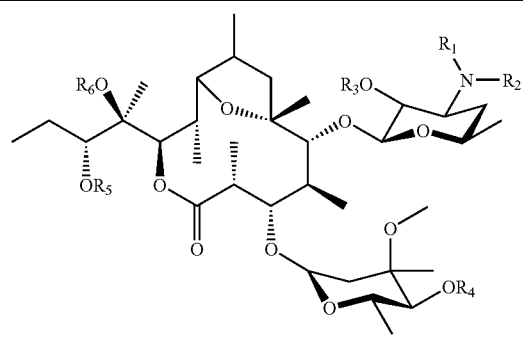

| Compound No. (EM) (Example No.) | R₁ | R₂ | R₃ | R₄ | R₅ | R₆ |
|---|---|---|---|---|---|---|
| 911 (Example 12) | Me | Me | H | Ac | Ac | H |
| 913 (Example 14) | Me | Me | Ac | H | H | H |
| 927 (Example 28) | Me | Me | pBr-Bz | H | H | H |
| 930 (Example 31) | Me | Cbz | Cbz | H | H | H |
| 914 (Example 15) | morpholine | | H | H | H | H |
| 955 (Example 55) | piperidine | | H | H | H | H |
| 956 (Example 56) | pyrrolidine | | H | H | H | H |
| 965 (Example 63) | N-Cbz-piperazine | | H | H | H | H |
| 966 (Example 64) | piperazine | | H | H | H | H |

TABLE 3

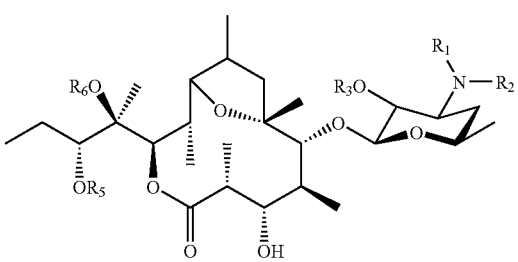

| Compound No. (EM) (Example No.) | R₁ | R₂ | R₃ | R₅ | R₆ |
|---|---|---|---|---|---|
| 910 (Example 11) | Me | Me | H | H | H |
| 934 (Example 35) | Me | H | H | H | H |
| 941 (Example 42) | H | H | H | H | H |
| 915 (Example 16) | Me | Me | Ac | H | H |
| 916 (Example 17) | Me | Me | Ac | C=O | |
| 925 (Example 26) | Me | pCl-Bzl | H | H | H |
| 926 (Example 27) | morpholine | | H | H | H |
| 946 (Example 46) | morpholine | | H | C=O | |
| 948 (Example 48) | morpholine | | Ac | C=O | |
| 931 (Example 32) | Me | Cbz | Cbz | H | H |
| 936 (Example 37) | Me | Cbz | Cbz | C=O | |
| 942 (Example 43) | Me | Cbz | Cbz | C(CH₃)₂ | |
| 950 (Example 50) | morpholine | | H | C(CH₃)₂ | |
| 951 (Example 51) | morpholine | | Ac | C(CH₃)₂ | |

TABLE 4

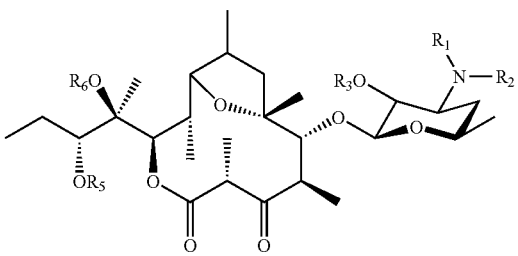

| Compound No. (EM) (Example No.) | R₁ | R₂ | R₃ | R₅ | R₆ |
|---|---|---|---|---|---|
| 918 (Example 19) | Me | Me | H | C=O | |
| 917 (Example 18) | Me | Me | Ac | C=O | |
| 938 (Example 39) | Me | H | H | C=O | |
| 944 (Example 45) | Me | H | H | C(CH₃)₂ | |
| 949 (Example 49) | Me | pCl-Bzl | H | H | H |
| 939 (Example 40) | Me | pCl-Bzl | H | C=O | |
| 947 (Example 47) | Me | pCl-Bzl | H | C(CH₃)₂ | |
| 937 (Example 38) | Me | Cbz | Cbz | C=O | |
| 943 (Example 44) | Me | Cbz | Cbz | C(CH₃)₂ | |
| 935 (Example 36) | morpholine | | H | C=O | |
| 932 (Example 33) | morpholine | | Ac | C=O | |
| 953 (Example 53) | morpholine | | H | C(CH₃)₂ | |
| 952 (Example 52) | morpholine | | Ac | C(CH₃)₂ | |
| 954 (Example 54) | morpholine | | H | H | H |

TABLE 5

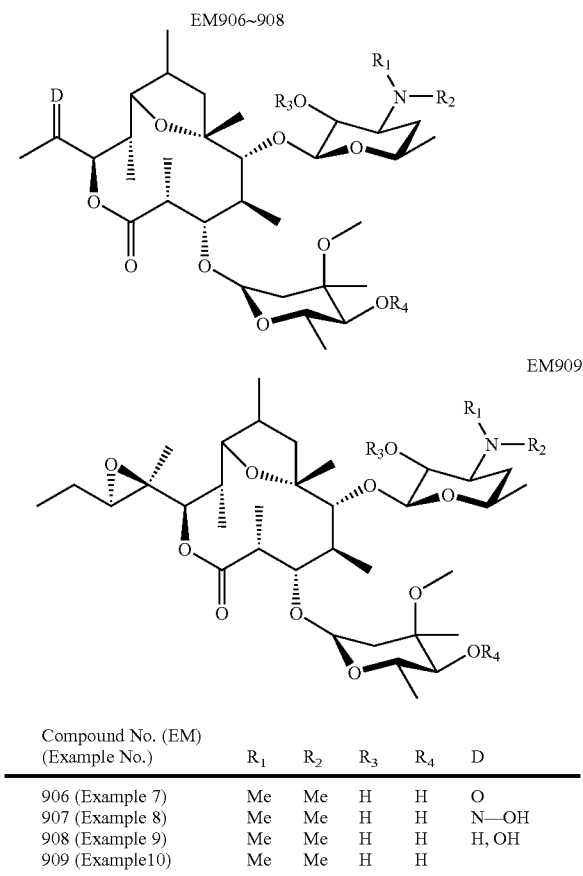

| Compound No. (EM) (Example No.) | R₁ | R₂ | R₃ | R₄ | D |
|---|---|---|---|---|---|
| 906 (Example 7) | Me | Me | H | H | O |
| 907 (Example 8) | Me | Me | H | H | N—OH |
| 908 (Example 9) | Me | Me | H | H | H, OH |
| 909 (Example10) | Me | Me | H | H | |

Particularly preferable compounds are (1) 9-dihydro-pseudoerythromycin A 6,9-epoxide, (2) de(3'-N-methyl)-9-dihydro-pseudoerythromycin A 6,9-epoxide, (3) de(3'-N-methyl)-3'-N-benzyl-9-dihydro-pseudoerythromycin A 6,9-epoxide, (4) bis-de(3'-N-methyl)-9-dihydro-pseudoerythromycin A 6,9-epoxide, (5) bis-de(3'-N-methyl)-bis-(3'-N-benzyl)-9-dihydro-pseudoerythromycin A 6,9-epoxide, (6) de(3'-N-methyl)-3'-N-(p-chlorobenzyl)-9-dihydro-pseudoerythromycin A 6,9-epoxide, (7) de[12-(1-hydroxypropyl)]-9-dihydro-12-oxo-pseudoerythromycin A 6,9-epoxide, (8) de[12-(1-hydroxypropyl)]-9-dihydro-12-hydroxyoxime-pseudoerythromycin A 6,9-epoxide, (9) de[12-(1-hydroxypropyl)]-9-dihydro-pseudoerythromycin A 6,9-epoxide, (10) 12,13-epoxy-9-dihydro-pseudoerythromycin A 6,9-epoxide, (11) de(3-O-cladinosyl)-9-dihydro-pseudoerythromycin A 6,9-epoxide, (12) 4'',13-O-diacetyl-9-dihydro-pseudoerythromycin A 6,9-epoxide, (13) 2'-O-acetyl-9-dihydro-pseudoerythromycin A 6,9-epoxide, (14) de(3'-dimethylamino)-3'-morpholino-9-dihydro-pseudoerythromycin A 6,9-epoxide, (15) 2'-O-acetyl-de(3-O-cladinosyl)-9-dihydro-3-keto-pseudoerythromycin A 6,9-epoxide 12,13-carbonate, (16) de(3-O-cladinosyl)-9-dihydro-3-keto-pseudoerythromycin A 6,9-epoxide 12,13-carbonate, (17) de(3'-N-methyl)-3'-N-(p-chlorobenzyl)-de(3-O-cladinosyl)-9-dihydro-pseudoerythromycin A 6,9-epoxide, (18) 2'-O-acetyl-de(3-O-cladinosyl)-9-dihydro-3-keto-de(3'-dimethylamino)-3'-morpholino-pseudoerythromycin A 6,9-epoxide 12,13-carbonate, (19) de(3-O-cladinosyl)-9-dihydro-3-keto-de(3'-dimethylamino)-3'-morpholino-pseudoerythromycin A 6,9-epoxide 12,13-carbonate, (20) de(3'-N-methyl)-2'-O-3'-N-bis(benzyloxycarbonyl)-de(3-O-cladinosyl)-9-dihydro-pseudoerythromycin A 6,9-epoxide 12,13-carbonate, (21) de(3'-N-methyl)-3'-N-(p-chlorobenzyl)-de(3-O-cladinosyl)-9-dihydro-3-keto-pseudoerythromycin A 6,9-epoxide 12,13-carbonate, (22) de(3-O-cladinosyl)-9-dihydro-de(3'-dimethylamino)-3'-morpholino-pseudoerythromycin A 6,9-epoxide 12,13-carbonate, (23) de(3'-N-methyl)-3'-N-(p-chlorobenzyl)-de(3-O-cladinosyl)-9-dihydro-3-keto-pseudoerythromycin A 6,9-epoxide 12,13-isopropylidene acetal, and (24) de(3'-N-methyl)-3'-N-(p-chlorobenzyl)-de(3-O-cladinosyl)-9-dihydro-3-keto-pseudoerythromycin A 6,9-epoxide.

Further preferable compounds are de(3'-N-methyl)-3'-N-(p-chlorobenzyl)-9-dihydro-pseudoerythromycin A 6,9-epoxide, de(3'-dimethylamino)-3'-morpholino-9-dihydro-pseudoerythromycin A 6,9-epoxide, and de(3'-N-methyl)-3'-N-(p-chlorobenzyl)-de(3-O-cladinosyl)-9-dihydro-3-keto-pseudoerythromycin A 6,9-epoxide 12,13-carbonate.

The production method of the compound of the present invention is not particularly limited and, for example, they can be produced according to the following methods and the like. In addition, the Examples of the present specification more concretely show the production methods of preferable compounds of the present invention. Those of ordinary skill in the art can produce any compound of the present invention by referring to the following general explanations and specific explanations of the Examples, and appropriately modifying or changing starting materials, reaction conditions, reaction reagents and the like as necessary.

For example, of compounds represented by the above-mentioned formula [I], a compound wherein A is a hydrogen atom and B is a group represented by the above-mentioned formula [II] can be produced according to a method shown in the following scheme.

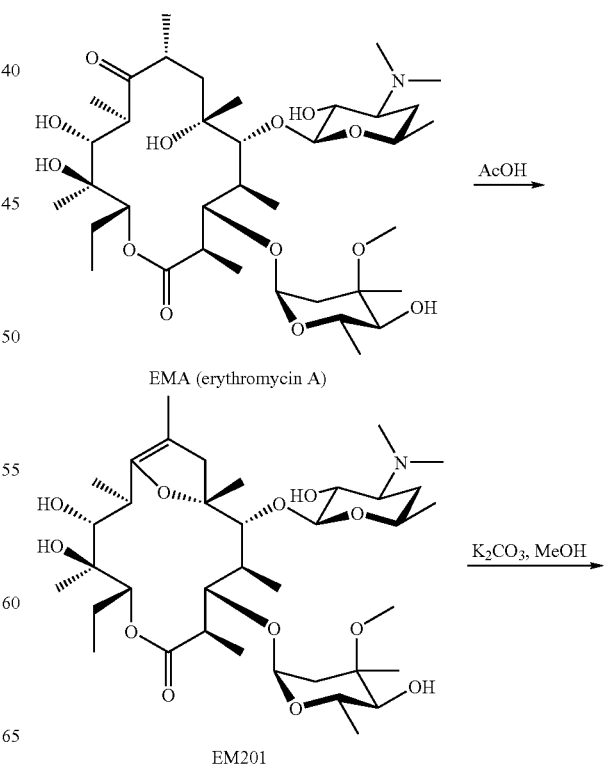

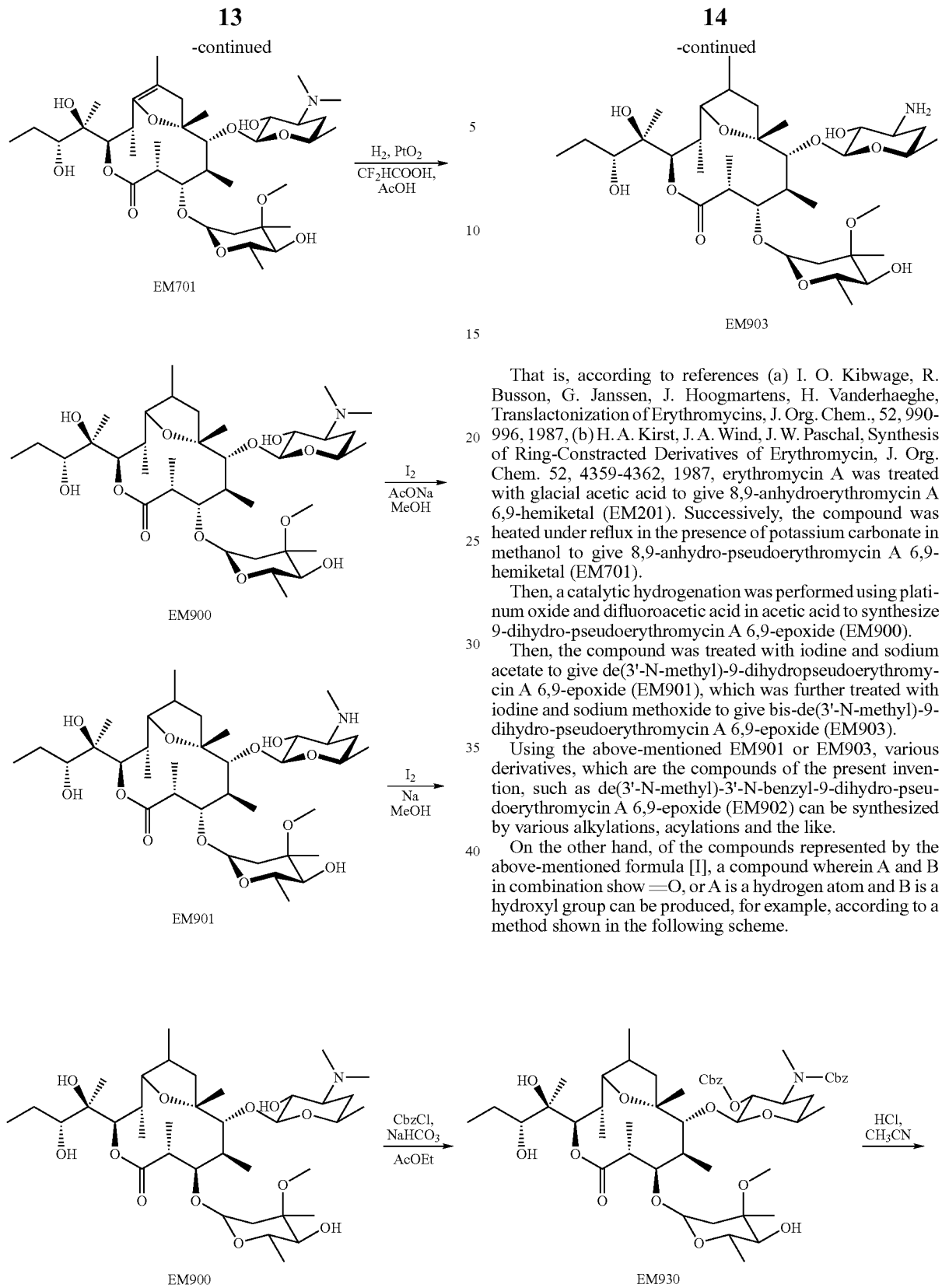

That is, according to references (a) I. O. Kibwage, R. Busson, G. Janssen, J. Hoogmartens, H. Vanderhaeghe, Translactonization of Erythromycins, J. Org. Chem., 52, 990-996, 1987, (b) H. A. Kirst, J. A. Wind, J. W. Paschal, Synthesis of Ring-Constracted Derivatives of Erythromycin, J. Org. Chem. 52, 4359-4362, 1987, erythromycin A was treated with glacial acetic acid to give 8,9-anhydroerythromycin A 6,9-hemiketal (EM201). Successively, the compound was heated under reflux in the presence of potassium carbonate in methanol to give 8,9-anhydro-pseudoerythromycin A 6,9-hemiketal (EM701).

Then, a catalytic hydrogenation was performed using platinum oxide and difluoroacetic acid in acetic acid to synthesize 9-dihydro-pseudoerythromycin A 6,9-epoxide (EM900).

Then, the compound was treated with iodine and sodium acetate to give de(3'-N-methyl)-9-dihydropseudoerythromycin A 6,9-epoxide (EM901), which was further treated with iodine and sodium methoxide to give bis-de(3'-N-methyl)-9-dihydro-pseudoerythromycin A 6,9-epoxide (EM903).

Using the above-mentioned EM901 or EM903, various derivatives, which are the compounds of the present invention, such as de(3'-N-methyl)-3'-N-benzyl-9-dihydro-pseudoerythromycin A 6,9-epoxide (EM902) can be synthesized by various alkylations, acylations and the like.

On the other hand, of the compounds represented by the above-mentioned formula [I], a compound wherein A and B in combination show =O, or A is a hydrogen atom and B is a hydroxyl group can be produced, for example, according to a method shown in the following scheme.

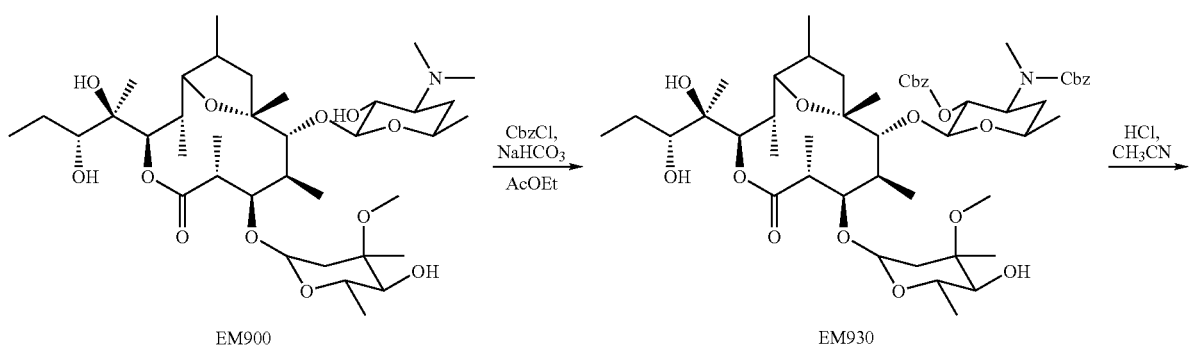

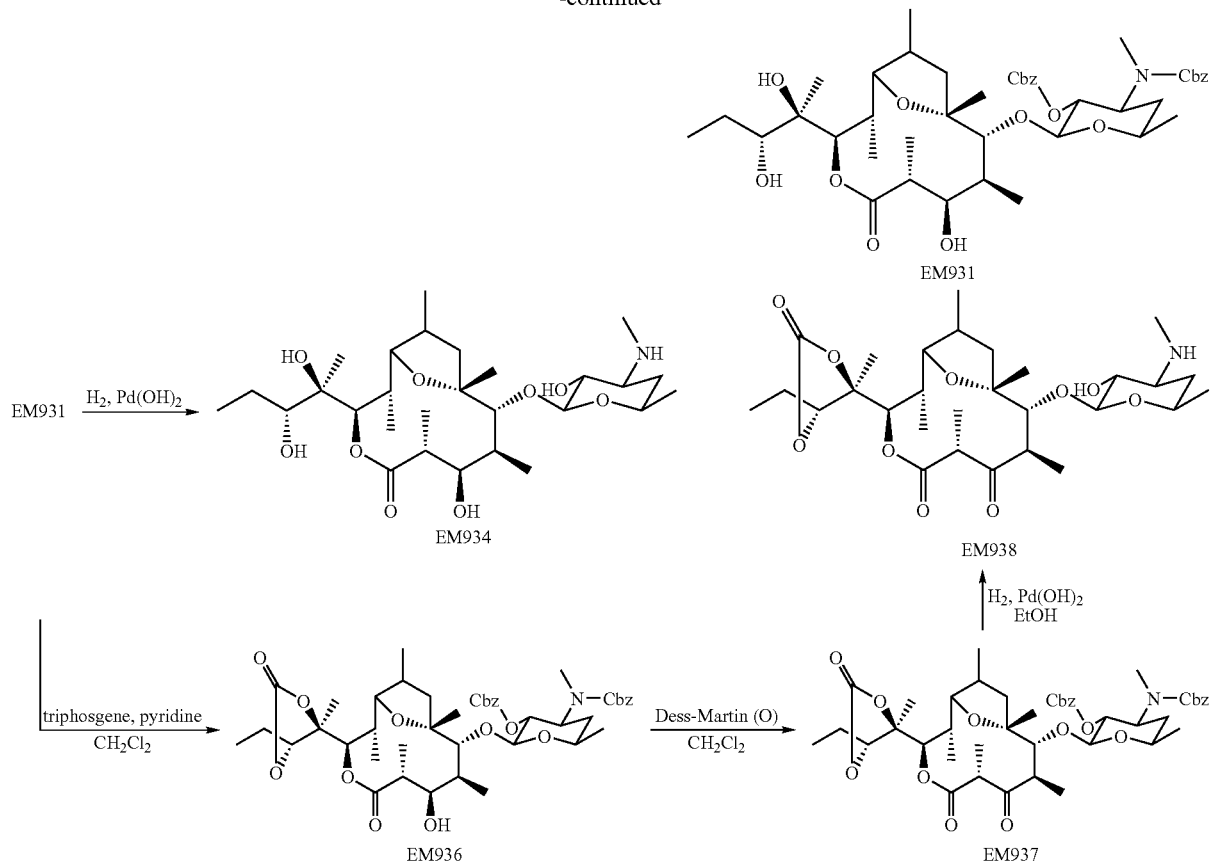

To be specific, the above-mentioned 9-dihydropseudoerythromycin A 6,9-epoxide (EM900) as a starting material is treated with benzyloxycarbonyl chloride to give de(3'-N-methyl)-2'-O-3'-N-bis(benzyloxycarbonyl)-9-dihydro-pseudoerythromycin A 6,9-epoxide (EM930), which is then treated with hydrochloric acid in acetonitrile to give de(3'-N-methyl)-2'-O-3'-N-bis(benzyloxycarbonyl)-de(3-O-cladinosyl)-9-dihydro-pseudoerythromycin A 6,9-epoxide (EM931). The above-mentioned EM931 is subjected to catalytic hydrogenation using a palladium hydroxide catalyst to synthesize de(3-O-cladinosyl)-de(3'-N-methyl)-9-dihydro-pseudoerythromycin A 6,9-epoxide (EM934). EM931 is treated with triphosgene in pyridine to give de(3'-N-methyl)-2'-O-3'-N-bis(benzyloxycarbonyl)-de(3-O-cladinosyl)-9-dihydro-pseudoerythromycin A 6,9-epoxide 12,13-carbonate (EM936), which is then oxidized with a Dess-Martin reagent to give de(3'-N-methyl)-2'-O-3'-N-bis(benzyloxycarbonyl)-de(3-O-cladinosyl)-9-dihydro-3-keto-pseudoerythromycin A 6,9-epoxide 12,13-carbonate (EM937), which is further subjected to catalytic hydrogenation using a palladium hydroxide catalyst to synthesize de(3-O-cladinosyl)-de(3'-N-methyl)-9-dihydro-3-keto-pseudoerythromycin A 6,9-epoxide 12,13-carbonate (EM938).

Using the aforementioned EM934, EM938 or the like, various alkylations, acylations and the like are performed to synthesize various derivatives, which are the compounds of the present invention such as de(3'-N-methyl)-3'-N-(p-chlorobenzyl)-de(3-O-cladinosyl)-9-dihydro-pseudoerythromycin A 6,9-epoxide (EM925).

Examples of the pharmaceutically acceptable salt that can be formed by the compound of the present invention include inorganic acid salts such as hydrochloride, hydrobromide, hydroiodide, sulfate, nitrate, phosphate and the like, organic acid salts such as succinate, fumarate, acetate, methanesulfonate, toluenesulfonate and the like, alkali metal salts such as sodium salt, potassium salt and the like, alkaline earth metal salts such as magnesium salt, calcium salt and the like, ammonium salts such as ammonium salt, alkylammonium salt, etc. and the like.

In addition, solvates of the above-mentioned compound or a pharmaceutically acceptable salt thereof are also encompassed in the present invention. Examples of the solvent include water, methanol, ethanol, isopropanol, acetone, ethyl acetate and the like.

Since the compound of the present invention and a pharmaceutically acceptable salt thereof show a superior anti-inflammatory action on mammals including human such as bovine, horse, dog, mouse, rat and the like, they can be preferably used for the prophylaxis or treatment of inflammatory diseases. Examples of the applicable diseases include Inflammatory Bowel Diseases (IBD) such as Crohn's disease, ulcerative colitis and the like, chronic obliterative pulmonary diseases (COPD), Chronic bronchitis, Respiratory disease, Cystic fibrosis, Diffuse panbronchiolitis (DPB), Pneumonia, Pulmonary fibrosis, Sinusitis, Bronchiectasis, Sinobronchial syndrome, interstitial pneumonia (Pneumonitis), Exudative otitis media, Psoriasis, Pollakiuria, Interstitial cystitis and the like.

As the active ingredient of the pharmaceutical agent of the present invention, one or more substances selected from the above-mentioned compounds and salts thereof as well as their hydrates and solvates can be used. The administration route of the pharmaceutical agent of the present invention is not particularly limited, and the agent can be administered orally or parenterally. As the pharmaceutical agent of the present invention, the above-mentioned substance may be directly administered to patients. Preferably, however, it should be administered as a preparation in the form of a pharmaceutical composition containing an active ingredient and a pharmacologically and pharmaceutically acceptable additive. As the pharmacologically and pharmaceutically acceptable additive, for example, excipient, disintegrant or disintegrant aid, binder, coating agent, dye, diluent, base, solubilizer or solubilizer aid, isotonicity agent, pH regulator, stabilizer, propellant, adhesive and the like can be used. Examples of a preparation suitable for oral administration include tablet, capsule, powder, fine granule, granule, liquid, syrup and the like, and examples of a preparation suitable for parenteral administration include injection, intravenous fluid, ointment, cream, percutaneous absorber, eye drop, eardrop, inhalant, suppository and the like. However, the form of the preparation is not limited to them.

A preparation suitable for oral administration may contain, as an additive, for example, excipient such as glucose, lactose, D-mannitol, starch, crystalline cellulose and the like; disintegrant or disintegrant aid such as carboxymethylcellulose, starch, carboxymethylcellulose calcium and the like; binder such as hydroxypropylcellulose, hydroxypropylmethylcellulose, polyvinylpyrrolidone, gelatin and the like; lubricant such as magnesium stearate, talc and the like; base such as hydroxypropylmethylcellulose, sucrose, polyethylene glycol, gelatin, kaolin, glycerol, purified water, hard fat and the like. A preparation suitable for injection or intravenous fluid may contain additives for preparation such as solubilizer or solubilizer aid capable of constituting an aqueous injection or an injection to be dissolved when in use (e.g., distilled water for injection, saline, propylene glycol and the like); isotonicity agent (e.g., glucose, sodium chloride, D-mannitol, glycerol and the like); pH regulator (e.g., inorganic acid, organic acid, inorganic or organic base, etc.); and the like.

While the dose of the pharmaceutical agent of the present invention appropriately should be varied depending on the kind of disease to be applied to, object of the prophylaxis or treatment, conditions of patients such as age, body weight, symptom and the like, the daily dose for an adult is generally about 0.05-500 mg of the active ingredient by oral administration. In general, the above-mentioned dose can be administered in one to several portions a day, or may be administered every few days. When two or more kinds of the active ingredients are involved, the total amount is set to fall within this range.

EXAMPLES

The present invention is explained in more detail in the following by referring to Starting Material Synthesis Examples, Examples, Experimental Examples and Formulation Examples, which are not to be construed as limitative. All publications cited throughout the present invention are incorporated in full herein by reference. Unless otherwise specified, the reagents, apparatuses and materials to be used in the present invention are commercially available.

Starting Material Synthesis Example 1

Synthesis of 8,9-anhydroerythromycin A 6,9-hemiketal (EM201)

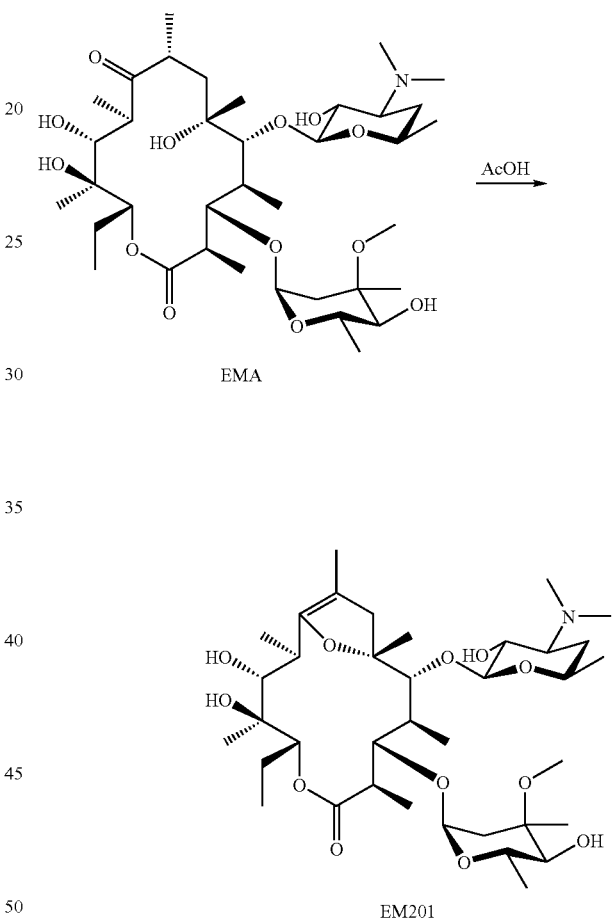

A solution (710.0 mL) of EMA (erythromycin A; 104.4 g, 16.90 mmol) in glacial acetic acid was stirred at room temperature for 2 hr, and aqueous $NaHCO_3$ solution was slowly added to neutralize the solution. The reaction mixture was extracted with $CHCl_3$, and the organic layer was dried over $Na_2SO_4$. The residue was filtrated, and the filtrate was concentrated to give a crude product (99.30 g). The obtained crude product was dissolved in $CHCl_3$ (250 mL), and the solution was recrystallized by adding hexane (50 mL) to give EM201 (74.50 g, 71%) as a white powder.

EM201

Rf=0.63 ($CHCl_3$:MeOH:$NH_4OH$ aq=15:1:0.2)

Starting Material Synthesis Example 2

Synthesis of 8,9-anhydropseudoerythromycin A 6,9-hemiketal (EM701)

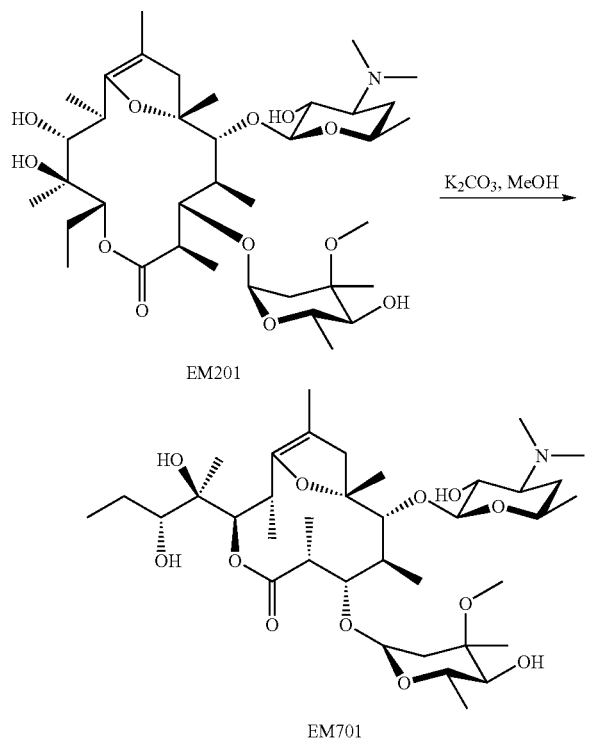

To a solution (150.0 mL) of EM201 (7.600 g, 10.60 mmol) in MeOH was added $K_2CO_3$ (1.400 g, 10.60 mmol), and the mixture was heated under reflux for 2 hr. After cooling to room temperature, the solvent was evaporated, and the residue was dissolved in aqueous $NaHCO_3$ solution. The reaction mixture was extracted with $CHCl_3$, and the organic layer was dried over $Na_2SO_4$. The residue was filtrated, and the filtrate was concentrated to give a crude product (9.300 g). The obtained crude product was separated and purified by flash column chromatography ($CHCl_3$:MeOH:$NH_4$OH aq=10:0.5:0.01-10:1:0.05) to give EM701 (5.900 g, 78%) as a white powder.

EM701
Rf=0.47 ($CHCl_3$:MeOH:$NH_4$OH aq=15:1:0.2)

Example 1

Synthesis of 9-dihydro-pseudoerythromycin A 6,9-epoxide (EM900)

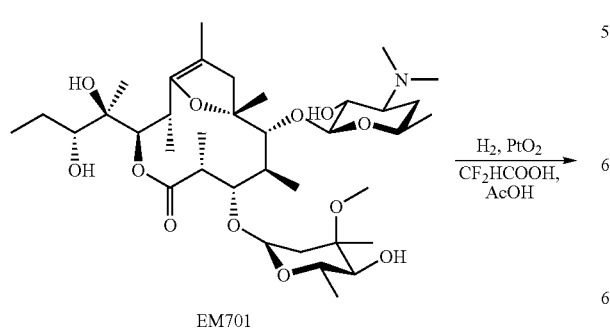

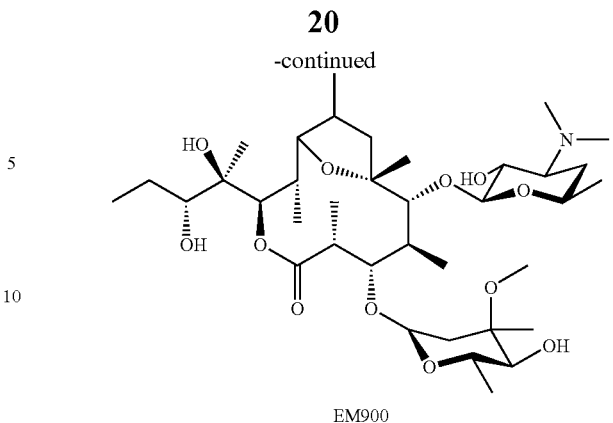

To acetic acid (AcOH; 7.000 mL) were added $PtO_2$ (476.2 mg, 2.100 mmol) and $CF_2HCOOH$ (299.0 µl, 4.750 mmol), and the mixture was stirred under $H_2$ atmosphere at 5 atm and room temperature for 1 hr. A solution (7.000 mL) of EM701 (1.000 g, 1.400 mmol) in AcOH was added, and the mixture was stirred under $H_2$ atmosphere at 5 atm and room temperature for 4 hr. Then, $CH_3CO_2NH_4$ (7.000 g) was added, the mixture was stirred and filtrated, and the filtrate was concentrated. The concentrated solution was extracted with $CHCl_3$, and the extract was washed with saturated aqueous $NaHCO_3$ solution and brine. The washed organic layer was dried over $Na_2SO_4$, the residue was filtrated, and the filtrate was concentrated to give a crude product (968.4 mg). The obtained crude product was separated and purified by flash column chromatography ($CHCl_3$:MeOH:$NH_4$OH aq=50:1:0.02-30:1:0.02) to give EM900 (767.7 mg, 76%) as a white powder.

EM900
Rf=0.53 ($CHCl_3$:MeOH:$NH_4$OH aq=15:1:0.2);
HR-MS m/z: 718.4767 $[M+H]^+$, Calcd for $C_{37}H_{68}NO_{12}$: 718.4742 [M+H]

Example 2

Synthesis of de(3'-N-methyl)-9-dihydro-pseudoerythromycin A 6,9-epoxide (EM901)

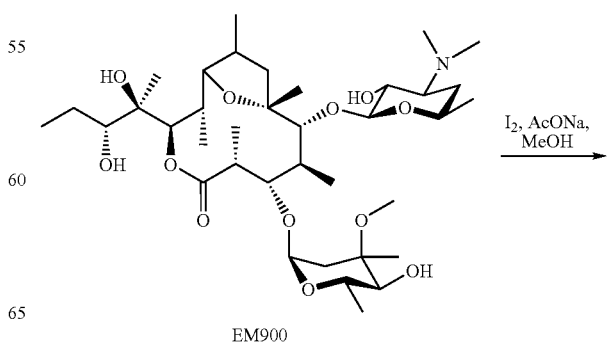

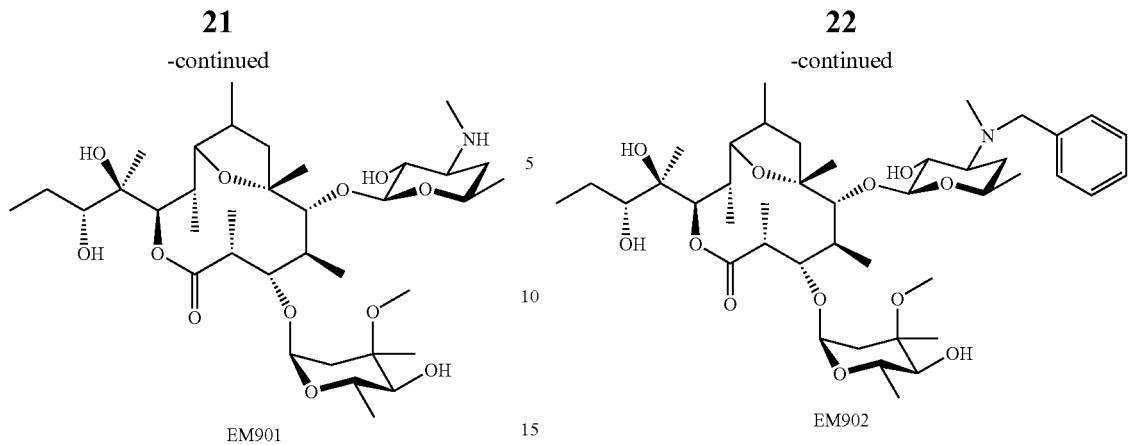

EM901

EM902

To a solution of EM900 (706.3 mg, 0.984 mmol) in methanol (MeOH) (9.840 mL) were added sodium acetate (AcONa; 403.6 mg, 4.920 mmol), 12 (499.5 mg, 1.968 mmol) and saturated NaHCO$_3$ solution, and the mixture was confirmed to be basic with a universal indicator, and stirred at 50° C. for 20 min. After stirring, Na$_2$S$_2$O$_3$ (400.0 mg) was added, and the mixture was cooled to room temperature. The reaction mixture was extracted with CHCl$_3$. After washing with a mixed solution of brine and NH$_4$OH aq, the organic layer was dried over Na$_2$SO$_4$. The residue was filtrated, and the filtrate was concentrated to give a crude product (700.0 mg). The obtained crude product was separated and purified by flash column chromatography (CHCl$_3$:MeOH:NH$_4$OH aq=100:1:0.1-30:1:0.1) to give EM901 (546.5 mg, 79%) as a white powder.

EM901

Rf=0.53 (CHCl$_3$:MeOH:NH$_4$OH aq=10:1:0.2)

HR-MS m/z: 704.4615 [M+H]$^+$, Calcd for C$_{36}$H$_{66}$NO$_{12}$: 704.4585 [M+H]

Example 3

Synthesis of de(3'-N-methyl)-3'-N-benzyl-9-dihydro-pseudoerythromycin A 6,9-epoxide (EM902)

To a solution (850.0 μl) of EM901 (60.00 mg, 0.0852 mmol) in CHCl$_3$ were added diisopropylethylamine (i-Pr$_2$NEt; 74.00 μl, 0.426 mmol) and benzyl bromide (BnBr; 51.00 μl, 0.426 mmol), and the mixture was stirred under Ar atmosphere at room temperature for 1 hr. After stirring, saturated Na$_2$S$_2$O$_3$ solution (10.00 mL) was added, and the mixture was extracted with CHCl$_3$. After washing with saturated Na$_2$S$_2$O$_3$ solution, saturated aqueous NH$_4$Cl solution and brine, the organic layer was dried over Na$_2$SO$_4$. The residue was filtrated, and the filtrate was concentrated to give a crude-product (70.10 mg). The obtained crude product was separated and purified by flash column chromatography (CHCl$_3$:MeOH:NH$_4$OH aq=100:1:0.1) to give EM902 (62.30 mg, 92%) as a white powder.

EM902

HR-MS m/z: 794.5073 [M+H]$^+$, Calcd for C$_{43}$H$_{72}$NO$_{12}$: 794.5055 [M+H]

Example 4

Synthesis of bis-de(3'-N-methyl)-9-dihydro-pseudoerythromycin A 6,9-epoxide (EM903)

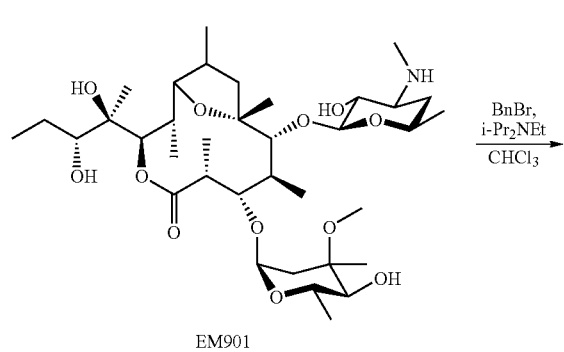

EM901

$\xrightarrow{\text{BnBr,}\\ \text{i-Pr}_2\text{NEt}}{\text{CHCl}_3}$

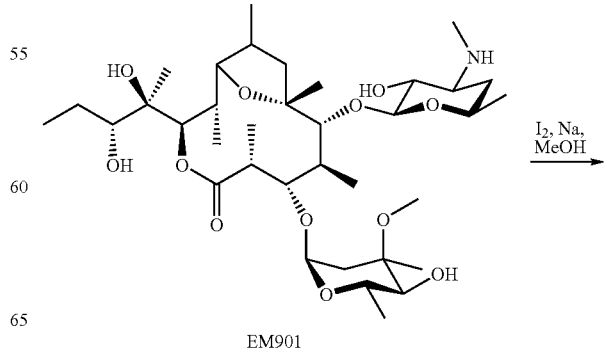

EM901

$\xrightarrow{\text{I}_2\text{, Na,}\\ \text{MeOH}}$

-continued

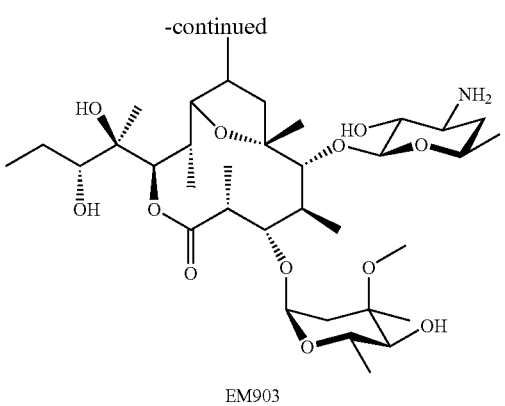

EM903

A solution (15.80 mL) of Na (21.80 mg, 0.9480 mmol) in MeOH was cooled to 0° C., EM901 (111.5 mg, 0.1580 mmol) and I$_2$ (200.5 mg, 0.7900 mmol) were added, and the mixture was stirred under Ar atmosphere at 0° C. for 40 min. After stirring, Na$_2$S$_2$O$_3$ (100.0 mg) was added, and the mixture was warmed to room temperature. The reaction mixture was extracted with CHCl$_3$. After washing with a mixed solution of brine and NH$_4$OH aq, the organic layer was dried over Na$_2$SO$_4$. The residue was filtrated, and the filtrate was concentrated to give a crude product (100.0 mg). The obtained crude product was separated and purified by flash column chromatography (CHCl$_3$:MeOH:NH$_4$OH aq=100:1:0.1-10:1:0.1) to give EM903 (98.40 mg, 90%) as a white powder.

EM903
Rf=0.43 (CHCl$_3$:MeOH:NH$_4$OH aq=10:1:0.2)
HR-MS m/z: 690.4431 [M+H]$^+$, Calcd for C$_{35}$H$_{64}$NO$_{12}$: 690.4429 [M+H]

Example 5

Synthesis of bis-de(3'-N-methyl)-bis-(3'-N-benzyl)-9-dihydro-pseudoerythromycin A 6,9-epoxide (EM904)

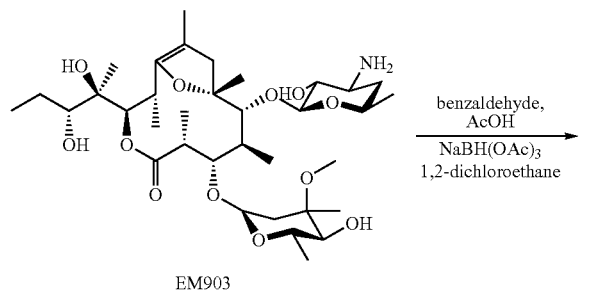

EM903

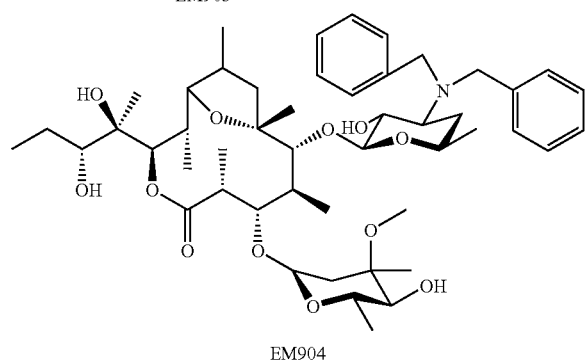

EM904

Under Ar atmosphere, a solution (580.0 μl) of EM903 (20.00 mg, 0.0290 mmol) in 1,2-dichloroethane was cooled to 0° C., benzaldehyde (3.100 μl, 0.0300 mmol), AcOH (2.500 μl, 0.0440 mmol) and NaBH(OAc)$_3$ (9.300 mg, 0.0440 mmol) were added, and the mixture was stirred at 0° C. for 2.5 hr. After stirring, benzaldehyde (14.80 μl, 0.1430 mmol), AcOH (8.300 μl, 0.1460 mmol) and NaBH(OAc)$_3$ (31.00 mg, 0.1460 mmol) were added, and the mixture was warmed to room temperature and stirred for 1 hr. After stirring, saturated NaHCO$_3$ solution (7.000 mL) was added, and the mixture was extracted with CHCl$_3$. After washing with saturated NaHCO$_3$ solution and brine, the organic layer was dried over Na$_2$SO$_4$. The residue was filtrated, and the filtrate was concentrated to give a crude product (23.00 mg). The obtained crude product was separated and purified by flash column chromatography (CHCl$_3$:MeOH:NH$_4$OH aq=100:1:0.1-50:1:0.1) to give EM904 (15.80 mg, 63%) as a white powder.

EM904
HR-MS m/z: 870.5385 [M+H]$^+$, Calcd for C$_{49}$H$_{76}$NO$_{12}$: 870.5368 [M+H]

Example 6

Synthesis of de(3'-N-methyl)-3'-N-(p-chlorobenzyl)-9-dihydro-pseudoerythromycin A 6,9-epoxide (EM905)

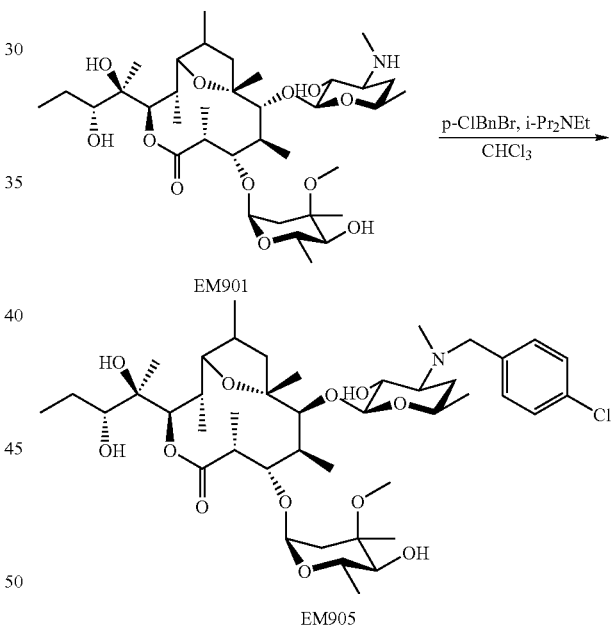

To a solution (280.0 μl) of EM901 (20.00 mg, 0.0280 mmol) in CHCl$_3$ were added i-Pr$_2$NEt (24.40 μl, 0.14 mmol) and p-ClBnBr (p-chlorobenzyl bromide: 28.80 mg, 0.1400 mmol), and the mixture was stirred under N$_2$ atmosphere at room temperature for 2 hr. After stirring, saturated Na$_2$S$_2$O$_3$ solution (7.000 mL) was added, and the mixture was extracted with CHCl$_3$. After washing with saturated Na$_2$S$_2$O$_3$ solution, saturated NH$_4$Cl solution and brine, the organic layer was dried over Na$_2$SO$_4$. The residue was filtrated, and the filtrate was concentrated to give a crude product (24.10 mg). The obtained crude product was separated and purified by flash column chromatography (CHCl$_3$:MeOH:NH$_4$OH aq=100:1:0.1) to give EM905 (21.60 mg, 93%) as a white powder.

EM905

Rf=0.59 (CHCl$_3$:MeOH:NH$_4$OH aq=30:1:0.2)

HR-MS m/z: 828.4657 [M+H]$^+$, Calcd for C$_{43}$H$_{71}$NO$_{12}$Cl: 828.4665 [M+H]

Example 7

Synthesis of de[12-(1-hydroxypropyl)]-9-dihydro-12-oxo-pseudoerythromycin A 6,9-epoxide (EM906)

EM906

HR-MS m/z: 658.4172 [M+H]$^+$, Calcd for C$_{34}$H$_{60}$NO$_{11}$: 658.4166 [M+H]

Example 8

Synthesis of de[12-(1-hydroxypropyl)]-9-dihydro-12-hydroxyoxime-pseudoerythromycin A 6,9-epoxide (EM907)

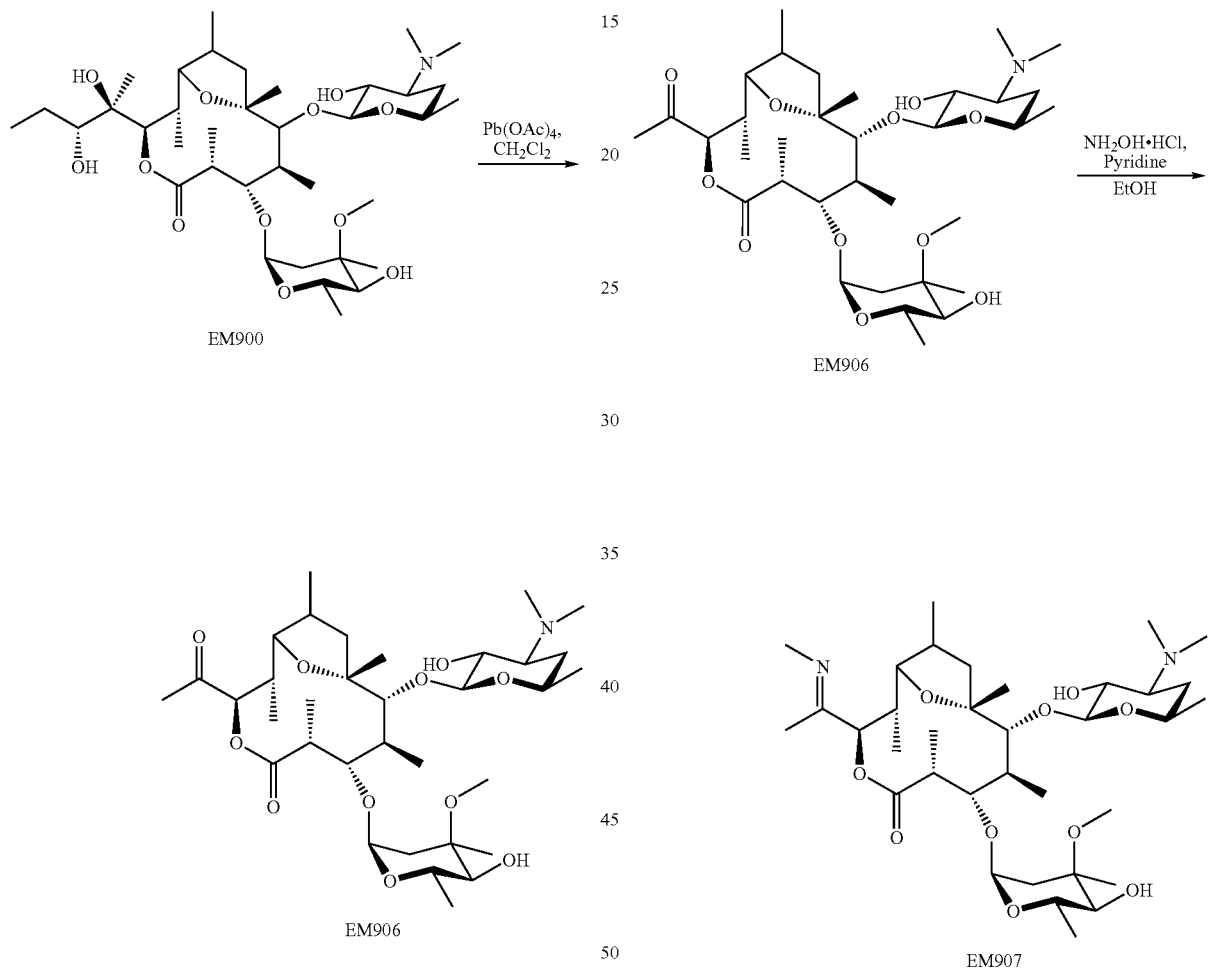

Under N$_2$ atmosphere, a solution (14.00 mL) of EM900 (301.4 mg, 0.420 mmol) in CH$_2$Cl$_2$ was cooled to 0° C., Pb(OAc)$_4$ (300.0 mg, 0.6720 mmol) was added, and the mixture was stirred at 0° C. for 3 hr. After stirring, saturated NaHCO$_3$ solution (25.00 mL) was added, and the mixture was extracted with CHCl$_3$. After washing with saturated NaHCO$_3$ solution and brine, the organic layer was dried over Na$_2$SO$_4$. The residue was filtrated, and the filtrate was concentrated to give a crude product (305.0 mg). The obtained crude product was separated and purified by flash column chromatography (CHCl$_3$:MeOH:NH$_4$OH aq=100:1:0.1-50:1:0.1) to give EM906 (154.7 mg, 56%) as a white powder.

Under N$_2$ atmosphere, a solution (1.100 mL) of EM906 (147.6 mg, 0.2250 mmol) in EtOH was cooled to 0° C., NH$_2$OH.HCl (48.00 mg, 0.6750 mmol) was added, pyridine (1.1 mL, 13.60 mmol) was added dropwise, and the mixture was stirred at 0° C. for 4 hr. After stirring, saturated NaHCO$_3$ solution (5 mL) was added, and the mixture was extracted with CHCl$_3$. The organic layer was dried over Na$_2$SO$_4$. The residue was filtrated, and the filtrate was concentrated to give a crude product (162.0 mg). The obtained crude product was separated and purified by flash column chromatography (CHCl$_3$:MeOH:NH$_4$OH aq=30:1:0.1-10:1:0.1) to give EM907 (140.4 mg, 93%) as a white powder.

EM907

HR-MS m/z: 673.4256 [M+H]$^+$, Calcd for $C_{34}H_{61}N_2O_{11}$: 673.4275 [M+H]

Example 9

Synthesis of de[12-(1-hydroxypropyl)]-9-dihydro-pseudoerythromycin A 6,9-epoxide (EM908)

EM908

HR-MS m/z: 660.4319 [M+H]$^+$, Calcd for $C_{34}H_{62}NO_{11}$: 660.4323 [M+H]

Example 10

Synthesis of 12,13-epoxy-9-dihydro-pseudoerythromycin A 6,9-epoxide (EM909)

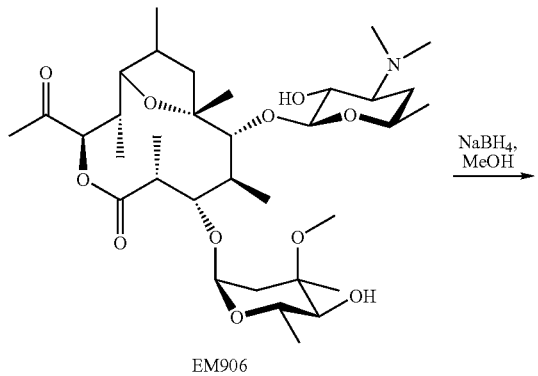

EM906

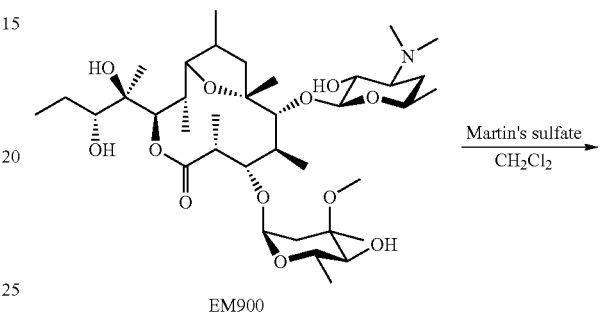

EM900

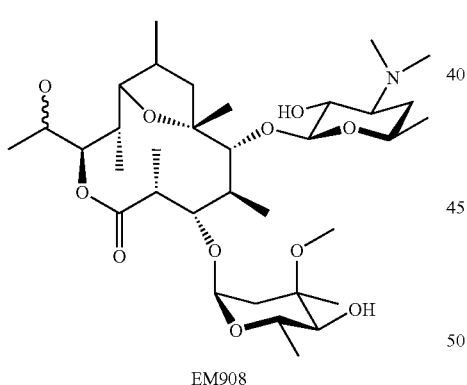

EM908

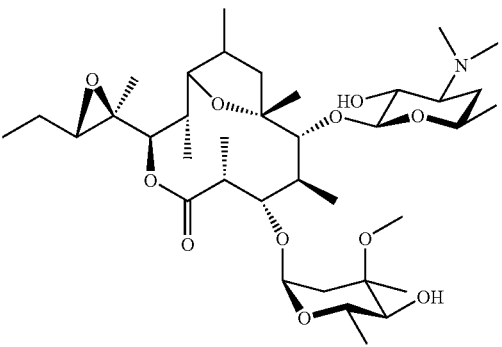

EM909

Under N$_2$ atmosphere, a solution (3.000 mL) of EM906 (39.00 mg, 0.0593 mmol) in MeOH was cooled to −78° C., NaBH$_4$ (22.40 mg, 0.5930 mmol) was added, and the mixture was stirred at −78° C. for 1.5 hr. After stirring, the mixture was warmed to room temperature and diluted with CHCl$_3$, brine (30.00 mL) was added, and the mixture was extracted with CHCl$_3$. After washing with water, the organic layer was dried over Na$_2$SO$_4$. The residue was filtrated, and the filtrate was concentrated to give a crude product (40.30 mg). The obtained crude product was separated and purified by flash column chromatography (CHCl$_3$:MeOH:NH$_4$OH aq=30:1: 0.1-10:1:0.1) to give EM908 (30.80 mg, 79%) as a white powder.

Under N$_2$ atmosphere, to a solution (1.500 mL) of EM900 (106.8 mg, 0.1490 mmol) in CH$_2$Cl$_2$ was added Martin's sulfate (250.0 mg, 0.3720 mmol), and the mixture was stirred for 1.0 hr. After stirring, Martin's sulfate (50.00 mg, 0.0740 mmol) was added, and the mixture was stirred for 0.5 hr. After stirring, saturated NaHCO$_3$ solution (5.000 mL) was added, and the mixture was extracted with CHCl$_3$. After washing with brine, the organic layer was dried over Na$_2$SO$_4$. The residue was filtrated, and the filtrate was concentrated to give a crude product (110.0 mg). The obtained crude product was separated and purified by flash column chromatography (CHCl$_3$:MeOH:NH$_4$OH aq=40:1:0.1-10:1:0.1) to give EM909 (34.60 mg, 33%) as a white powder.

EM909
HR-MS m/z: 700.4655 [M+H]$^+$, Calcd for $C_{37}H_{66}NO_{11}$: 700.4636 [M+H]

Example 11

Synthesis of de(3-O-cladinosyl)-9-dihydro-pseudoerythromycin A 6,9-epoxide (EM910)

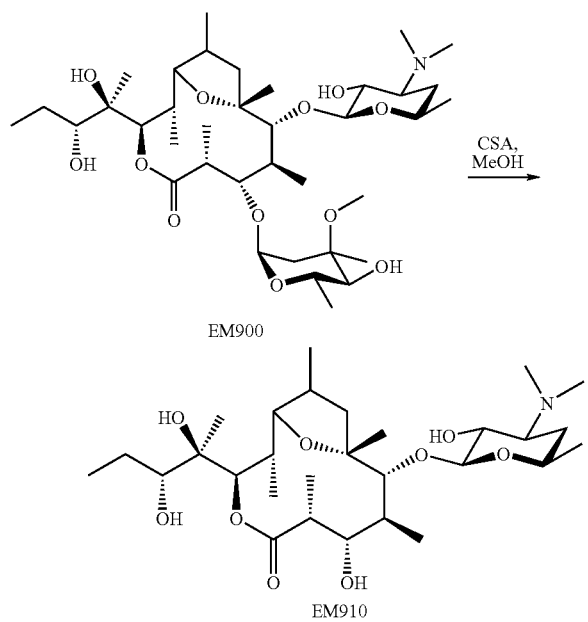

To a solution (1.390 mL) of EM900 (100.0 mg, 0.1390 mmol) in MeOH was added CSA (camphorsulfonic acid: 48.60 mg, 0.2090 mmol), and the mixture was stirred for 3 hr. After stirring, saturated NaHCO$_3$ solution (10.00 mL) was added, and the mixture was extracted with CHCl$_3$. After washing with brine, the organic layer was dried over Na$_2$SO$_4$. The residue was filtrated, and the filtrate was concentrated to give a crude product (99.00 mg). The obtained crude product was separated and purified by flash column chromatography (CHCl$_3$:MeOH:NH$_4$OH aq=50:1:0.1-10:1:0.1) to give EM910 (18.70 mg, 24%) as a white powder.

EM910
HR-MS m/z: 560.3813 [M+H]$^+$, Calcd for $C_{29}H_{54}NO_9$: 560.3799 [M+H]

Example 12

Synthesis of 4'',13-O-diacetyl-9-dihydro-pseudo-erythromycin A 6,9-epoxide (EM911)

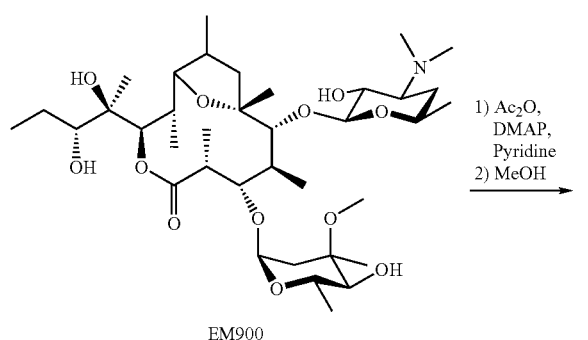

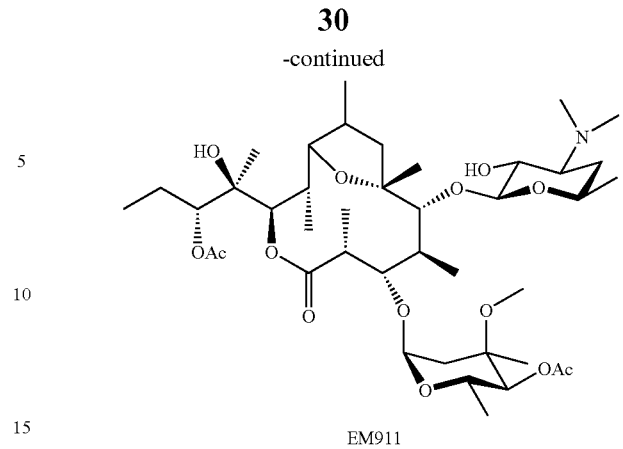

Under N$_2$ atmosphere, to a solution (1.390 mL) of EM900 (100.0 mg, 0.1390 mmol) in pyridine were added DMAP (4-(N,N-dimethylamino)pyridine: 1.698 mg, 0.0139 mmol) and Ac$_2$O (78.69 μl, 0.8340 mmol), and the mixture was stirred for 1 hr. After stirring, DMAP (1.698 mg, 0.0139 mmol) and Ac$_2$O (78.69 μl, 0.8340 mmol) were added, and the mixture was stirred for 2 hr. After stirring, 10% citric acid solution (10.00 mL) was added, and the mixture was extracted with AcOEt. After washing with saturated NaHCO$_3$ solution, the organic layer was dried over Na$_2$SO$_4$. The residue was filtrated, and the filtrate was concentrated to give a crude product (120.0 mg). The obtained crude product was separated and purified by flash column chromatography (CHCl$_3$:MeOH:NH$_4$OH aq=50:1:0.1) to give a resultant product (116.0 mg) as a white powder. A solution (1.390 mL) of this resultant product (116.0 mg) in MeOH was stirred at 50° C. for 12 hr. After stirring, the solution was concentrated to give a crude product (117.1 mg). The obtained crude product was separated and purified by flash column chromatography (CHCl$_3$:MeOH:NH$_4$OH aq=50:1:0.1-10:1:0.1) to give EM911 (104.5 mg, 94%) as a white powder.

EM911
HR-MS m/z: 802.4973 [M+H]$^+$, Calcd for $C_{41}H_{72}NO_{14}$: 802.4953 [M+H]

Example 13

Synthesis of bis-de(3'-N-methyl)-3'-N-benzyl-9-dihydro-pseudoerythromycin A 6,9-epoxide (EM912)

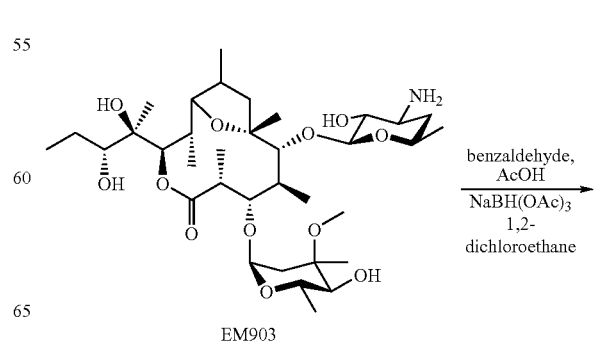

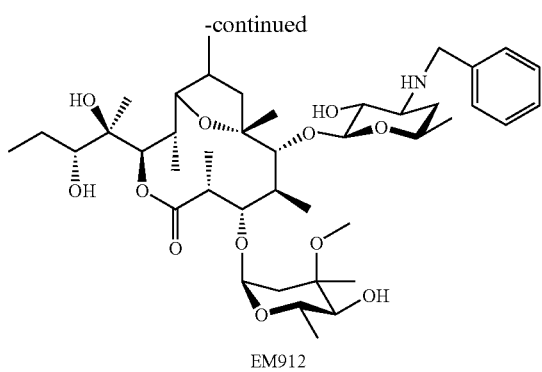

EM912

Under Ar atmosphere, a solution (580.0 μl) of EM903 (20.00 mg, 0.0290 mmol) in 1,2-dichloroethane was cooled to 0° C., benzaldehyde (3.100 μl, 0.0300 mmol), AcOH (2.500 μl, 0.0440 mmol) and NaBH(OAc)$_3$ (9.300 mg, 0.0440 mmol) were added, and the mixture was stirred at 0° C. for 2.5 hr. After stirring, benzaldehyde (14.80 μl, 0.1430 mmol), AcOH (8.300 μl, 0.1460 mmol) and NaBH(OAc)$_3$ (31.00 mg, 0.1460 mmol) were added, and the mixture was warmed to room temperature and stirred for 1 hr. After stirring, saturated NaHCO$_3$ solution (7.000 mL) was added, and the mixture was extracted with CHCl$_3$. After washing with saturated NaHCO$_3$ solution and brine, the organic layer was dried over Na$_2$SO$_4$. The residue was filtrated, and the filtrate was concentrated to give a crude product (23.00 mg). The obtained crude product was separated and purified by flash column chromatography (CHCl$_3$:MeOH:NH$_4$OH aq=100:1:0.1-50:1:0.1) to give EM912 (6.900 mg, 31%) as a white powder.

EM912

HR-MS m/z: 780.4900 [M+H]$^+$, Calcd for C$_{42}$H$_{70}$NO$_{12}$: 780.4898 [M+H]

Example 14

Synthesis of 2'-O-acetyl-9-dihydro-pseudoerythromycin A 6,9-epoxide (EM913)

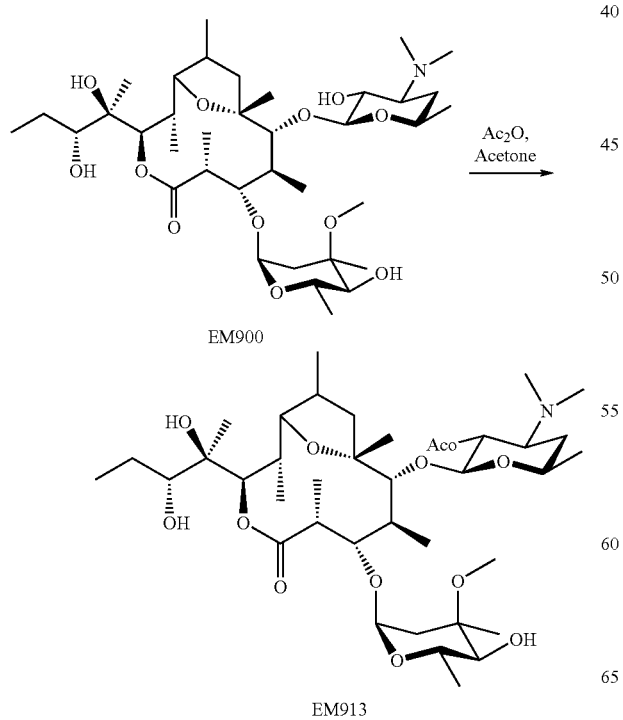

Under N$_2$ atmosphere, to a solution (8.950 mL) of EM900 (641.9 mg, 0.8950 mmol) in acetone was added Ac$_2$O (506.7 μl, 5.370 mmol), and the mixture was stirred for 0.5 hr. After stirring, saturated NaHCO$_3$ solution (100.0 mL) was added, and the mixture was extracted with CHCl$_3$. After washing with saturated NaHCO$_3$ solution, the organic layer was dried over Na$_2$SO$_4$. The residue was filtrated, and the filtrate was concentrated to give a crude product (670.0 mg). The obtained crude product was separated and purified by flash column chromatography (CHCl$_3$:MeOH:NH$_4$OH aq=50:1:0.1-20:1:0.1) to give EM913 (602.3 mg, 89%) as a white powder.

EM913

HR-MS m/z: 760.4879 [M+H]$^+$, Calcd for C$_{39}$H$_{70}$NO$_{13}$: 760.4847 [M+H]

Example 15

Synthesis of de(3'-dimethylamino)-3'-morpholino-9-dihydro-pseudoerythromycin A 6,9-epoxide (EM914)

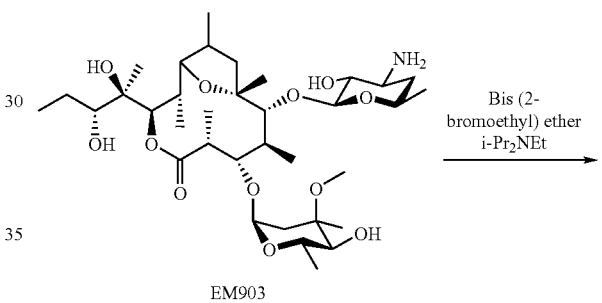

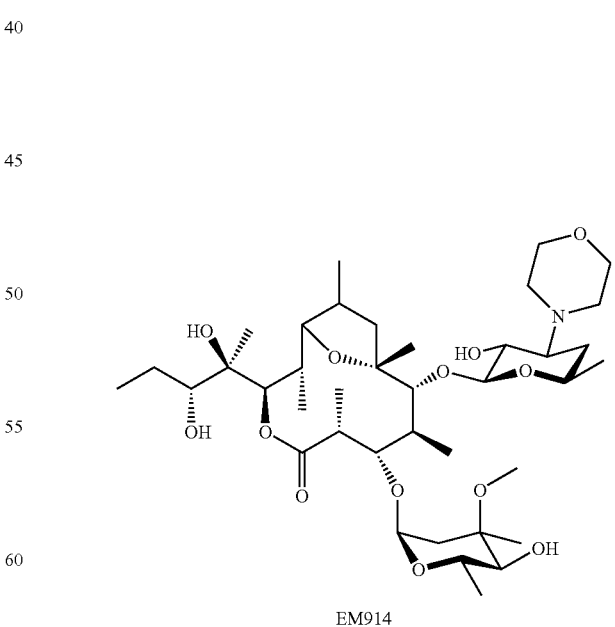

Under Ar atmosphere, to a solution (7.000 mL) of EM903 (24.20 mg, 0.0350 mmol) in CH$_3$CN were added i-Pr$_2$NEt (61.00 μl, 0.3500 mmol) and bis(2-bromoethyl)ether (44.00

μl, 0.3500 mmol), and the mixture was stirred at 80° C. for 20 hr. After stirring, i-Pr$_2$NEt (61.00 μl, 0.3500 mmol) and bis(2-bromoethyl)ether (44.00 μl, 0.3500 mmol) were added, and the mixture was stirred at 80° C. for 6 hr. After stirring, saturated Na$_2$S$_2$O$_3$ solution (7.000 mL) was added, and the mixture was extracted with CHCl$_3$. After washing with saturated Na$_2$S$_2$O$_3$ solution, saturated NH$_4$Cl solution and brine, the organic layer was dried over Na$_2$SO$_4$. The residue was filtrated, and the filtrate was concentrated to give a crude product (36.50 mg). The obtained crude product was separated and purified by flash column chromatography (CHCl$_3$:MeOH:NH$_4$OH aq=100:1:0.1-30:1:0.1) to give EM914 (23.60 mg, 89%) as a white powder.

EM914

Rf=0.44 (CHCl$_3$:MeOH:NH$_4$OH aq=30:1:0.2)

HR-MS m/z: 760.4885 [M+H]$^+$, Calcd for C$_{39}$H$_{70}$NO$_{13}$: 760.4847 [M+H]

Example 16

Synthesis of 2'-O-acetyl-de(3-O-cladinosyl)-9-dihydro-pseudoerythromycin A 6,9-epoxide (EM915)

EM915

HR-MS m/z: 602.3899 [M+H]$^+$, Calcd for C$_{31}$H$_5$6NO$_{10}$: 602.3904 [M+H]

Example 17

Synthesis of 2'-O-acetyl-de(3-O-cladinosyl)-9-dihydro-pseudoerythromycin A 6,9-epoxide 12,13-carbonate (EM916)

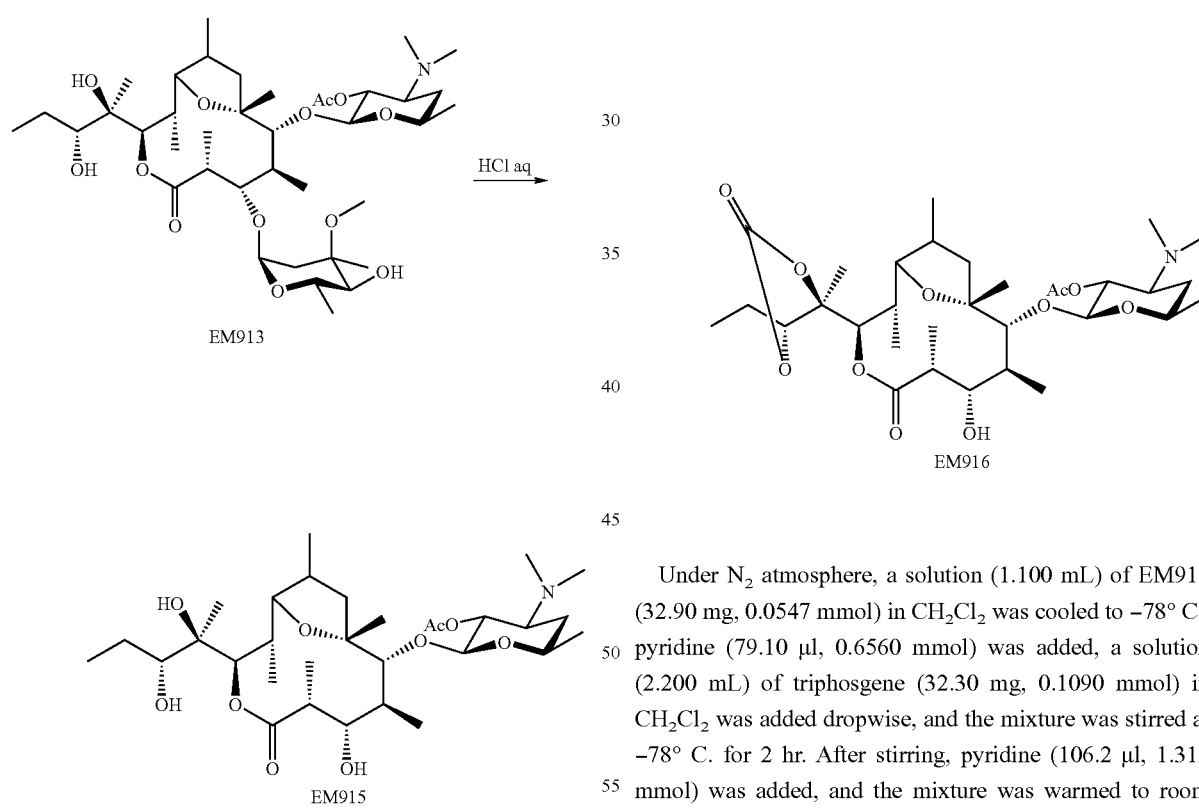

To EM913 (104.5 mg, 0.1380 mmol) was added 1.0N HCl aq (1.380 mL), and the mixture was stirred for 5 hr. After stirring, saturated NaHCO$_3$ solution (20.00 mL) was added, and the mixture was extracted with CHCl$_3$. After washing with brine, the organic layer was dried over Na$_2$SO$_4$. The residue was filtrated, and the filtrate was concentrated to give a crude product (91.10 mg). The obtained crude product was separated and purified by flash column chromatography (CHCl$_3$:MeOH:NH$_4$OH aq=50:1:0.1-20:1:0.1) to give EM915 (37.60 mg, 46%) as a white powder.

Under N$_2$ atmosphere, a solution (1.100 mL) of EM915 (32.90 mg, 0.0547 mmol) in CH$_2$Cl$_2$ was cooled to −78° C., pyridine (79.10 μl, 0.6560 mmol) was added, a solution (2.200 mL) of triphosgene (32.30 mg, 0.1090 mmol) in CH$_2$Cl$_2$ was added dropwise, and the mixture was stirred at −78° C. for 2 hr. After stirring, pyridine (106.2 μl, 1.312 mmol) was added, and the mixture was warmed to room temperature and stirred for 0.5 hr. After stirring, saturated NH$_4$Cl solution (15.00 mL) was added, and the mixture was extracted with CH$_2$Cl$_2$. After washing with saturated NaHCO$_3$ solution and brine, the organic layer was dried over Na$_2$SO$_4$. The residue was filtrated, and the filtrate was concentrated to give a crude product (35.00 mg). The obtained crude product was separated and purified by flash column chromatography (CHCl$_3$:MeOH:NH$_4$OH aq=50:1:0.1-10:1:0.1) to give EM916 (25.00 mg, 73%) as a white powder.

EM916
HR-MS m/z: 628.3697 [M+H]+, Calcd for $C_{32}H_{54}NO_{11}$: 628.3697 [M+H]

Example 18

Synthesis of 2'-O-acetyl-de(3-O-cladinosyl)-9-dihydro-3-keto-pseudoerythromycin A 6,9-epoxide 12,13-carbonate (EM917)

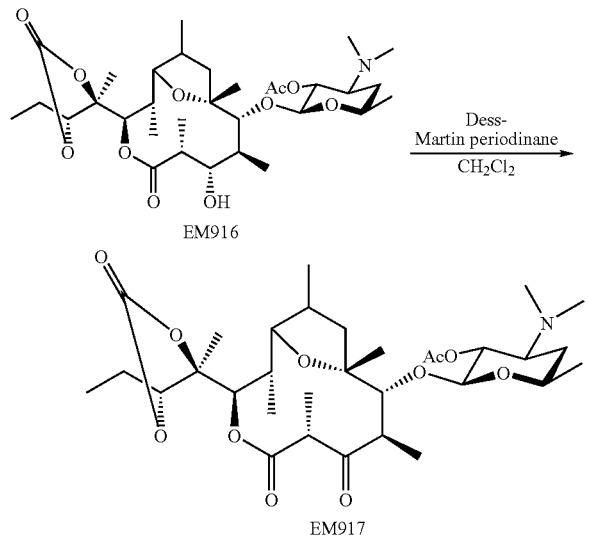

Under $N_2$ atmosphere, to a solution (782.0 μl) of EM916 (24.50 mg, 0.0391 mmol) in $CH_2Cl_2$ was added Dess-Martin periodinane (165.8 mg, 0.3910 mmol), and the mixture was stirred for 2 hr. After stirring, Dess-Martin periodinane (165.8 mg, 0.3910 mmol) was added, and the mixture was stirred for 41 hr. After stirring, saturated $Na_2S_2O_3$ solution (15.00 mL) was added, and the mixture was extracted with EtOAc. After washing with saturated $Na_2S_2O_3$ solution, saturated $NaHCO_3$ solution and brine, the organic layer was dried over $Na_2SO_4$. The residue was filtrated, and the filtrate was concentrated to give a crude product (31.00 mg). The obtained crude product was separated and purified by flash column chromatography ($CHCl_3$:MeOH:$NH_4$OH aq=50:1:0.1) to give EM917 (19.50 mg, 80%) as a white powder.
EM917
MS m/z: 626 [M+H]+

Example 19

Synthesis of de(3-O-cladinosyl)-9-dihydro-3-keto-pseudoerythromycin A 6,9-epoxide 12,13-carbonate (EM918)

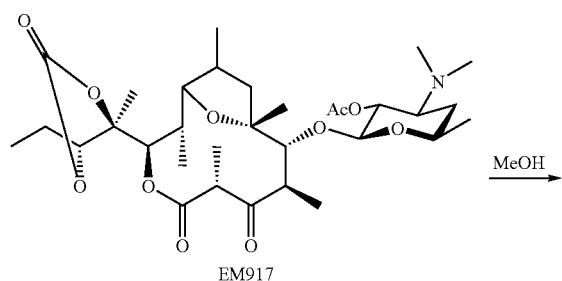

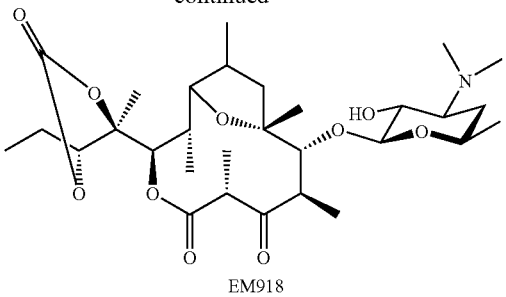

A solution (225.0 μl) of EM917 (14.10 mg, 0.0225 mmol) in MeOH was heated to 50° C., and the mixture was stirred for 30 hr. After stirring, the mixture was concentrated to give a crude product (14.20 mg). The obtained crude product was separated and purified by flash column chromatography ($CHCl_3$:MeOH:$NH_4$OH aq=30:1:0.1) to give EM918 (12.20 mg, 92%) as a white powder.
EM918
HR-MS m/z: 584.3452 [M+H]+, Calcd for $C_{30}H_{50}NO_{10}$: 584.3435 [M+H]

Example 20

Synthesis of de(3'-N-methyl)-9-dihydro-3'-N-(p-trifluoromethylbenzyl)-pseudoerythromycin A 6,9-epoxide (EM919)

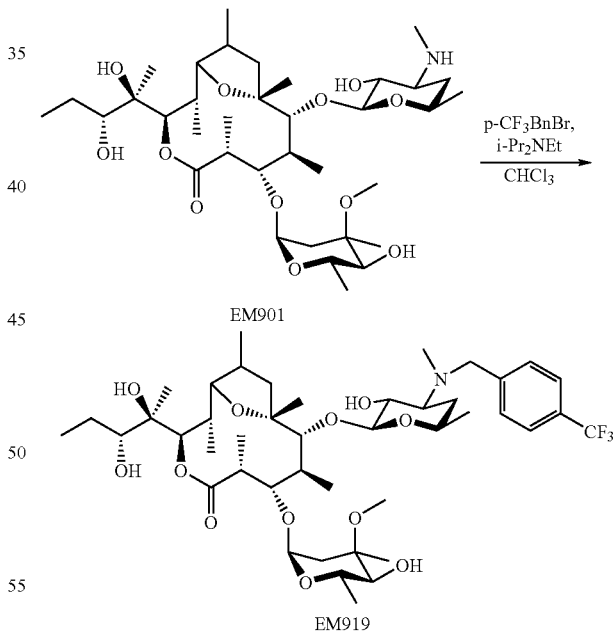

Under $N_2$ atmosphere, to a solution (520.0 μl) of EM901 (36.70 mg, 0.0522 mmol) in $CHCl_3$ were added i-$Pr_2$NEt (45.50 μl, 0.2610 mmol) and p-$CF_3$BnBr (p-trifluoromethylbenzyl bromide: 62.40 mg, 0.2610 mmol), and the mixture was stirred at room temperature for 1 hr. After stirring, i-$Pr_2$NEt (45.50 μl, 0.2610 mmol) and p-$CF_3$BnBr (62.40 mg, 0.2610 mmol) were added, and the mixture was stirred for 2 hr. After stirring, saturated $Na_2S_2O_3$ solution (10.00 mL) was added, and the mixture was extracted with $CHCl_3$. After washing with saturated Na₂S₂O₃ solution, saturated NH₄Cl solution and brine, the organic layer was dried over Na₂SO₄. The residue was filtrated, and the filtrate was concentrated to give a crude product (50.00 mg). The obtained crude product was separated and purified by flash column chromatography (CHCl₃:MeOH:NH₄OH aq=100:1:0.1) to give EM919 (33.30 mg, 74%) as a white powder.

EM919

HR-MS m/z: 862.4966 [M+H]⁺, Calcd for $C_{44}H_{71}NO_{12}F_3$: 862.4928 [M+H]

Example 21

Synthesis of de(3'-N-methyl)-3'-N-(p-bromobenzyl)-9-dihydro-pseudoerythromycin A 6,9-epoxide (EM920)

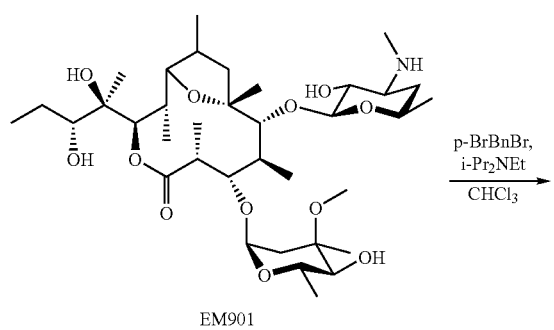

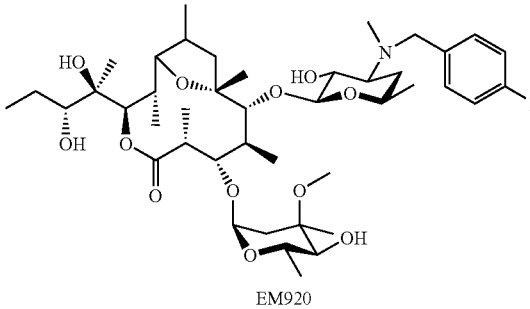

EM920

HR-MS m/z: 872.4158 [M+H]⁺, Calcd for $C_{43}H_{71}NO_{12}Br$: 872.4160 [M+H]

Example 22

Synthesis of de(3'-N-methyl)-3'-N-(p-fluorobenzyl)-9-dihydro-pseudoerythromycin A 6,9-epoxide (EM921)

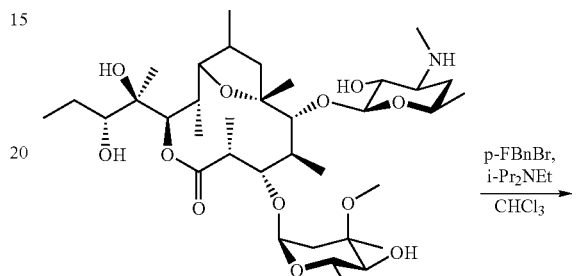

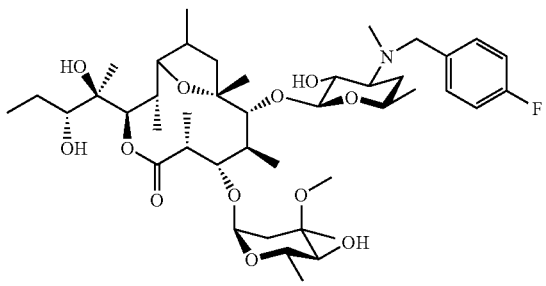

Under N₂ atmosphere, to a solution (574.0 μl) of EM901 (40.40 mg, 0.0574 mmol) in CHCl₃ were added i-Pr₂NEt (50.00 μl, 0.2870 mmol) and p-BrBnBr (p-bromobenzyl bromide: 71.70 mg, 0.2870 mmol), and the mixture was stirred at room temperature for 1 hr. After stirring, i-Pr₂NEt (50.00 μl, 0.2870 mmol) and p-BrBnBr (71.70 mg, 0.2870 mmol) were added, and the mixture was stirred at room temperature for 1 hr. After stirring, saturated Na₂S₂O₃ solution (50.00 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (53.00 mg). The obtained crude product was separated and purified by flash column chromatography (CHCl₃:MeOH:NH₄OH aq=100:1:0.1) to give EM920 (33.30 mg, 67%) as a white powder.

Under N₂ atmosphere, to a solution (607.0 μl) of EM901 (42.70 mg, 0.0607 mmol) in CHCl₃ were added i-Pr₂NEt (53.00 μl, 0.3040 mmol) and p-FBnBr (p-fluorobenzyl bromide: 37.90 μl, 0.3040 mmol), and the mixture was stirred at room temperature for 1 hr. After stirring, i-Pr₂NEt (53.00 μl, 0.3040 mmol) and p-FBnBr (37.90 μl, 0.3040 mmol) were added, and the mixture was stirred at room temperature for 1.5 hr. After stirring, saturated Na₂S₂O₃ solution (40.00 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (50.00 mg). The obtained crude product was separated and purified by flash column chromatography (CHCl₃:MeOH:NH₄OH aq=100:1:0.1) to give EM921 (42.40 mg, 86%) as a white powder.

EM921

HR-MS m/z: 812.4985 [M+H]+, Calcd for $C_{43}H_{71}FNO_{12}$: 812.4960 [M+H]

Example 23

Synthesis of de(3'-N-methyl)-3'-N-(o-chlorobenzyl)-9-dihydro-pseudoerythromycin A 6,9-epoxide (EM922)

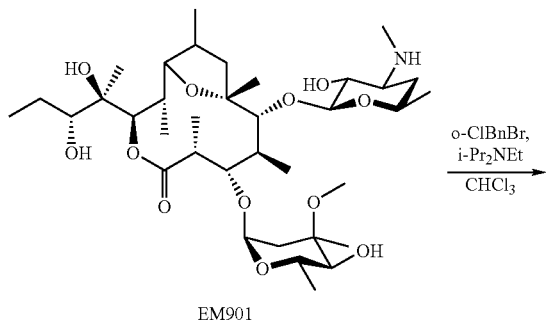
EM901

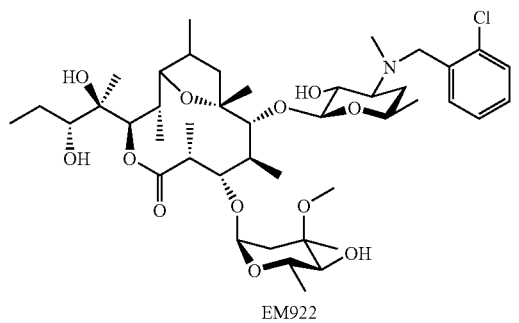
EM922

EM922

HR-MS m/z: 828.4646 [M+H]+, Calcd for $C_{43}H_{71}ClNO_{12}$: 828.4665 [M+H]

Example 24

Synthesis of de(3'-N-methyl)-3'-N-(m-chlorobenzyl)-9-dihydro-pseudoerythromycin A 6,9-epoxide (EM923)

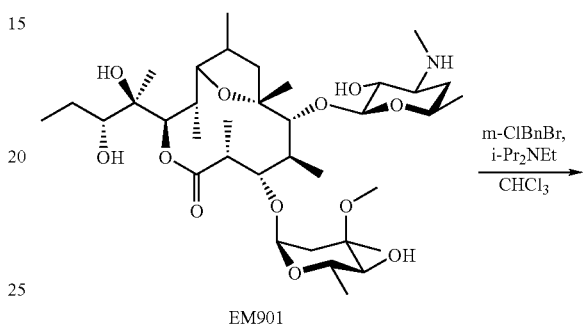
EM901

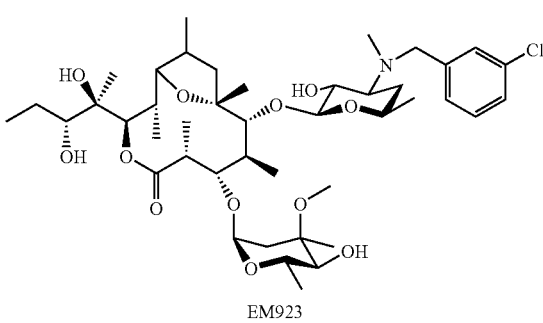
EM923

Under $N_2$ atmosphere, to a solution (597.0 µl) of EM901 (42.00 mg, 0.0597 mmol) in $CHCl_3$ were added i-$Pr_2$NEt (77.50 µl, 0.8960 mmol) and o-ClBnBr (104.0 µl, 0.5970 mmol), and the mixture was stirred at room temperature for 2 hr. After stirring, i-$Pr_2$NEt (38.80 µl, 0.2990 mmol) and o-ClBnBr (52.00 µl, 0.2990 mmol) were added, and the mixture was stirred at room temperature for 0.5 hr. After stirring, saturated $Na_2S_2O_3$ solution (40.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (50.00 mg). The obtained crude product was separated and purified by flash column chromatography ($CHCl_3$: MeOH:$NH_4$OH aq=100:1:0.1) to give EM922 (48.60 mg, 98%) as a white powder.

Under $N_2$ atmosphere, to a solution (634.0 µl) of EM901 (44.60 mg, 0.0634 mmol) in $CHCl_3$ were added i-$Pr_2$NEt (55.20 µl, 0.3170 mmol) and m-ClBnBr (41.60 µl, 0.3170 mmol), and the mixture was stirred at room temperature for 1 hr. After stirring, i-$Pr_2$NEt (55.20 µl, 0.3170 mmol) and m-ClBnBr (41.60 µl, 0.3170 mmol) were added, and the mixture was stirred at room temperature for 2 hr. After stirring, saturated $Na_2S_2O_3$ solution (40.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (55.00 mg). The obtained crude product was separated and purified by flash column chromatography ($CHCl_3$: MeOH:$NH_4$OH aq=100:1:0.1) to give EM923 (45.10 mg, 86%) as a white powder.

EM923
HR-MS m/z: 828.4689 [M+H]$^+$, Calcd for $C_{43}H_{71}ClNO_{12}$: 828.4665 [M+H]

Example 25

Synthesis of de(3'-N-methyl)-9-dihydro-3'-N-(p-iodobenzyl)-pseudoerythromycin A 6,9-epoxide (EM924)

EM924
HR-MS m/z: 920.4011 [M+H]$^+$, Calcd for $C_{43}H_{71}NO_{12}I$: 920.4021 [M+H]

Example 26

Synthesis of de(3'-N-methyl)-3'-N-(p-chlorobenzyl)-de(3-O-cladinosyl)-9-dihydro-pseudoerythromycin A 6,9-epoxide (EM925)

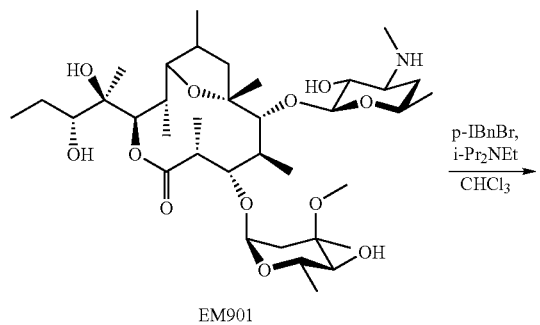
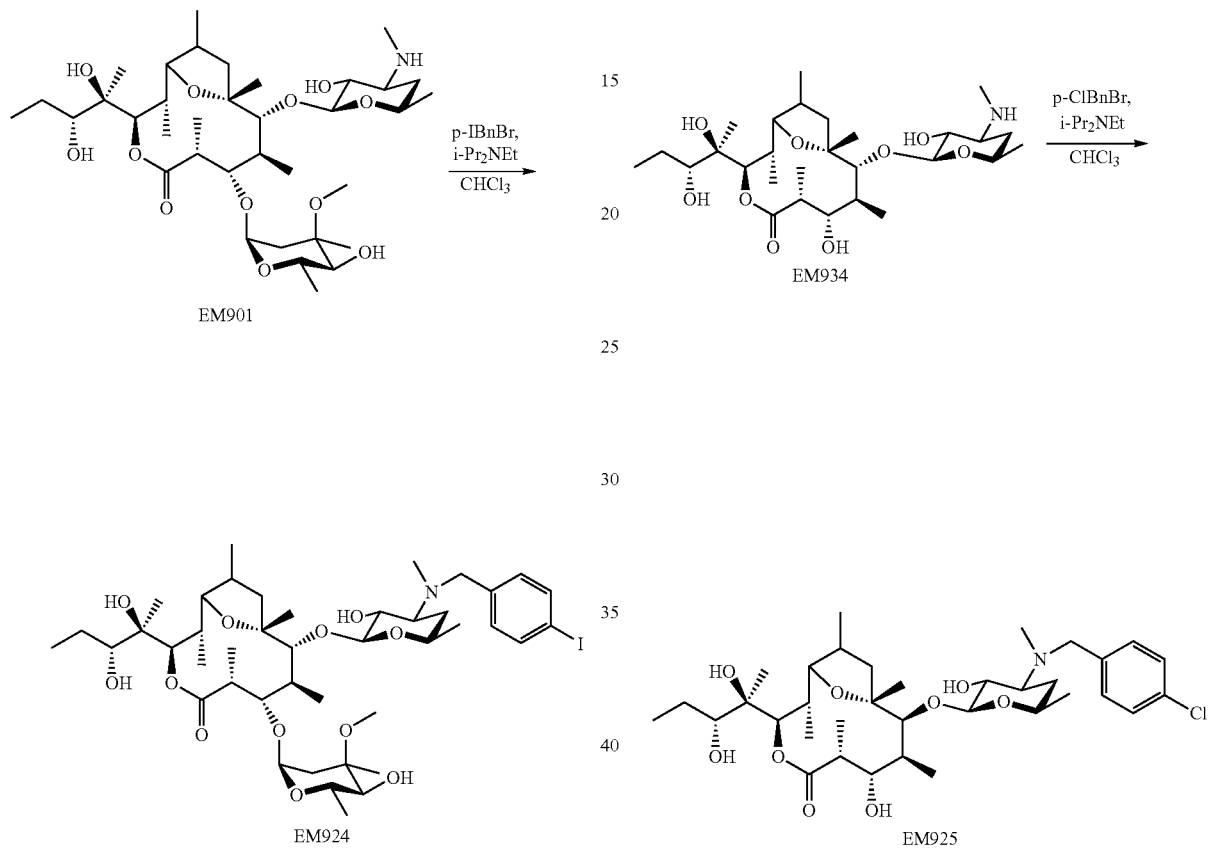

Under $N_2$ atmosphere, to a solution (580.0 µl) of EM901 (40.80 mg, 0.0580 mmol) in $CHCl_3$ were added i-$Pr_2NEt$ (50.50 µl, 0.2900 mmol) and p-IBnBr (p-iodobenzyl bromide: 86.10 mg, 0.2900 mmol), and the mixture was stirred at room temperature for 1 hr. After stirring, i-$Pr_2NEt$ (50.50 µl, 0.2900 mmol) and p-IBnBr (86.10 mg, 0.2900 mmol) were added, and the mixture was stirred at room temperature for 2 hr. After stirring, saturated $Na_2S_2O_3$ solution (40.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (55.00 mg). The obtained crude product was separated and purified by flash column chromatography ($CHCl_3$:MeOH:$NH_4OH$ aq=100:1:0.1) to give EM924 (48.20 mg, 90%) as a white powder.

Under $N_2$ atmosphere, to a solution (689.0 µl) of EM934 (37.60 mg, 0.0689 mmol) obtained in the below-mentioned Example 35 in $CHCl_3$ were added i-$Pr_2NEt$ (120.0 µl, 0.6890 mmol) and p-ClBnBr (141.6 mg, 0.6890 mmol), and the mixture was stirred at room temperature for 2 hr. After stirring, saturated $Na_2S_2O_3$ solution (40.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (50.00 mg). The obtained crude product was separated and purified by flash column chromatography ($CHCl_3$:MeOH:$NH_4OH$ aq=100:1:0.1) to give EM925 (33.00 mg, 72%) as a white powder.

EM925

HR-MS m/z: 670.3705 [M+H]$^+$, Calcd for $C_{35}H_{57}ClNO_9$: 670.3722 [M+H]

Example 27

Synthesis of de(3-O-cladinosyl)-de(3'-dimethylamino)-3'-morpholino-9-dihydro-pseudoerythromycin A 6,9-epoxide (EM926)

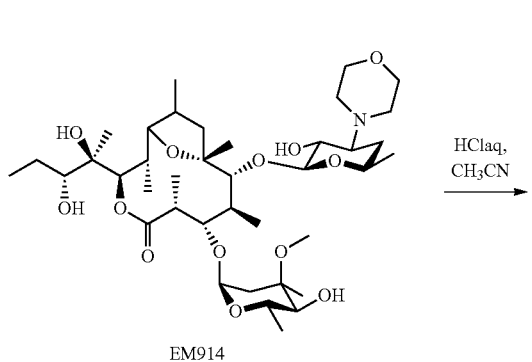

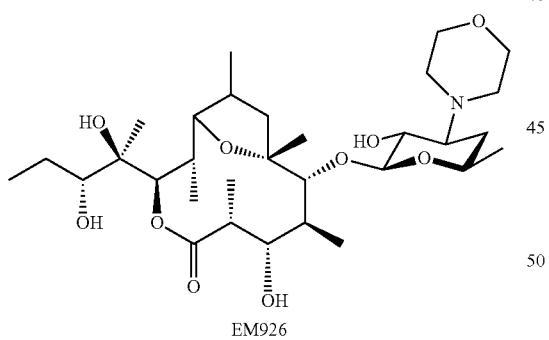

To a solution (937.0 µl) of EM914 (71.20 mg, 0.0937 mmol) in CH$_3$CN was added 1.0N HCl aq (937.0 µl), and the mixture was stirred for 0.5 hr. After stirring, saturated NaHCO$_3$ solution (50.00 mL) was added, and the mixture was extracted with CHCl$_3$. After washing with brine, the organic layer was dried over Na$_2$SO$_4$. The residue was filtrated, and the filtrate was concentrated to give a crude product (60.00 mg). The obtained crude product was separated and purified by flash column chromatography (CHCl$_3$:MeOH:NH$_4$OH aq=50:1:0.1-30:1:0.1) to give EM926 (25.30 mg, 44%) as a white powder.

EM926

HR-MS m/z: 602.3884 [M+H]$^+$, Calcd for $C_{31}H_{56}NO_{10}$: 602.3904 [M+H]

Example 28

Synthesis of 2'-O-(p-bromobenzoyl)-9-dihydro-pseudoerythromycin A 6,9-epoxide (EM927)

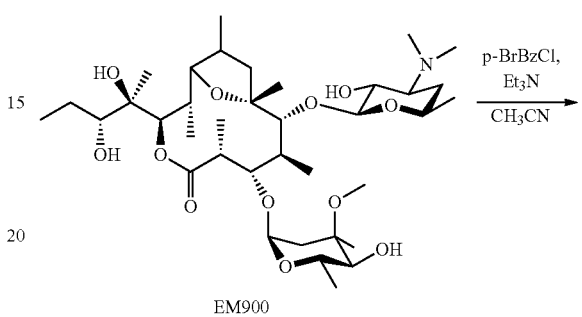

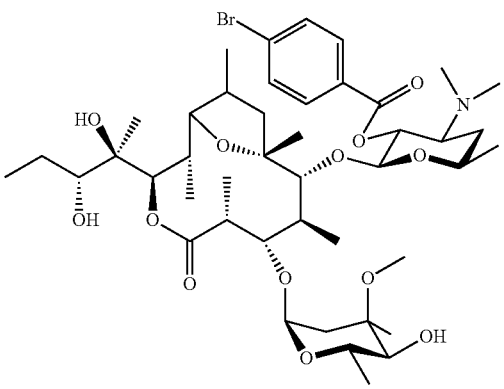

Under N$_2$ atmosphere, to a solution (4.200 mL) of EM900 (100.8 mg, 0.1400 mmol) in CH$_3$CN were added Et$_3$N (58.30 µl, 0.4200 mmol) and p-BrBzCl (p-bromobenzoyl chloride: 30.70 mg, 0.1400 mmol), and the mixture was stirred for 1.0 hr. After stirring, aqueous NH$_3$ solution (6.000 mL) was added, and the mixture was concentrated to give a crude product (126.0 mg). The obtained crude product was separated and purified by flash column chromatography (CHCl$_3$:MeOH:NH$_4$OH aq=50:1:0.1-30:1:0.1) to give EM927 (107.4 mg, 85%) as a white powder.

EM927

HR-MS m/z: 900.4091 [M+H]$^+$, Calcd for $C_{44}H_{71}NO_{13}Br$: 900.4109 [M+H]

Example 29

Synthesis of bis-de(3'-N-methyl)-3'-N-(p-chlorobenzyl)-9-dihydro-pseudoerythromycin A 6,9-epoxide (EM928)

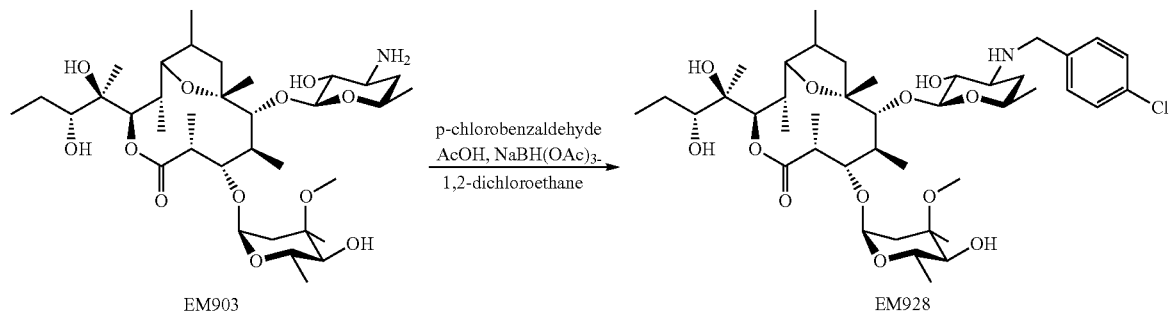

Under $N_2$ atmosphere, a solution (1.440 mL) of EM903 (49.60 mg, 0.0719 mmol) in 1,2-dichloroethane was cooled to 0° C., p-chlorobenzaldehyde (10.60 mg, 0.0755 mmol), AcOH (6.180 μl, 0.1080 mmol) and NaBH(OAc)$_3$ (22.90 mg, 0.1080 mmol) were added, and the mixture was stirred at 0° C. for 2.5 hr, warmed to room temperature and stirred for 1 hr. After stirring, saturated NaHCO$_3$ solution (50.00 mL) was added, and the mixture was extracted with CHCl$_3$. After washing with saturated NaHCO$_3$ solution and brine, the organic layer was dried over Na$_2$SO$_4$. The residue was filtrated, and the filtrate was concentrated to give a crude product (62.00 mg). The obtained crude product was separated and purified by flash column chromatography (CHCl$_3$:MeOH:NH$_4$OH aq=100:1:0.1-10:1:0.1) to give EM928 (32.30 mg, 55%) as a white powder.

EM928

HR-MS m/z: 814.4515 [M+H]$^+$, Calcd for $C_{42}H_{69}ClNO_{12}$: 814.4508 [M+H]

Example 30

Synthesis of de(3'-N-methyl)-3'-N-propargyl-9-dihydro-pseudoerythromycin A 6,9-epoxide (EM929)

solution, and the mixture was confirmed to be basic using universal indicator and stirred at 50° C. for 20 min. After stirring, Na$_2$S$_2$O$_3$ (400.0 mg) was added, and the mixture was cooled to room temperature. The reaction mixture was extracted with CHCl$_3$. After washing with a mixed solution of brine and NH$_4$OH, the organic layer was dried over Na$_2$SO$_4$. The residue was filtrated, and the filtrate was concentrated to give a crude product. Under N$_2$ atmosphere, i-Pr$_2$NEt (1.100 mL, 6.335 mmol) and 3-bromopropyne (471.9 μl, 6.335 mmol) were added to a solution (12.67 mL) of the obtained crude product (892.0 mg, 1.267 mmol) in CHCl$_3$, and the mixture was stirred at room temperature for 1 hr. After stirring, i-Pr$_2$NEt (1.100 mL, 6.335 mmol) and 3-bromopropyne (471.9 μl, 6.335 mmol) were added, and the mixture was stirred at room temperature for 12 hr. After stirring, saturated Na$_2$S$_2$O$_3$ solution (200.0 mL) was added, and the mixture was extracted with CHCl$_3$. After washing with saturated Na$_2$S$_2$O$_3$ solution, saturated NH$_4$Cl solution and brine, the organic layer was dried over Na$_2$SO$_4$. The residue was filtrated, and the filtrate was concentrated to give a crude product (940.2 mg). The obtained crude product was separated and purified by flash column chromatography (CHCl$_3$:MeOH:NH$_4$OH

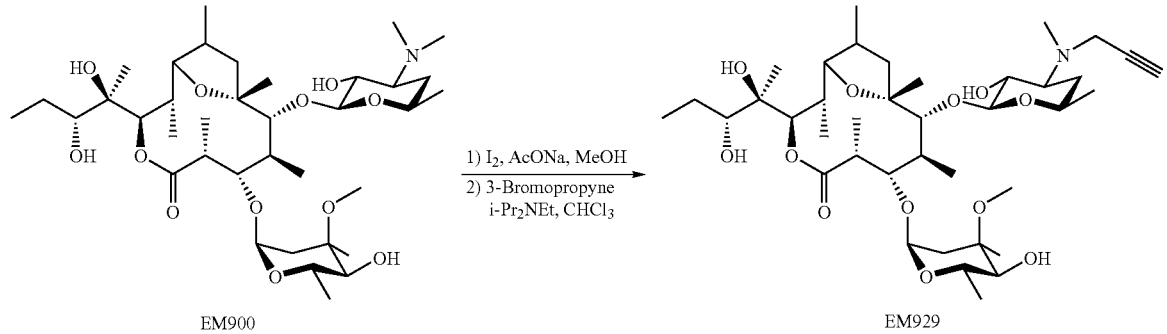

To a solution (12.67 mL) of EM900 (909.3 mg, 1.267 mmol) in MeOH were added AcONa (519.7 mg, 6.335 mmol), I$_2$ (643.2 mg, 2.534 mmol) and saturated NaHCO$_3$ aq=100:1:0.1) to give EM929 (600.1 mg, 64%) as a white powder.

EM929

HR-MS m/z: 742.4730-[M+H]$^+$, Calcd for $C_{39}H_{68}NO_{12}$: 742.4742 [M+H]

Example 31

Synthesis of de(3'-N-methyl)-2'-O-3'-N-bis(benzyloxycarbonyl)-9-dihydro-pseudoerythromycin A 6,9-epoxide (EM930)

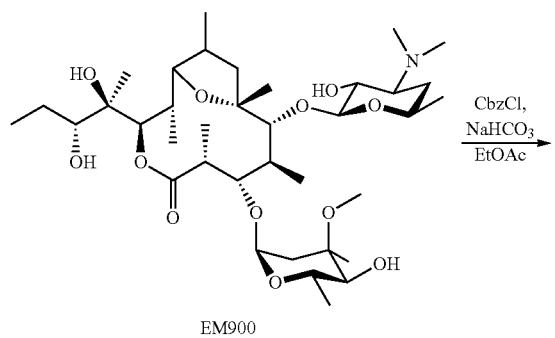

EM930

HR-MS m/z: 994.5170 [M+Na]$^+$, Calcd for $C_{52}H_{77}NO_{16}Na$: 994.5140 [M+Na]

Example 32

Synthesis of de(3'-N-methyl)-2'-O-3'-N-bis(benzyloxycarbonyl)-de(3-O-cladinosyl)-9-dihydro-pseudoerythromycin A 6,9-epoxide (EM931)

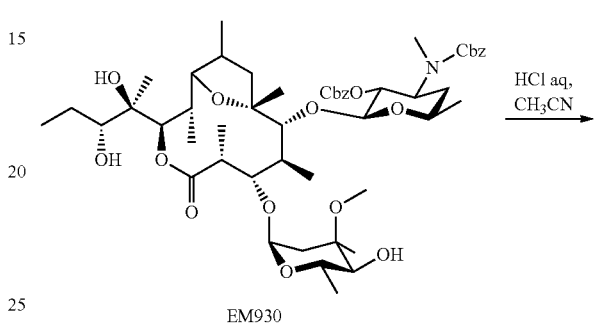

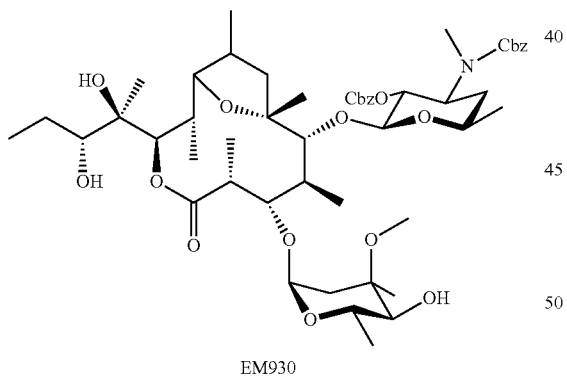

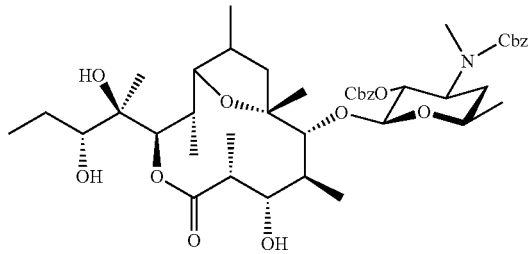

To a solution (69.80 mL) of EM900 (5.004 g, 6.975 mmol) in EtOAc was added NaHCO$_3$ (8.790 g, 104.6 mmol), CbzCl (benzyloxycarbonyl chloride: 14.93 mL, 104.6 mmol) was added dropwise, and the mixture was heated to 70° C. and stirred for 2 hr. After stirring, Et$_3$N was added, and the mixture was cooled to room temperature. The reaction mixture was extracted with EtOAc. After washing with brine, the organic layer was dried over Na$_2$SO$_4$. The residue was filtrated, and the filtrate was concentrated to give a crude product (7.000 g). The obtained crude product was separated and purified by flash column chromatography (CHCl$_3$:MeOH: NH$_4$OH aq=50:1:0.1) to give EM930 (6.365 g, 94%) as a white powder.

To a solution (104.6 mL) of EM930 (5.081 g, 5.230 mmol) in CH$_3$CN was added 1.0N HCl aq (52.30 mL), and the mixture was stirred for 4 hr. After stirring, saturated NaHCO$_3$ solution (400.0 mL) was added, and the mixture was extracted with CHCl$_3$. After washing with brine, the organic layer was dried over Na$_2$SO$_4$. The residue was filtrated, and the filtrate was concentrated to give a crude product (4.312 g). The obtained crude product was separated and purified by flash column chromatography (CHCl$_3$:MeOH:NH$_4$OH aq=50:1:0.1) to give EM931 (4.028 g, 95%) as a white powder.

EM931

HR-MS m/z: 814.4384 [M+H]+, Calcd for $C_{44}H_{64}NO_{13}$: 814.4378 [M+H]

Example 33

Synthesis of 2'-O-acetyl-de(3-O-cladinosyl)-9-dihydro-3-keto-de(3'-dimethylamino)-3'-morpholino-pseudoerythromycin A 6,9-epoxide 12,13-carbonate (EM932)

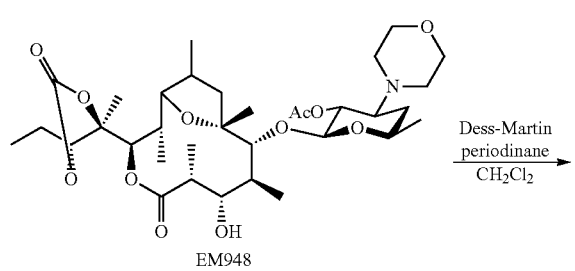

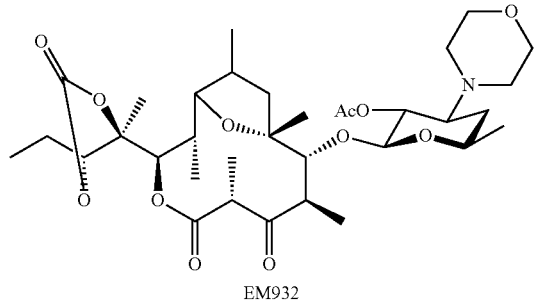

Under $N_2$ atmosphere, to a solution (4.560 mL) of EM948 (152.5 mg, 0.228 mmol) obtained in the below-mentioned Example 48 in $CH_2Cl_2$ was added Dess-Martin periodinane (165.8 mg, 0.391 mmol), and the mixture was stirred for 2 hr. After stirring, saturated $Na_2S_2O_3$ solution (50.00 mL) was added, and the mixture was extracted with $CHCl_3$. After washing with saturated $Na_2S_2O_3$ solution, saturated $NaHCO_3$ solution and brine, the organic layer was dried over $Na_2SO_4$. The residue was filtrated, and the filtrate was concentrated to give a crude product (160.0 mg). The obtained crude product was separated and purified by flash column chromatography ($CHCl_3$:MeOH:$NH_4OH$ aq=100:1:0.1) to give EM932 (151.1 mg, 90%) as a white powder.

EM932

HR-MS m/z: 668.3642 [M+H]+, Calcd for $C_{34}H_{54}NO_{12}$: 668.3646 [M+H]

Example 34

Synthesis of de(3'-N-methyl)-3'-N-ethyl-9-dihydro-pseudoerythromycin A 6,9-epoxide (EM933)

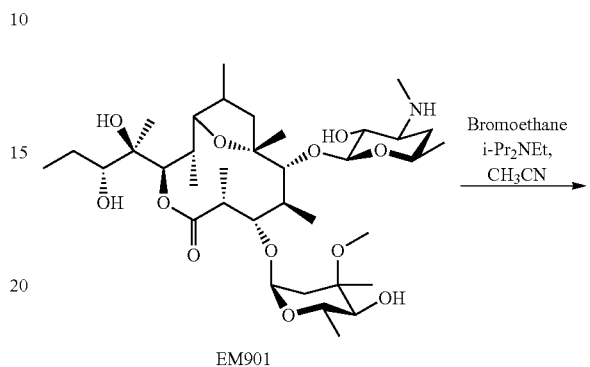

Under $N_2$ atmosphere, to a solution (586.0 µl) of EM901 (41.20 mg, 0.0586 mmol) in $CH_3CN$ were added i-$Pr_2NEt$ (102.1 µl, 0.5860 mmol) and bromoethane (43.70 µl, 0.5860 mmol), and the mixture was stirred at room temperature for 22 hr. After stirring, the mixture was heated to 50° C. and stirred for 134 hr. Furthermore, i-$Pr_2NEt$ (102.1 µl, 0.5860 mmol) and bromoethane (43.70 µl, 0.5860 mmol) were added, and the mixture was stirred at 50° C. for 14 hr. After stirring, saturated $Na_2S_2O_3$ solution (40.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (50.00 mg). The obtained crude product was separated and purified by flash column chromatography ($CHCl_3$:MeOH:$NH_4OH$ aq=100:1:0.1) to give EM933 (42.40 mg, 86%) as a white powder.

EM933
HR-MS m/z: 732.4911 [M+H]$^+$, Calcd for $C_{38}H_{70}NO_{12}$: 732.4898 [M+H]

Example 35

Synthesis of de(3-O-cladinosyl)-de(3'-N-methyl)-9-dihydro-pseudoerythromycin A 6,9-epoxide (EM934)

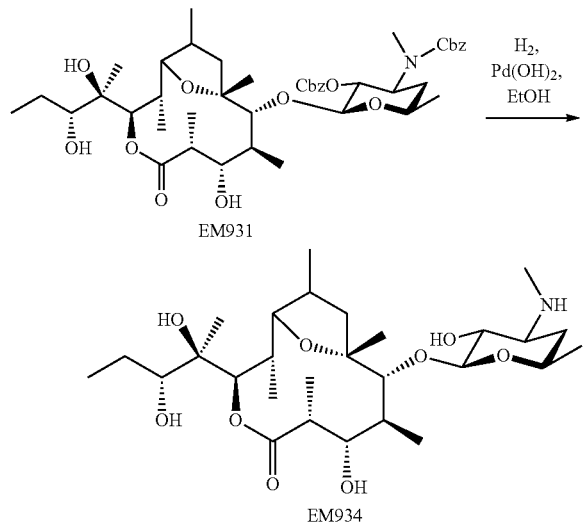

Under N$_2$ atmosphere, to EM931 (108.4 mg, 0.1330 mmol) were added Pd(OH)$_2$ (21.70 mg) and EtOH (2.660 mL), and the mixture was stirred under H$_2$ atmosphere at room temperature for 1 hr. After stirring, the mixture was filtrated, and the filtrate was concentrated to give a crude product (150.1 mg). The obtained crude product was separated and purified by flash column chromatography (CHCl$_3$:MeOH:NH$_4$OH aq=30:1:0.1-10:1:0.1) to give EM934 (70.30 mg, 97%) as a white powder.
EM934
HR-MS m/z: 546.3622 [M+H]$^+$, Calcd for $C_{28}H_{54}NO_9$: 546.3642 [M+H]

Example 36

Synthesis of de(3-O-cladinosyl)-9-dihydro-3-keto-de(3'-dimethylamino)-3'-morpholino-pseudoerythromycin A 6,9-epoxide 12,13-carbonate (EM935)

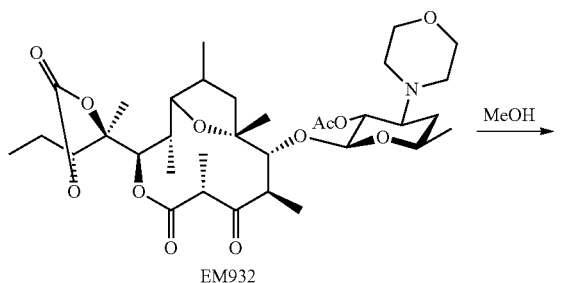

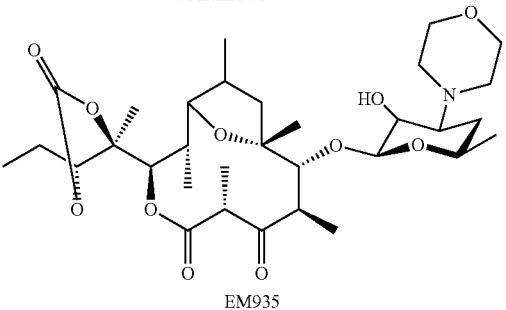

A solution (6.280 mL) of EM932 (104.6 mg, 0.157 mmol) in MeOH was heated to 50° C. and stirred for 68 hr. After stirring, the mixture was concentrated to give a crude product (101.2 mg). The obtained crude product was separated and purified by flash column chromatography (CHCl$_3$:MeOH:NH$_4$OH aq=100:1:0.1) to give EM935 (98.00 mg, 100%) as a white powder.
EM935
HR-MS m/z: 626.3533 [M+H]$^+$, Calcd for $C_{32}H_{52}NO_{11}$: 626.3540 [M+H]

Example 37

Synthesis of de(3'-N-methyl)-2'-O-3'-N-bis(benzyloxycarbonyl)-de(3-O-cladinosyl)-9-dihydro-pseudoerythromycin A 6,9-epoxide 12,13-carbonate (EM936)

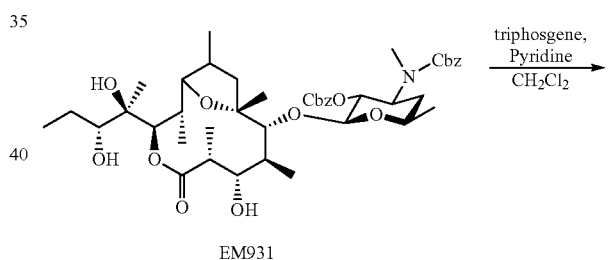

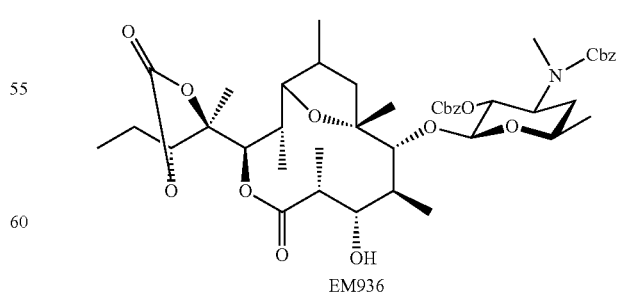

Under N$_2$ atmosphere, a solution (49.80 mL) of EM931 (2.027 g, 2.492 mmol) in CH$_2$Cl$_2$ was cooled to −78° C., pyridine (2.420 mL, 29.90 mmol) was added, a solution (99.70 mL) of triphosgene (1.479 g, 4.984 mmol) in CH$_2$Cl$_2$ was added dropwise, and the mixture was warmed from −78° C. to room temperature and stirred for 0.5 hr. After stirring, saturated NH$_4$Cl solution (400.0 mL) was added, and the mixture was extracted with CH$_2$Cl$_2$. After washing with saturated NaHCO$_3$ solution and brine, the organic layer was dried over Na$_2$SO$_4$. The residue was filtrated, and the filtrate was concentrated to give a crude product (1.900 g). The obtained crude product was separated and purified by flash column chromatography (CHCl$_3$:MeOH:NH$_4$OH aq=100:1:0.1) to give EM936 (1.882 g, 90%) as a white powder.

EM936

HR-MS m/z: 862.4000 [M+Na]$^+$, Calcd for C$_{45}$H$_{61}$NO$_{14}$Na: 862.3990 [M+Na]

Example 38

Synthesis of de(3'-N-methyl)-2'-O-3'-N-bis(benzyloxycarbonyl)-de(3-O-cladinosyl)-9-dihydro-3-keto-pseudoerythromycin A 6,9-epoxide 12,13-carbonate (EM937)

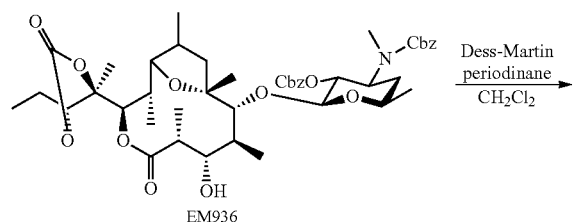

Under N$_2$ atmosphere, to a solution (40.80 mL) of EM936 (1.718 g, 2.047 mmol) in CH$_2$Cl$_2$ was added Dess-Martin periodinane (4.343 g, 10.24 mmol), and the mixture was stirred for 1.5 hr. After stirring, saturated Na$_2$S$_2$O$_3$ solution (300.0 mL) was added, and the mixture was extracted with CHCl$_3$. After washing with saturated Na$_2$S$_2$O$_3$ solution, saturated NaHCO$_3$ solution and brine, the organic layer was dried over Na$_2$SO$_4$. The residue was filtrated, and the filtrate was concentrated to give a crude product (1.700 g). The obtained crude product was separated and purified by flash column chromatography (CHCl$_3$:MeOH:NH$_4$OH aq=50:1:0.1) to give EM937 (1.668 g, 97%) as a white powder.

EM937

HR-MS m/z: 838.4012 [M+H]$^+$, Calcd for C$_{45}$H$_{60}$NO$_{14}$: 838.4014 [M+H]

Example 39

Synthesis of de(3-O-cladinosyl)-9-dihydro-3-keto-de(3'-N-methyl)-pseudoerythromycin A 6,9-epoxide 12,13-carbonate (EM938)

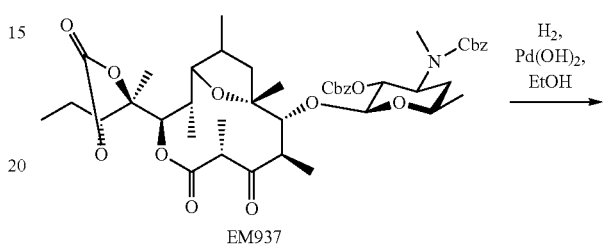

Under N$_2$ atmosphere, to EM937 (1.461 g, 1.745 mmol) were added Pd(OH)$_2$ (292.2 mg) and EtOH (34.90 mL), and the mixture was stirred under H$_2$ atmosphere at room temperature for 3 hr. After stirring, Pd(OH)$_2$ (292.2 mg) was added under N$_2$ atmosphere, and the mixture was stirred under H$_2$ atmosphere at room temperature for 2.5 hr. Furthermore, after stirring, Pd(OH)$_2$ (146.1 mg) was added under N$_2$ atmosphere, and the mixture was stirred under H$_2$ atmosphere at room temperature for 1 hr. The mixture was filtrated, and the filtrate was concentrated to give a crude product (1.302 g). The obtained crude product was separated and purified by flash column chromatography (CHCl$_3$:MeOH:NH$_4$OH aq=50:1:0.1-30:1:0.1) to give EM938 (967.3 mg, 97%) as a white powder.

EM938
HR-MS m/z: 570.3307 [M+H]⁺, Calcd for $C_{29}H_{48}NO_{10}$: 570.3278 [M+H]

Example 40

Synthesis of de(3'-N-methyl)-3'-N-(p-chlorobenzyl)-de(3-O-cladinosyl)-9-dihydro-3-keto-pseudoerythromycin A 6,9-epoxide 12,13-carbonate (EM939)

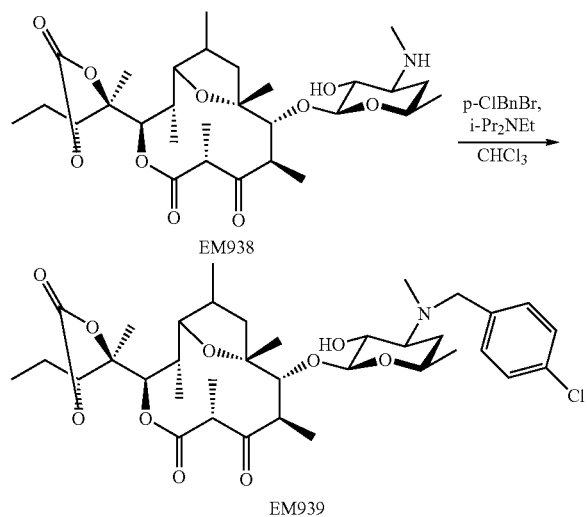

To a solution (5.330 mL) of EM938 (303.4 mg, 0.533 mmol) in CHCl₃ were added i-Pr₂NEt (928.4 μl, 5.330 mmol) and p-ClBnBr (1.095 g, 5.330 mmol), and the mixture was stirred under N₂ atmosphere at room temperature for 2 hr. After stirring, saturated Na₂S₂O₃ solution (50.00 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (350.1 mg). The obtained crude product was separated and purified by flash column chromatography (CHCl₃:MeOH:NH₄OH aq=100:1:0.1) to give EM939 (342.5 mg, 93%) as a white powder.

EM939
HR-MS m/z: 694.3353 [M+H]⁺, Calcd for $C_{36}H_{53}NO_{10}Cl$: 694.3358 [M+H]

Example 41

Synthesis of 9-dihydro-de(3'-N-methyl)-3'-N-1-propyl-pseudoerythromycin A 6,9-epoxide (EM940)

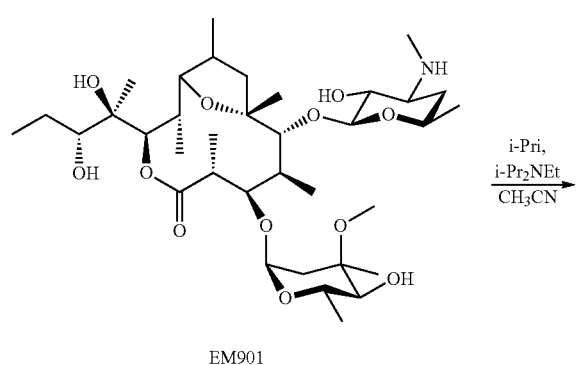

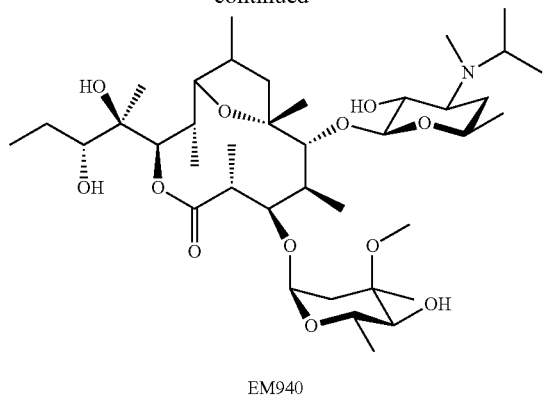

EM940

Under N₂ atmosphere, to a solution (564.0 μl) of EM901 (39.70 mg, 0.0564 mmol) in CH₃CN were added i-Pr₂NEt (98.20 μl, 0.5840 mmol) and i-PrI (2-iodopropane: 56.30 μl, 0.5640 mmol), and the mixture was stirred at 50° C. for 134 hr. After stirring, i-Pr₂NEt (98.20 μl, 0.5840 mmol) and i-PrI (56.30 μl, 0.5640 mmol) were added, and the mixture was stirred at 50° C. for 26.5 hr. Furthermore, i-Pr₂NEt (196.4 μl, 1.128 mmol) and i-PrI (112.6 μl, 1.128 mmol) were added, and the mixture was stirred at 50° C. for 97.5 hr. After stirring, saturated Na₂S₂O₃ solution (30.00 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (50.00 mg). The obtained crude product was separated and purified by flash column chromatography (CHCl₃:MeOH:NH₄OH aq=100:1:0.1-50:1:0.1) to give EM940 (16.10 mg, 38%) as a white powder.

EM940
HR-MS m/z: 746.5043 [M+H]⁺, Calcd for $C_{39}H_{72}NO_{12}$: 746.5055 [M+H]

Example 42

Synthesis of de(3-O-cladinosyl)-9-dihydro-bis-de(3'-N-methyl)-pseudoerythromycin A 6,9-epoxide (EM941)

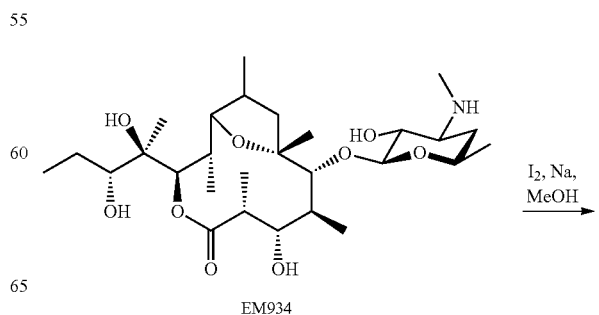

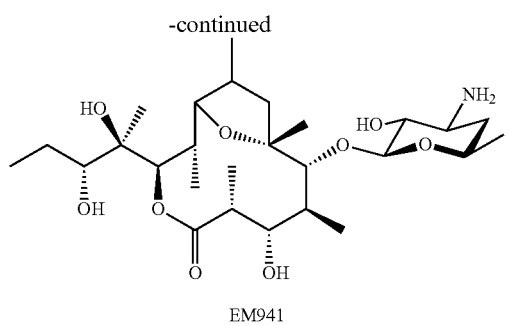

EM941

A solution (161.1 mL) of Na (222.2 mg, 9.666 mmol) in MeOH was cooled to 0° C., EM934 (878.6 mg, 1.611 mmol) and I$_2$ (2.044 g, 8.055 mmol) were added under N$_2$ atmosphere, and the mixture was stirred at 0° C. for 1 hr. After stirring, Na$_2$S$_2$O$_3$ (6.000 g) was added, and the mixture was warmed to room temperature. The reaction mixture was extracted with CHCl$_3$. After washing with mixed solution of brine and NH$_4$OH, the organic layer was dried over Na$_2$SO$_4$. The residue was filtrated, and the filtrate was concentrated to give a crude product (870.2 mg). The obtained crude product was separated and purified by flash column chromatography (CHCl$_3$:MeOH:NH$_4$OH aq=30:1:0.1-10:1:0.1) to give EM941 (549.7 mg, 64%) as a white powder.

EM941

HR-MS m/z: 532.3509 [M+H]$^+$, Calcd for C$_{27}$H$_{50}$NO$_9$: 532.3486 [M+H]

Example 43

Synthesis of de(3'-N-methyl)-2'-O-3'-N-bis(benzyloxycarbonyl)-de(3-O-cladinosyl)-9-dihydro-pseudoerythromycin A 6,9-epoxide 12,13-isopropylidene Acetal (EM942)

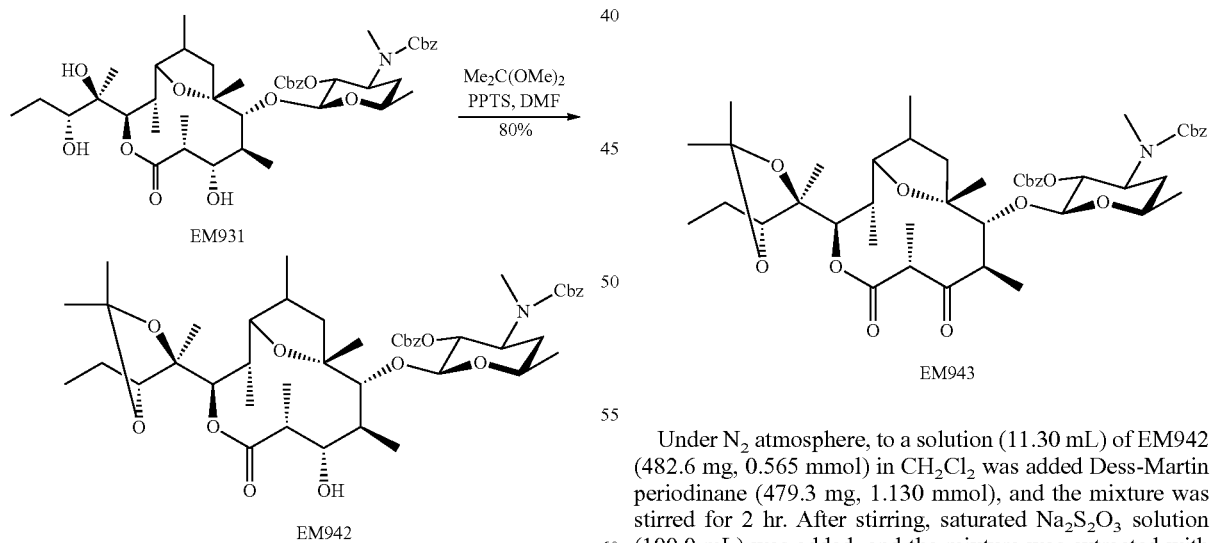

To a solution (8.434 mL) of EM931 (686.5 mg, 0.843 mmol) in DMF (dimethylformamide) were added PPTS (pyridinium p-toluenesulfonate: 2.120 g, 8.434 mmol), Me$_2$C(OMe)$_2$ (acetone dimethyl acetal: 5.497 mL, 44.70 mmol), and the mixture was stirred under N$_2$ atmosphere at room temperature for 21 hr. After stirring, saturated NaHCO$_3$ solution (100.0 mL) was added, and the mixture was extracted with CHCl$_3$. After washing with H$_2$O, the organic layer was dried over Na$_2$SO$_4$, the residue was filtrated, and the filtrate was concentrated. The concentrate was dissolved in hexane:AcOEt=1:1, and the solution was washed with H$_2$O. The organic layer was dried over Na$_2$SO$_4$. The residue was filtrated, and the filtrate was concentrated to give a crude product (700.2 mg). The obtained crude product was separated and purified by flash column chromatography (CHCl$_3$:MeOH:NH$_4$OH aq=100:1:0.1) to give EM942 (697.6 mg, 97%) as a white powder.

EM942

HR-MS m/z: 876.4503 [M+Na]$^+$, Calcd for C$_{47}$H$_{67}$NO$_{13}$Na: 876.4510 [M+Na]

Example 44

Synthesis of de(3'-N-methyl)-2'-O-3'-N-bis(benzyloxycarbonyl)-de(3-O-cladinosyl)-9-dihydro-3-keto-pseudoerythromycin A 6,9-epoxide 12,13-isopropylidene Acetal (EM943)

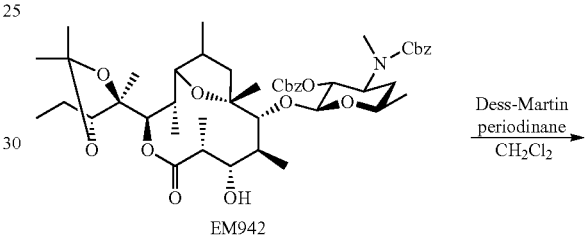

EM943

Under N$_2$ atmosphere, to a solution (11.30 mL) of EM942 (482.6 mg, 0.565 mmol) in CH$_2$Cl$_2$ was added Dess-Martin periodinane (479.3 mg, 1.130 mmol), and the mixture was stirred for 2 hr. After stirring, saturated Na$_2$S$_2$O$_3$ solution (100.0 mL) was added, and the mixture was extracted with CHCl$_3$. After washing with saturated Na$_2$S$_2$O$_3$ solution, saturated NaHCO$_3$ solution and brine, the organic layer was dried over Na$_2$SO$_4$. The residue was filtrated, and the filtrate was concentrated to give a crude product (1.700 g). The obtained crude product was separated and purified by flash column chromatography (CHCl$_3$:MeOH:NH$_4$OH aq=100:1:0.1) to give EM943 (480.0 mg, 100%) as a white powder.

EM943

HR-MS m/z: 874.4383 [M+Na]+, Calcd for $C_{47}H_{65}NO_{13}Na$: 874.4354 [M+Na]

Example 45

Synthesis of de(3-O-cladinosyl)-9-dihydro-3-keto-de(3'-N-methyl)-pseudoerythromycin A 6,9-epoxide 12,13-isopropylidene acetal (EM944)

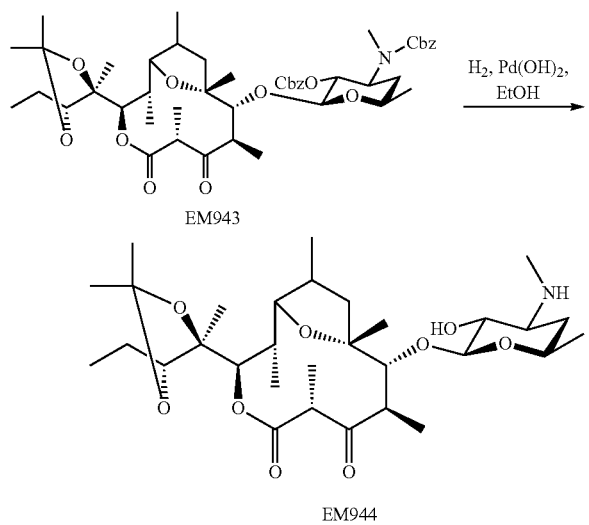

Under $N_2$ atmosphere, to EM943 (406.8 mg, 0.478 mmol) were added Pd(OH)$_2$ (81.4 mg) and EtOH (9.56 mL), and the mixture was stirred under $H_2$ atmosphere at room temperature for 2 hr. The mixture was filtrated, and the filtrate was concentrated to give a crude product (300.0 mg). The obtained crude product was separated and purified by flash column chromatography (CHCl$_3$:MeOH:NH$_4$OH aq=50:1:0.1-10:1:0.1) to give EM944 (275.6 mg, 99%) as a white powder.

EM944

HR-MS m/z: 584.3795 [M+H]+, Calcd for $C_{31}H_{54}NO_9$: 584.3799 [M+H]

Example 46

Synthesis of de(3-O-cladinosyl)-9-dihydro-de(3'-dimethylamino)-3'-morpholino-pseudoerythromycin A 6,9-epoxide 12,13-carbonate (EM946)

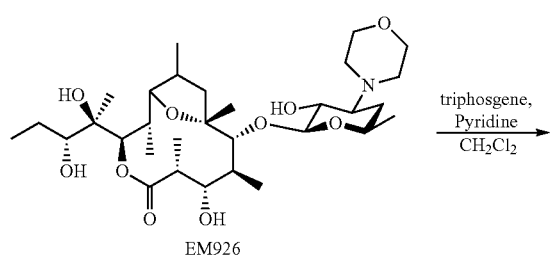

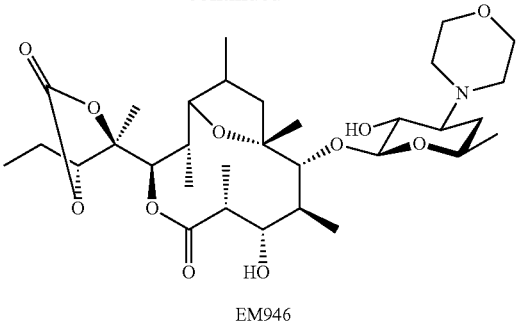

Under $N_2$ atmosphere, a solution (8.620 mL) of EM926 (259.3 mg, 0.431 mmol) in CH$_2$Cl$_2$ was cooled to −78° C., pyridine (418.3 μl, 5.172 mmol) was added, a solution (17.24 mL) of triphosgene (255.8 mg, 0.862 mmol) in CH$_2$Cl$_2$ was added dropwise, and the mixture was warmed from −78° C. to room temperature and stirred for 1 hr. After stirring, saturated NH$_4$Cl solution (100.0 mL) was added, and the mixture was extracted with CH$_2$Cl$_2$. After washing with saturated NaHCO$_3$ solution and brine, the organic layer was dried over Na$_2$SO$_4$. The residue was filtrated, and the filtrate was concentrated to give a crude product (285.3 mg). The obtained crude product was separated and purified by flash column chromatography (CHCl$_3$:MeOH:NH$_4$OH aq=100:1:0.1-50:1:0.1) to give EM946 (265.7 mg, 98%) as a white powder.

EM946

HR-MS m/z: 628.3669 [M+H]+, Calcd for $C_{32}H_{54}NO_{11}$: 628.3697 [M+H]

Example 47

Synthesis of de(3'-N-methyl)-3'-N-(p-chlorobenzyl)-de(3-O-cladinosyl)-9-dihydro-3-keto-pseudoerythromycin A 6,9-epoxide 12,13-isopropylidene Acetal (EM947)

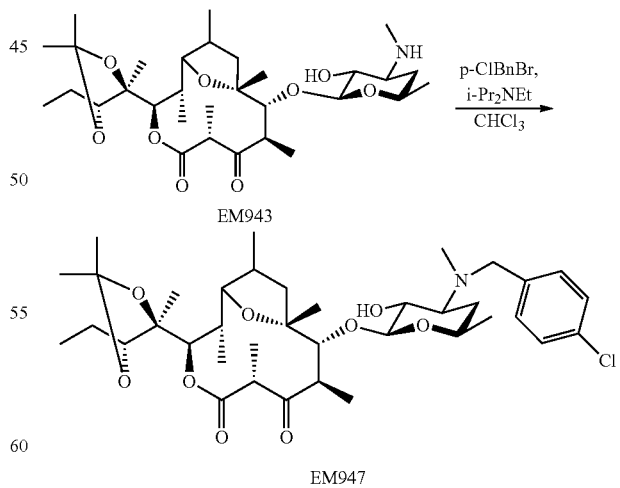

To a solution (3.960 mL) of EM943 (230.9 mg, 0.396 mmol) in CHCl$_3$ were added i-Pr$_2$NEt (689.8 μl, 3.960 mmol) and p-ClBnBr (813.7 mg, 3.960 mmol), and the mixture was stirred under $N_2$ atmosphere at room temperature for 2 hr.

After stirring, saturated Na₂S₂O₃ solution (30.00 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (279.1 mg). The obtained crude product was separated and purified by flash column chromatography (CHCl₃:MeOH:NH₄OH aq=100:1:0.1-50:1:0.1) to give EM947 (250.0 mg, 89%) as a white powder.

EM947

HR-MS m/z: 708.3847 [M+H]⁺, Calcd for $C_{38}H_{59}NO_9Cl$: 708.3878 [M+H]

Example 48

Synthesis of 2'-O-acetyl-de(3-O-cladinosyl)-9-dihydro-de(3'-dimethylamino)-3'-morpholino-pseudo-erythromycin A 6,9-epoxide 12,13-carbonate (EM948)

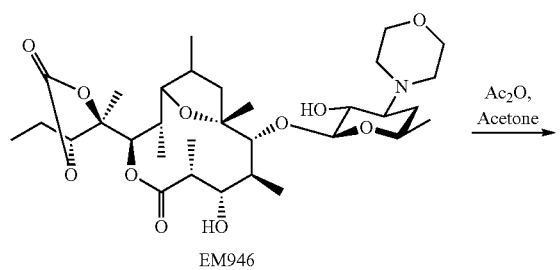

EM946

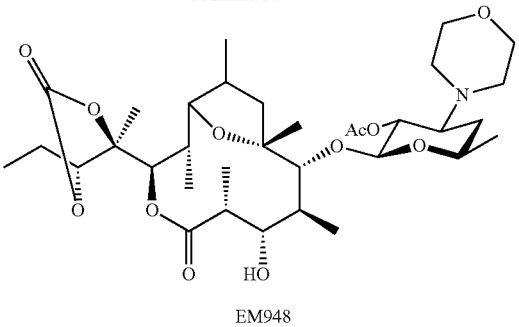

EM948

Under N₂ atmosphere, to a solution (3.340 mL) of EM946 (209.7 mg, 0.334 mmol) in acetone was added Ac₂O (189.0 μl, 2.004 mmol), and the mixture was stirred for 2 hr. Furthermore, after stirring, Ac₂O (189.0 μl, 2.004 mmol) was added, and the mixture was stirred for 4 hr. After stirring, saturated NaHCO₃ solution (100.0 mL) was added, and the mixture was extracted with CHCl₃. After washing with saturated NaHCO₃ solution and brine, the organic layer was dried over Na₂SO₄. The residue was filtrated, and the filtrate was concentrated to give a crude product (210.1 mg). The obtained crude product was separated and purified by flash column chromatography (CHCl₃:MeOH:NH₄OH aq=50:1: 0.1) to give EM948 (202.9 mg, 91%) as a white powder.

HR-MS m/z: 670.3809 [M+H]⁺, Calcd for $C_{34}H_{56}NO_{12}$: 670.3803 [M+H]

Example 49

Synthesis of de(3'-N-methyl)-3'-N-(p-chlorobenzyl)-de(3-O-cladinosyl)-9-dihydro-3-keto-pseudoerythromycin A 6,9-epoxide (EM949)

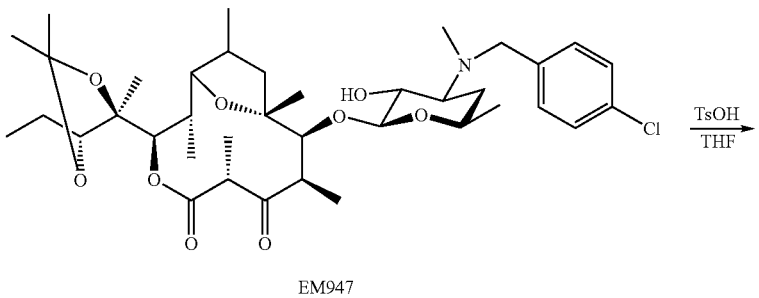

EM947

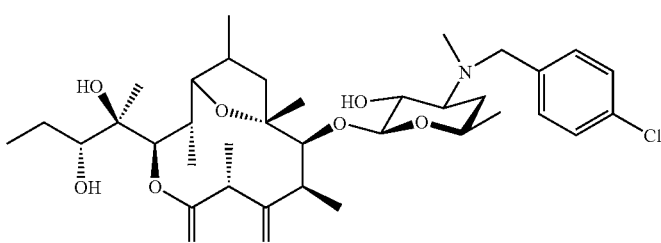

EM949

Under $N_2$ atmosphere, to a solution (2.120 mL) of EM947 (75.3 mg, 0.106 mmol) in THF (tetrahydrofuran) was added TsOH (p-toluenesulfonic acid: 41.30 mg, 0.217 mmol), and the mixture was stirred for 1 hr. After stirring, TsOH (41.30 mg, 0.217 mmol) was added, and the mixture was stirred for 4 hr. Furthermore, TsOH (201.4 mg, 1.059 mmol) was added, and the mixture was stirred for 12 hr. After stirring, saturated $NaHCO_3$ solution (20.00 mL) was added, and the mixture was extracted with $CHCl_3$. After washing with brine, the organic layer was dried over $Na_2SO_4$. The residue was filtrated, and the filtrate was concentrated to give a crude product (80.12 mg). The obtained crude product was separated and purified by flash column chromatography ($CHCl_3$:MeOH:$NH_4OH$ aq=100:1:0.1) to give EM949 (43.2 mg, 61%) as a white powder.

EM949

HR-MS m/z: 690.3353 [M+Na]$^+$, Calcd for $C_{35}H_{54}NO_9ClNa$: 690.3385 [M+Na]

Example 50

Synthesis of de(3-O-cladinosyl)-9-dihydro-de(3'-dimethylamino)-3'-morpholino-pseudoerythromycin A 6,9-epoxide 12,13-isopropylidene Acetal (EM950)

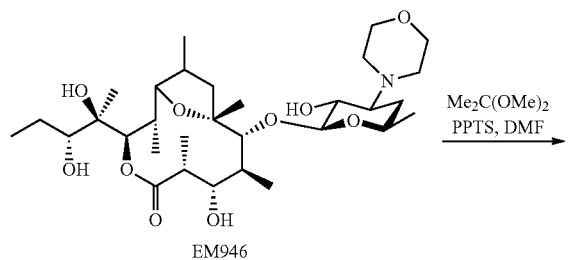

EM946

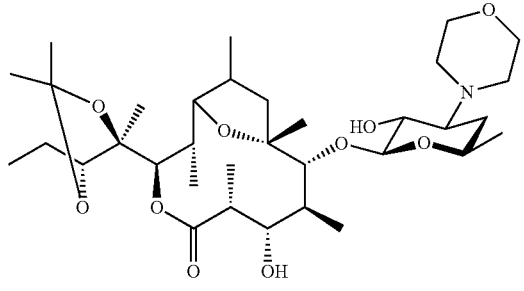

EM950

To a solution (3.910 mL) of EM926 (235.3 mg, 0.391 mmol) in DMF were added PPTS (982.0 mg, 3.910 mmol) and $Me_2C(OMe)_2$ (2.550 mL, 20.72 mmol), and the mixture was stirred under $N_2$ atmosphere at room temperature for 5 hr. After stirring, saturated $NaHCO_3$ solution (30.00 mL) was added, and the mixture was extracted with $CHCl_3$. The organic layer was dried over $Na_2SO_4$, the residue was filtrated, and the filtrate was concentrated. The concentrate was dissolved in hexane:AcOEt=1:1, and the solution was washed with $H_2O$. The organic layer was dried over $Na_2SO_4$. The residue was filtrated, and the filtrate was concentrated to give a crude product (250.2 mg). The obtained crude product was separated and purified by flash column chromatography ($CHCl_3$:MeOH:$NH_4OH$ aq=100:1:0.1-50:1:0.1) to give EM950 (236.6 mg, 94%) as a white powder.

EM950

HR-MS m/z: 642.4221 [M+H]$^+$, Calcd for $C_{34}H_{60}NO_{10}$: 642.4217 [M+Na]

Example 51

Synthesis of 2'-O-acetyl-de(3-O-cladinosyl)-9-dihydro-de(3'-dimethylamino)-3'-morpholino-pseudoerythromycin A 6,9-epoxide 12,13-isopropylidene Acetal (EM951)

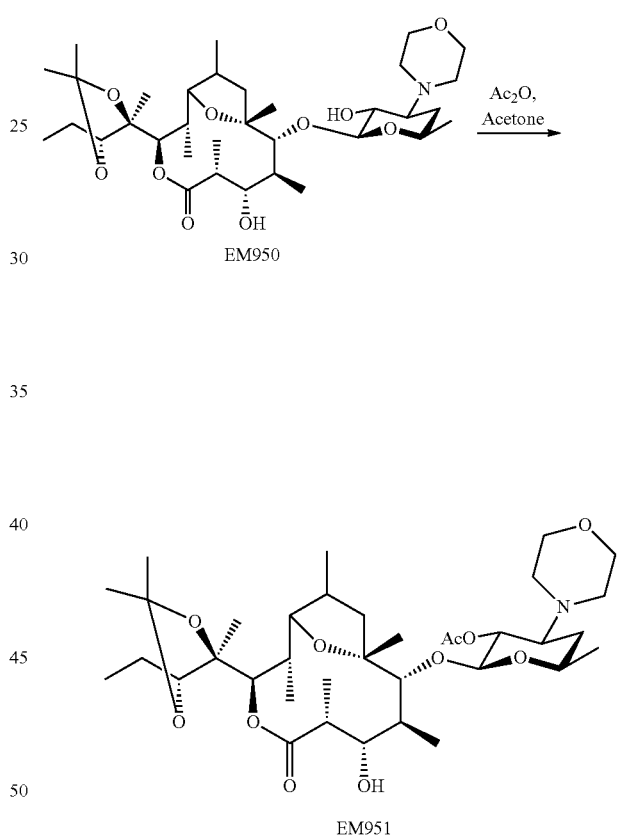

Under $N_2$ atmosphere, to a solution (2.820 mL) of EM950 (181.1 mg, 0.282 mmol) in acetone was added $Ac_2O$ (79.80 μl, 0.846 mmol), and the mixture was stirred for 2 hr. Furthermore, $Ac_2O$ (425.6 μl, 4.512 mmol) was added, and the mixture was stirred for 1 hr. After stirring, saturated $NaHCO_3$ solution (25.00 mL) was added, and the mixture was extracted with $CHCl_3$. After washing with brine, the organic layer was dried over $Na_2SO_4$. The residue was filtrated, and the filtrate was concentrated to give a crude product (210.1 mg). The obtained crude product was separated and purified by flash column chromatography ($CHCl_3$:MeOH:$NH_4OH$ aq=50:1:0.1) to give EM951 (192.0 mg, 10%) as a white powder.

EM951

HR-MS m/z: 684.4318 [M+H]$^+$, Calcd for $C_{36}H_{62}NO_{11}$: 684.4323 [M+H]

Example 52

Synthesis of 2'-O-acetyl-de(3-O-cladinosyl)-9-dihydro-3-keto-de(3'-dimethylamino)-3'-morpholino-pseudoerythromycin A 6,9-epoxide 12,13-isopropylidene Acetal (EM952)

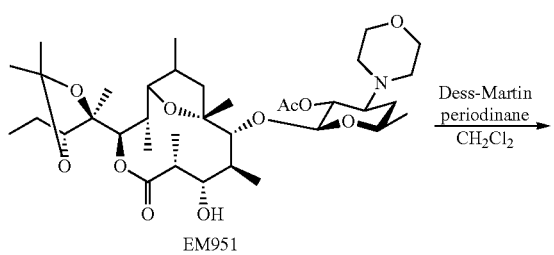

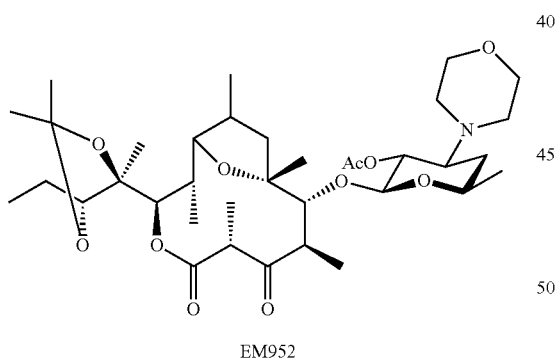

Under $N_2$ atmosphere, to a solution (3.900 mL) of EM951 (132.3 mg, 0.194 mmol) in $CH_2Cl_2$ was added Dess-Martin periodinane (164.4 mg, 0.388 mmol), and the mixture was stirred for 1 hr. After stirring, saturated $Na_2S_2O_3$ solution (25.00 mL) was added, and the mixture was extracted with $CHCl_3$. After washing with saturated $Na_2S_2O_3$ solution, saturated $NaHCO_3$ solution and brine, the organic layer was dried over $Na_2SO_4$. The residue was filtrated, and the filtrate was concentrated to give a crude product (151.0 mg). The obtained crude product was separated and purified by flash column chromatography ($CHCl_3$:MeOH:$NH_4OH$ aq=100:1:0.1-50:1:0.1) to give EM952 (121.6 mg, 92%) as a white powder.

EM952

HR-MS m/z: 682.4163 [M+H]$^+$, Calcd for $C_{36}H_{60}NO_{11}$: 682.4166 [M+H]

Example 53

Synthesis of de(3-O-cladinosyl)-9-dihydro-3-keto-de(3'-dimethylamino)-3'-morpholino-pseudoerythromycin A 6,9-epoxide 12,13-isopropylidene Acetal (EM953)

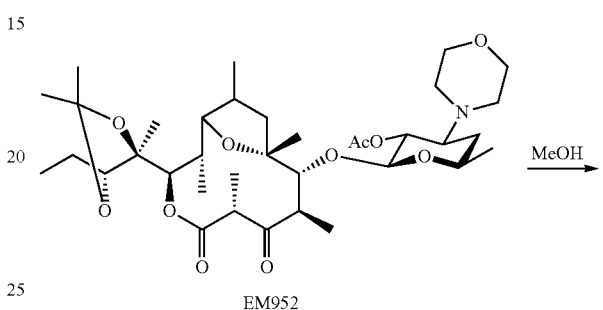

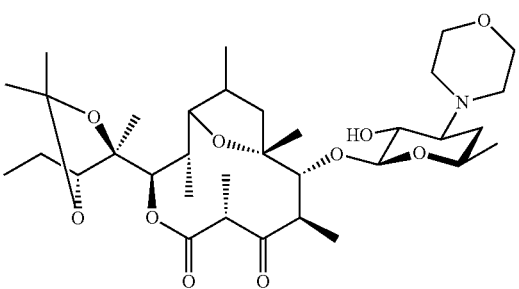

A solution (5.440 mL) of EM952 (92.4 mg, 0.136 mmol) in MeOH was heated to 50° C. and stirred for 36 hr. After stirring, the solution was concentrated to give a crude product (101.2 mg). The obtained crude product was separated and purified by flash column chromatography ($CHCl_3$:MeOH:$NH_4OH$ aq=100:1:0.1-50:1:0.1) to give EM953 (85.50 mg, 98%) as a white powder.

EM953

HR-MS m/z: 640.4053 [M+H]⁺, Calcd for $C_{34}H_{58}NO_{10}$: 640.4061 [M+H]

Example 54

Synthesis of de(3-O-cladinosyl)-9-dihydro-3-keto-de(3'-dimethylamino)-3'-morpholino-pseudoerythromycin A 6,9-epoxide (EM954)

EM954

HR-MS m/z: 600.3749 [M+H]⁺, Calcd for $C_{31}H_{54}NO_{10}$: 600.3748 [M+Na]

Example 55

Synthesis of de(3'-dimethylamino)-3'-piperidino-9-dihydro-pseudoerythromycin A 6,9-epoxide (EM955)

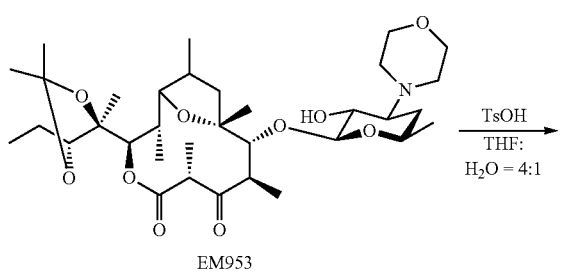

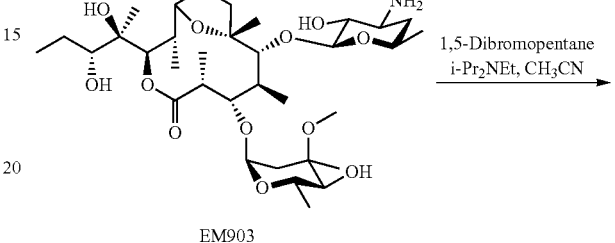

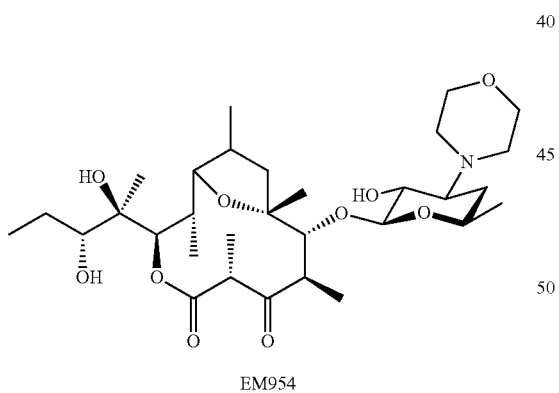

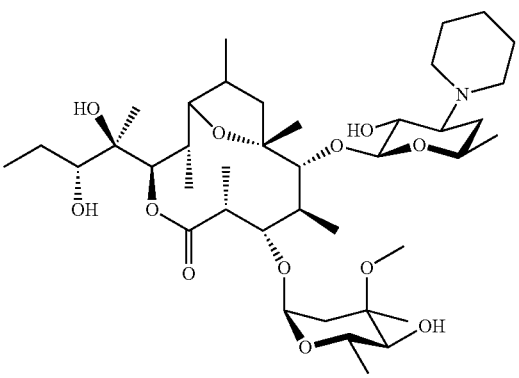

Under N₂ atmosphere, to a mixed solution (1.770 mL) of EM953 (56.6 mg, 0.0885 mmol) in THF and H₂O (4:1) was added TsOH (33.70 mg, 0.177 mmol), and the mixture was stirred for 28 hr. After stirring, saturated NaHCO₃ solution (10.00 mL) was added, and the mixture was extracted with CHCl₃. After washing with brine, the organic layer was dried over Na₂SO₄. The residue was filtrated, and the filtrate was concentrated to give a crude product (60.12 mg). The obtained crude product was separated and purified by flash column chromatography (CHCl₃:MeOH:NH₄OH aq=50:1:0.1) to give EM954 (44.9 mg, 85%) as a white powder.

Under N₂ atmosphere, to a solution (31.80 mL) of EM903 (109.5 mg, 0.159 mmol) in CH₃CN were added i-Pr₂NEt (554.0 μl, 3.180 mmol) and 1,5-dibromopentane (433.0 μl, 3.180 mmol), and the mixture was stirred at 80° C. for 0.5 hr. After stirring, i-Pr₂NEt (1.300 mL, 9.540 mmol) and 1,5-dibromopentane (1.660 mL, 9.540 mmol) were added, and the mixture was stirred at 80° C. for 21 hr. After stirring, saturated Na₂S₂O₃ solution (100.0 mL) was added, and the mixture was extracted with CHCl₃. After washing with saturated Na₂S₂O₃ solution, saturated NH₄Cl solution and brine, the organic layer was dried over Na₂SO₄. The residue was filtrated, and the filtrate was concentrated to give a crude product (102.7 mg). The obtained crude product was separated and purified by flash column chromatography (CHCl₃:MeOH:NH₄OH aq=50:1:0.1) to give EM955 (98.20 mg, 82%) as a white powder.

EM955

HR-MS m/z: 758.5054 [M+H]+, Calcd for $C_{40}H_{72}NO_{12}$: 758.5055 [M+H]

Example 56

Synthesis of de(3'-dimethylamino)-3'-pyrroridino-9-dihydro-pseudoerythromycin A 6,9-epoxide (EM956)

EM956

HR-MS m/z: 744.4893 [M+H]+, Calcd for $C_{39}H_{70}NO_{12}$: 744.4898 [M+H]

Example 57

Synthesis of de(3'-N-methyl)-3'-N-allyl-9-dihydro-pseudoerythromycin A 6,9-epoxide (EM957)

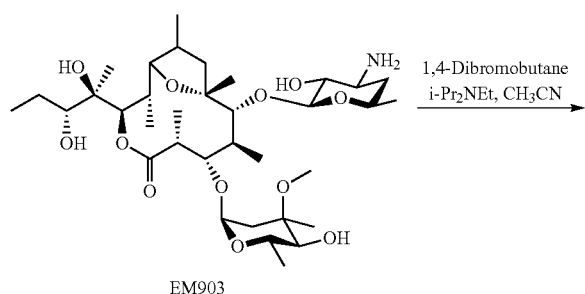
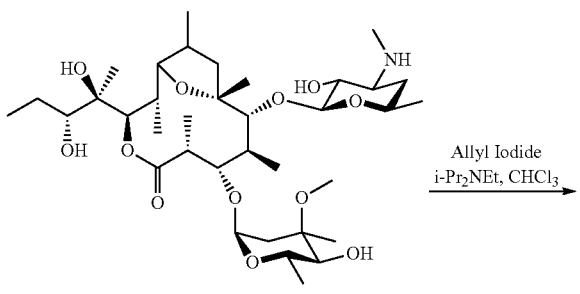
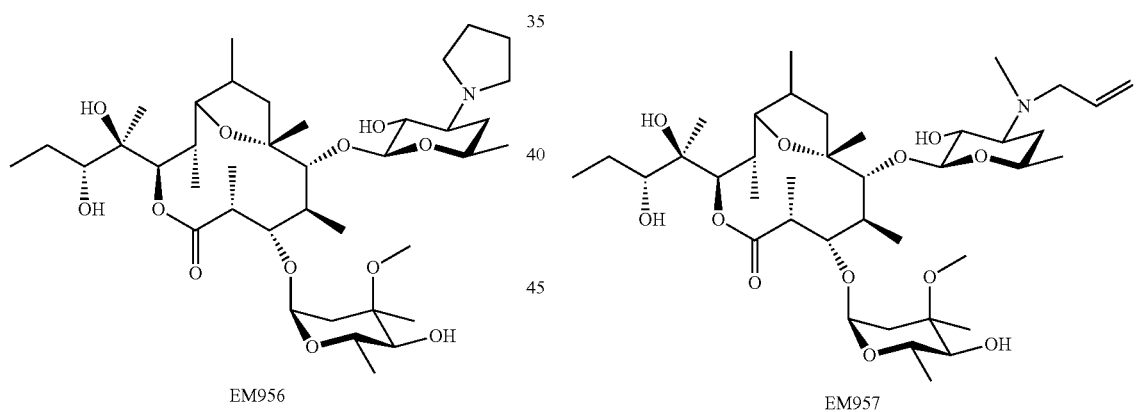

Under $N_2$ atmosphere, to a solution (32.80 mL) of EM903 (112.9 mg, 0.164 mmol) in $CH_3CN$ were added i-$Pr_2NEt$ (571.3 μl, 3.280 mmol) and 1,4-dibromobutane (388.7 μl, 3.280 mmol), and the mixture was stirred at 80° C. for 2 hr. After stirring, i-$Pr_2NEt$ (1.710 mL, 9.840 mmol) and 1,4-dibromobutane (1.170 mL, 9.840 mmol) were added, and the mixture was stirred at 80° C. for 22 hr. After stirring, saturated $Na_2S_2O_3$ solution (100.0 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (100.7 mg). The obtained crude product was separated and purified by flash column chromatography ($CHCl_3$:MeOH:$NH_4OH$ aq=50:1:0.1-30:1:0.1) to give EM956 (75.10 mg, 62%) as a white powder.

Under $N_2$ atmosphere, to a solution (1.510 ml) of EM901 (106.4 mg, 0.151 mmol) in $CHCl_3$ were added i-$Pr_2NEt$ (263.0 μl, 1.510 mmol) and allyl iodide (137.1 μl, 1.510 mmol), and the mixture was stirred for 3 hr. After stirring, i-$Pr_2NEt$ (263.0 μl, 1.510 mmol) and allyl iodide (137.1 μl, 1.510 mmol) were added, and the mixture was stirred for 3 hr. After stirring, saturated $Na_2S_2O_3$ solution (10.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (80.50 mg). The obtained crude product was separated and purified by flash column chromatography ($CHCl_3$:MeOH:$NH_4OH$ aq=50:1:0.1-30:1:0.1) to give EM957 (60.50 mg, 54%) as a white powder.

EM957
HR-MS m/z: 744.4911 [M+H]+, Calcd for $C_{39}H_{70}NO_{12}$: 744.4898 [M+H]

Example 58

Synthesis of de(3'-N-methyl)-9-dihydro-3'-N-(p-methylbenzyl)-pseudoerythromycin A 6,9-epoxide (EM958)

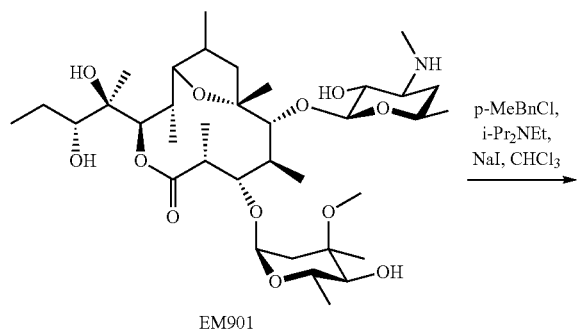

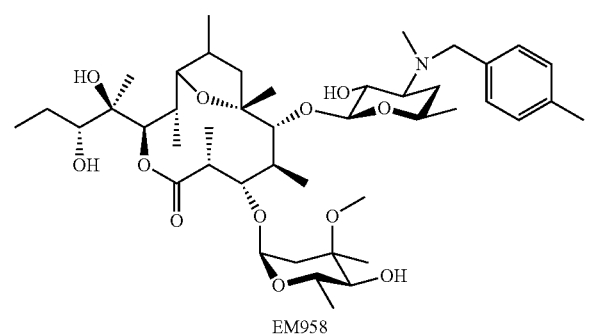

EM958
HR-MS m/z: 808.5217 [M+H]+, Calcd for $C_{44}H_{74}NO_{12}$: 808.5211 [M+H]

Example 59

Synthesis of de(3'-N-methyl)-9-dihydro-3'-N-(p-methoxybenzyl)-pseudoerythromycin A 6,9-epoxide (EM959)

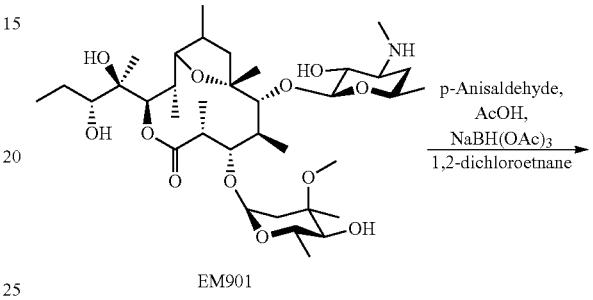

Under $N_2$ atmosphere, to a solution (680.0 μl) of EM901 (47.80 mg, 0.0680 mmol) in $CHCl_3$ were added i-$Pr_2NEt$ (236.9 μl, 1.360 mmol) and p-MeBnCl (178.7 μl, 1.360 mmol), and the mixture was stirred at room temperature for 0.5 hr. After stirring, NaI (203.9 mg, 1.360 mmol) was added, and the mixture was stirred at room temperature for 22 hr. After stirring, saturated $Na_2S_2O_3$ solution (15.00 mL) was added, and the mixture was extracted with $CHCl_3$. After washing with saturated $Na_2S_2O_3$ solution, saturated $NH_4Cl$ solution and brine, the organic layer was dried over $Na_2SO_4$. The residue was filtrated, and the filtrate was concentrated to give a crude product (40.30 mg). The obtained crude product was separated and purified by flash column chromatography ($CHCl_3$:MeOH:$NH_4OH$ aq=100:1:0.1) to give EM958 (24.20 mg, 45%) as a white powder.

Under $N_2$ atmosphere, a solution (3.180 mL) of EM901 (112.1 mg, 0.159 mmol) in 1,2-dichloroethane was cooled to 0° C., p-anisaldehyde (39.50 μl, 0.326 mmol), AcOH (27.30 μl, 0.477 mmol) and NaBH(OAc)$_3$ (101.1 mg, 0.477 mmol) were added, and the mixture was warmed to room temperature and stirred for 2.5 hr. After stirring, saturated $NaHCO_3$ solution (20.00 mL) was added, and the mixture was extracted with $CHCl_3$. After washing with saturated $NaHCO_3$ solution and brine, the organic layer was dried over $Na_2SO_4$. The residue was filtrated, and the filtrate was concentrated to give a crude product (100.0 mg). The obtained crude product was separated and purified by flash column chromatography ($CHCl_3$:MeOH:$NH_4OH$ aq=100:1:0.1-10:1:0.1) to give EM959 (63.40 mg, 48%) as a white powder.

EM959

HR-MS m/z: 824.5173 [M+H]$^+$, Calcd for $C_{44}H_{74}NO_{13}$: 824.5160 [M+H]

Example 60

Synthesis of de(3'-N-methyl)-9-dihydro-3'-N-acetyl-pseudoerythromycin A 6,9-epoxide (EM960)

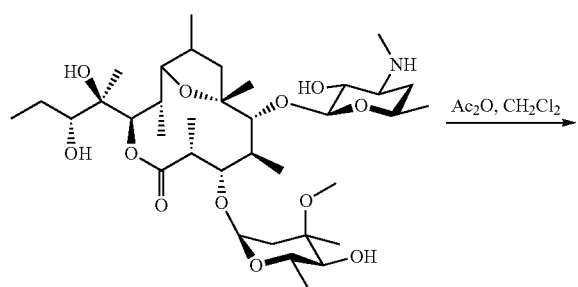

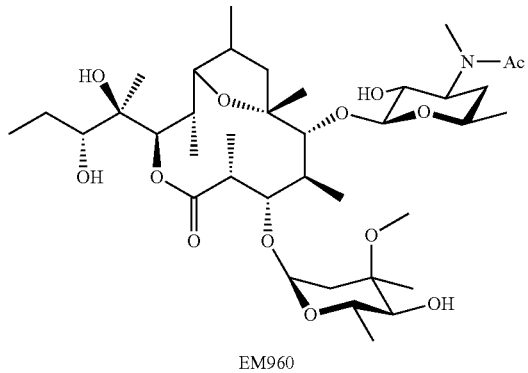

Under N$_2$ atmosphere, a solution (3.540 mL) of EM901 (124.9 mg, 0.177 mmol) in CH$_2$Cl$_2$ was cooled to 0° C., Ac$_2$O (25.10 μl, 0.266 mmol) was added, and the mixture was stirred for 10 min, warmed to room temperature and stirred for 0.5 hr. After stirring, saturated NaHCO$_3$ solution (10.00 mL) was added, and the mixture was extracted with CHCl$_3$. After washing with brine, the organic layer was dried over Na$_2$SO$_4$. The residue was filtrated, and the filtrate was concentrated to give a crude product (140.2 mg). The obtained crude product was separated and purified by flash column chromatography (CHCl$_3$:MeOH:NH$_4$OH aq=50:1:0.1) to give EM960 (132.0 mg, 100%) as a white powder.

EM960

HR-MS m/z: 768.4538 [M+Na]$^+$, Calcd for $C_{38}H_{67}NO_{13}$Na: 768.4510 [M+Na]

Example 61

Synthesis of de(3'-N-methyl)-9-dihydro-3'-N-methanesulfonyl-pseudoerythromycin A 6,9-epoxide (EM961)

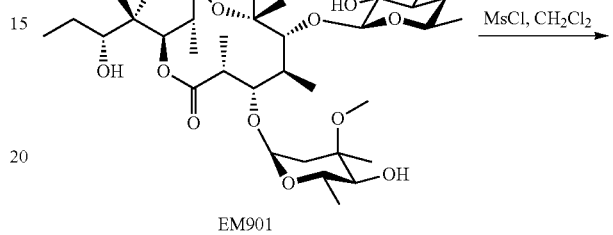

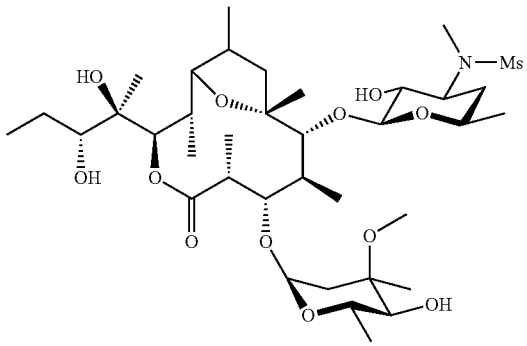

Under N$_2$ atmosphere, a solution (3.040 mL) of EM901 (107.0 mg, 0.152 mmol) in CH$_2$Cl$_2$ was cooled to 0° C., MsCl (23.50 μl, 0.304 mmol) was added, and the mixture was stirred for 0.5 hr, warmed to room temperature and stirred for 1.5 hr. After stirring, MsCl (47.00 μl, 0.608 mmol) was added, and the mixture was stirred for 4 hr. After stirring, saturated NaHCO$_3$ solution (20.00 mL) was added, and the mixture was extracted with CHCl$_3$. After washing with brine, the organic layer was dried over Na$_2$SO$_4$. The residue was filtrated, and the filtrate was concentrated to give a crude product (111.1 mg). The obtained crude product was separated and purified by flash column chromatography (CHCl$_3$: MeOH:NH$_4$OH aq=50:1:0.1) to give EM961 (75.80 mg, 64%) as a white powder.

EM961
HR-MS m/z: 804.4183 [M+Na]+, Calcd for $C_{37}H_{67}NO_{14}SNa$: 804.4180 [M+Na]

Example 62

Synthesis of de(3'-N-methyl)-9-dihydro-3'-N-n-pentyl-pseudoerythromycin A 6,9-epoxide (EM962)

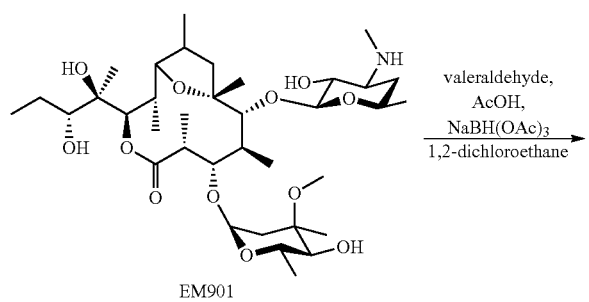

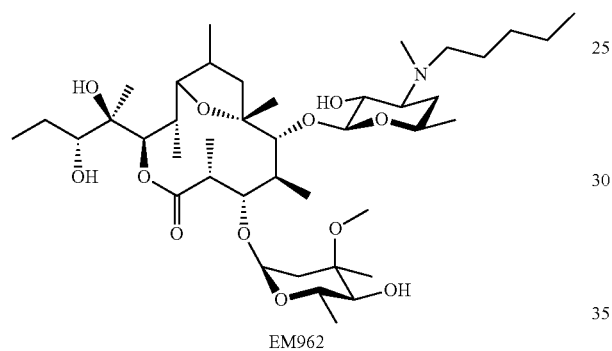

Under $N_2$ atmosphere, a solution (3.780 mL) of EM901 (131.5 mg, 0.189 mmol) in 1,2-dichloroethane was cooled to 0° C., n-valeraldehyde (41.10 μl, 0.387 mmol), AcOH (32.50 μl, 0.567 mmol) and NaBH(OAc)$_3$ (120.2 mg, 0.567 mmol) were added, and the mixture was warmed to room temperature and stirred for 2 hr. After stirring, saturated NaHCO$_3$ solution (20.00 mL) was added, and the mixture was extracted with CHCl$_3$. After washing with brine, the organic layer was dried over-Na$_2$SO$_4$. The residue was filtrated, and the filtrate was concentrated to give a crude product (120.5 mg). The obtained crude product was separated and purified by flash column chromatography (CHCl$_3$: MeOH:NH$_4$OH aq=50:1:0.1) to give EM962 (118.8 mg, 81%) as a white powder.

EM962

HR-MS m/z: 774.5383 [M+H]+, Calcd for $C_{41}H_{76}NO_{12}$: 774.5368 [M+H]

Example 63

Synthesis of de(3'-dimethylamino)-3'-(4'''-N-benzyloxycarbonylpiperazinyl)-9-dihydro-pseudoerythromycin A 6,9-epoxide (EM965)

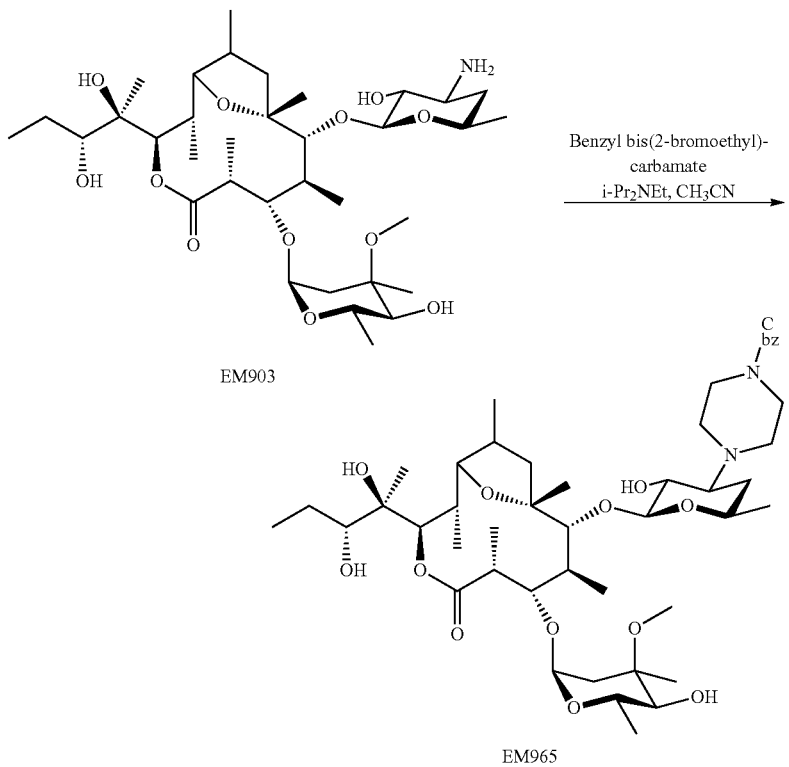

Under $N_2$ atmosphere, to a solution (61.6 mL) of EM903 (213 mg, 0.308 mmol) in $CH_3CN$ were added i-$Pr_2NEt$ (537 μl, 3.08 mmol) and benzyl bis(2-bromoethyl)carbamate (760 mg, 2.08 mmol), and the mixture was stirred at 80° C. for 12 hr. After stirring, saturated $Na_2S_2O_3$ solution (60.0 mL) was added, and the mixture was extracted with $CHCl_3$. After washing with saturated $NH_4Cl$ solution and brine, the organic layer was dried over $Na_2SO_4$. The residue was filtrated, and the filtrate was concentrated to give a crude product (250 mg). The obtained crude product was separated and purified by flash column chromatography ($CHCl_3$:MeOH:30% $NH_4OH$ aq=100:1:0.1) to give EM965 (169 mg, 61%) as a white powder.

IR (KBr) ν $cm^{-1}$; 3469, 2971, 2935, 2883, 1708, 1625, 1455, 1378, 1267, 1166, 1110, 1054, 1022

$^{13}C$ NMR (67.5 MHz, $CDCl_3$) δ (ppm): 177.2 (C-1), 139.1 (2C, 4'''-$NCO_2CH_2Ph$, 4'''-$NCO_2CH_2PhC$-1), 128.9 (4'''-$NCO_2CH_2\overline{Ph}C$-3,5), 128.4 (4'''-$NCO_2CH_2PhC$-2,6), 127.1 (4'''-$NCO_2CH_2PhC$-4), 104.1 (C-1'), 97.9 (C-1''), 83.9 (C-9), 83.2 (C-6), 82.9 (C-5), 80.5 (C-3), 78.1 (C-4''), 77.3 (C-12), 75.9 (C-13), 74.8 (C-11), 72.3 (C-3''), 70.8 (C-2'), 68.9 (C-5'), 65.3 (2C, C-5'', C-3'), 60.1 (4'''-$NCO_2CH_2Ph$), 53.6 (2C,3'-N($CH_2CH_2)_2NZ$), 49.2 (3''-$OCH_3$), $\overline{46.7}$ (2C,C-2,3'-N($CH_2\overline{CH_2})_2NZ$), 41.7 (C-7), 36.6 (C-4), 35.2 (C-2''), 33.8 (C-10), $\overline{33.7}$ (C-8), 22.5 (13-$CH_2CH_3$), 22.3 (6-$CH_3$), 21.5 (3''-$CH_3$), 21.1 (5'-$CH_3$), 18.0 ($\overline{5}$''-$CH_3$), 17.6 (8-$CH_3$), 16.9 (12-$CH_3$), 16.1 (10-$CH_3$), 14.1 (2-$CH_3$), 12.0 (13-$CH_2\underline{C}H_3$), 9.6 (4-$CH_3$)

Example 64

Synthesis of de(3'-dimethylamino)-3'-piperazinyl-9-dihydro-pseudoerythromycin A 6,9-epoxide (EM966)

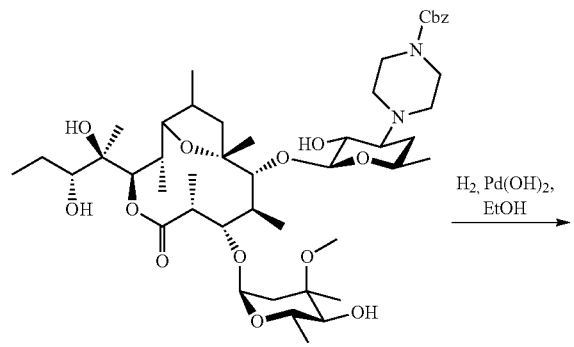

Under $N_2$ atmosphere, $Pd(OH)_2$ (24.2 mg) and EtOH (2.70 mL) were added to EM965 (122 mg, 0.137 mmol), and the mixture was stirred under $H_2$ atmosphere at room temperature for 4 hr. After stirring, the mixture was concentrated to give a crude product (150 mg). The obtained crude product was separated and purified by flash column chromatography ($CHCl_3$:MeOH:30% $NH_4OH$ aq=100:1:0.1-50:1:0.1) to give EM966 (54.2 mg, 52%) as a white powder.

IR (KBr) ν $cm^{-1}$; 3451, 2973, 2935, 2884, 2786, 1706, 1631, 1457, 1382, 1270, 1166, 1078, 1018

$^{13}C$ NMR (67.5 MHz, $CDCl_3$) δ (ppm): 177.3 (C-1), 103.3 (C-1'), 98.0 (C-1''), 83.9 (C-9), 83.2 (C-6), 82.6 (C-5), 80.4 (C-3), 78.1 (C-4''), 77.2 (C-12), 75.9 (C-13), 74.8 (C-11), 72.4 (C-3''), 68.6 (2C, C-2', C-5'), 65.4 (2C, C-5'', C-3'), 52.1 (2C, 3'-N($CH_2CH_2)_2NH$), 49.1 (3''-$OCH_3$), 46.6 (C-2), 41.8 (C-7), $\overline{40.6}$ (2C, 3'-N($CH_2\overline{CH_2})_2NH$), 36.4 (C-4), 35.2 (C-2''), 33.7 (C-10, C-8), $\overline{33.5}$ (C-4'), 22.5 (13-$CH_2CH_3$), 22.1 (6-$CH_3$), 21.5 (3''-$CH_3$), 20.8 (5'-$CH_3$), 18.1 ($\overline{5}$''-$CH_3$), 17.6 (8-$CH_3$), 17.0 (12-$CH_3$), 16.0 (10-$CH_3$), 13.9 (2-$CH_3$), 12.0 (13-$CH_2\underline{C}H_3$), 10.2 (4-$CH_3$)

Experimental Example 1

As one index of the anti-inflammatory action of the compound of the present invention, the differentiation induction-promoting activity of THP-1 cell was measured. The measurement was performed as shown below.

THP-1 cells (ATCC No. TIB-202) were adjusted to a concentration of $2 \times 10^5$ cells/ml with a medium (RPMI 1640), PMA was added thereto to a final concentration of 1-2 μM, and the mixture was dispensed to each well of a 96 well plate by 100 μl. A solution (100 μl) containing a test substance was adjusted to an appropriate concentration with the medium and added to each well. The mixture was stirred by gently shaking the plate, and incubated under 37° C., 5% $CO_2$ conditions for 72-96 hr. Each well was washed with PBS, a medium containing the viable cell measurement reagent SF (Nacalai Tesque) was added at 100 μl/well and the mixture was incubated under the conditions of 37° C., 5% $CO_2$ for 3-5 hr. The absorbance was measured with a plate reader.

The results of the THP-1 differentiation induction-promoting activity measured above are shown in Table 6. In the Table, the activity value is the lowest concentration necessary for the test compound to show a 50% activity value relative to the activity value of erythromycin A at 100 μM in this experiment.

TABLE 6

| compound No. (EM) | THP-1 differentiation induction-promoting activity |
|---|---|
| 900 | 30 |
| 901 | 30 |
| 902 | 30 |
| 903 | 30 |
| 904 | 10 |
| 905 | 3 |
| 906 | 30 |
| 907 | 30 |
| 908 | 10 |
| 909 | 30 |
| 910 | 100 |
| 911 | 10 |
| 913 | 30 |
| 914 | 100 |
| 917 | 30 |
| 918 | 30 |
| 925 | 30 |
| 932 | 10 |
| 935 | 30 |
| 936 | 10 |
| 939 | 3 |

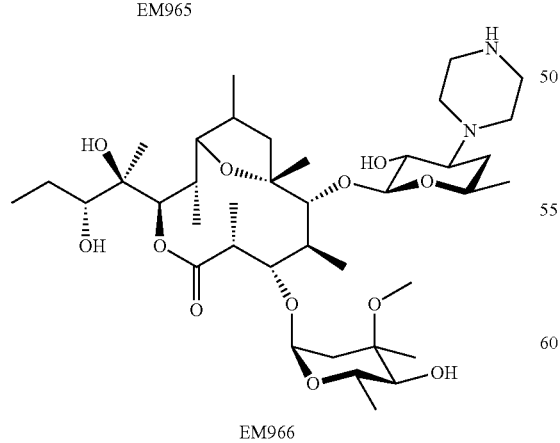

EM966

TABLE 6-continued

| compound No. (EM) | THP-1 differentiation induction-promoting activity |
|---|---|
| 946 | 100 |
| 947 | 10 |
| 949 | 10 |

THP-1 differentiation induction-promoting activity: The lowest concentration necessary for each compound to show 50% activity relative to the activity value of erythromycin A at 100 µM.

Experimental Example 2

As an index of the treatment effect of the compound of the present invention on ulcerative colitis and Crohn's disease, an action on trinitrobenzene sulfonate (hereinafter to be indicated as TNBS)-induced colitis was examined using rats.

Using 8-week-old male SD rats under pentobarbital anesthesia, TNBS solution was injected into the rectum of animals after fasting for 24 hr or longer and abstaining from water for 5 hr or longer. After injection, a silicone stopper was inserted into the anus to perform a treatment for 3.5-4 hr, whereby a colitis model was prepared. Two days after TNBS administration, model animals were selected based on the fecal occult blood score (fecal occult blood slide 5 shionogi II, Shionogi & Co. Ltd.), body weight and body weight changes, feeding condition, observation score of around anus and bleeding. A test drug was orally administered to the model animals two times a day for 6 days. On the next day of the final drug administration, the large intestine (about 15 cm from the anus) was removed after decapitation and exsanguination, and the level of damage was scored by the method of Wallace et al. (Wallace, J. L. et al, Inhibition of leukotriene synthesis markedly accelerates healing in a rat model of inflammatory bowel disease. Gastroenterology 96, 2936 (1989)), based on which the efficacy was evaluated.

The results are shown in Table 7. It was found that the compound of the present invention has an effect of improving TNBS-induced ulcer in the large intestine.

TABLE 7

| Test group | Dose (mg/kg)/day | n | Inflammation score in ulcer |
|---|---|---|---|
| Control (0.5% CMC-Na) | — | 15 | 4.27 ± 0.38 |
| EM905 | 10 × 2 | 14 | 3.29 ± 0.22 |
| EM905 | 30 × 2 | 15 | 2.67 ± 0.40* |
| EM914 | 10 × 2 | 15 | 2.93 ± 0.41 |
| EM914 | 30 × 2 | 13 | 2.69 ± 0.33* |

*$p < 0.05$

Experimental Example 3

The antibacterial activity of the compound of the present invention and erythromycin were measured according to the antibacterial sensitivity measurement method of the US National Committee for Clinical Laboratory Standards (NCCLS). The results are shown in Table 8. The values of minimum inhibitory concentration (MIC) (µg/ml) of each compound against bacteria are shown therein. It was found that the compound of the present invention does not have an antibacterial activity possessed by erythromycin.

TABLE 8

| | MIC (µg/ml) | | | | | |
|---|---|---|---|---|---|---|
| cell line/material | erythromycin | EM900 | EM901 | EM905 | EM914 | EM939 |
| S. aureus FDA209P 2002.1.31 | ≦0.5 | >128 | >128 | >128 | >128 | >64 |
| S. aureus Smith 2002.1.31 | ≦0.5 | >128 | >128 | >128 | >128 | >64 |
| S. aureus 8325 (pEP2104) | 64 | >128 | >128 | >128 | >128 | >64 |
| S. epidermidis IFO12648 2002.1.31 | ≦0.5 | >128 | >128 | >128 | — | >64 |
| M. luteus ATCC9341 2002.1.31 | ≦0.5 | 128 | >128 | >128 | — | >64 |
| E. faecalis ATCC21212 2002.1.31 | 1 | >128 | >128 | >128 | >128 | >64 |
| E. coli NIHJ JC-2 2002.1.31 | 64 | >128 | >128 | >128 | >128 | >64 |
| K. pneumoniae NCTN9632 2002.1.31 | 32 | >128 | >128 | >128 | >128 | >64 |
| S. marcescens IFO12648 2002.2.1 | 128 | >128 | >128 | >128 | >128 | >64 |
| E. aerogen NCTC10006 2002.2.1 | 128 | >128 | >128 | >128 | >128 | >64 |
| A. calcoaceticus IFO2552 2002.2.1 | 4 | >128 | >128 | >128 | >128 | >64 |

Formulation Example

The pharmaceutical composition of the present invention can be produced by a method conventionally used in the pertinent field and using additives for preparations. While a typical Formulation Example of the pharmaceutical agent of the present invention is shown in the following, the pharmaceutical composition of the present invention is not limited thereto.

(1) Tablet

In one tablet, each Example compound 1-500 mg

As additive, sodium citrate, cornstarch, povidone, carmellose sodium, cellulose acetate phthalate, propylene glycol, macrogol, sorbitan fatty acid ester and castor oil are contained.

(2) Ointment
In 1 g, each Example compound 10 mg (titer)
As additive, light liquid paraffin and white petrolatum are contained.
(3) Injection
Distilled water (10 ml) for injection is added to each Example compound (500 mg, titer) to give a 5% solution, which is diluted with glucose injection solution, physiological saline (for injection) and the like to give an intravenous drip infusion solution.

INDUSTRIAL APPLICABILITY

The present invention can provide a novel dihydropseudo-erythromycin derivative, which has superior anti-inflammatory action and is stable.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2005-301070 filed in Japan, the contents of which are incorporated in full herein by this reference.

The invention claimed is:
1. A compound represented by the following formula [I]

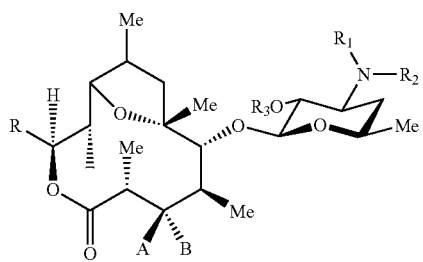

wherein Me is a methyl group,
$R_1$ and $R_2$ are the same or different and each is a hydrogen atom, an alkyl group, an acyl group, a sulfonyl group, a substituted or unsubstituted aryl-substituted alkyl group, an aryl-substituted alkyloxycarbonyl group, an alkenyl group or an alkynyl group, or $R_1$ and $R_2$ in combination form, together with the adjacent nitrogen atom, a substituted or unsubstituted alicyclic heterocyclic group,
$R_3$ is a hydrogen atom, a substituted or unsubstituted acyl group or an aryl-substituted alkyloxycarbonyl group,
A is a hydrogen atom, B is a hydroxyl group or a group represented by the following formula [II]

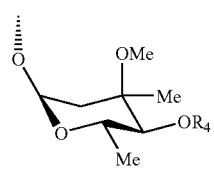

wherein Me is a methyl group and $R_4$ is a hydrogen atom or an acyl group, or A and B in combination show =O,
R is a group represented by the following formula [III]

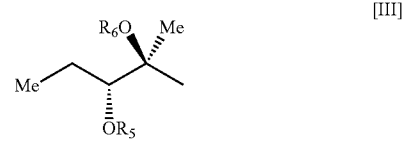

wherein Me is a methyl group, $R_5$ and $R_6$ are the same or different and each is a hydrogen atom or an acyl group, or $R_5$ and $R_6$ in combination show a carbonyl group or a substituted or unsubstituted alkylene group, a substituent represented by the following formula [IV]

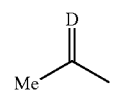

wherein Me is a methyl group, D is O or N—OH, or D is a hydrogen atom and a hydroxyl group (—H, —OH), or a substituent represented by the following formula [V]

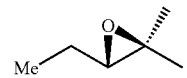

wherein Me is a methyl group, or a pharmacologically acceptable salt thereof.

2. The compound of claim 1, wherein R is a group represented by the following formula [III]

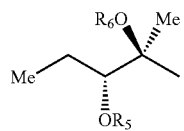

wherein Me is a methyl group, $R_5$ and $R_6$ are the same or different and each is a hydrogen atom or an acyl group, or $R_5$ and $R_6$ in combination show a carbonyl group or a substituted or unsubstituted alkylene group, or a pharmacologically acceptable salt thereof.

3. The compound of claim 1, wherein A and B in combination show =O, or a pharmacologically acceptable salt thereof.

4. The compound of claim 1, wherein A is a hydrogen atom and B is a hydroxyl group, or a pharmacologically acceptable salt thereof.

5. The compound of claim 1, wherein A is a hydrogen atom and B is a group represented by the following formula [II]

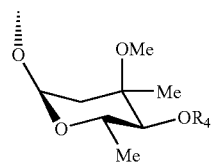

wherein Me is a methyl group and $R_4$ is a hydrogen atom or an acyl group, or a pharmacologically acceptable salt thereof.

6. The compound of claim 5, wherein $R_4$ is a hydrogen atom, or a pharmacologically acceptable salt thereof.

7. The compound of claim 1, wherein $R_1$ and $R_2$ are the same or different and each is a hydrogen atom, an alkyl group, a substituted or unsubstituted benzyl group or a benzyloxycarbonyl group, or $R_1$ and $R_2$ in combination form, together with the adjacent nitrogen atom, a substituted or unsubstituted alicyclic heterocyclic group, or a pharmacologically acceptable salt thereof.

8. The compound of claim 1, wherein $R_1$ and $R_2$ are the same or different and each is a hydrogen atom, a lower alkyl group having 1 to 3 carbon atoms or a halogen-substituted benzyl group, or a pharmacologically acceptable salt thereof.

9. The compound of claim 1, wherein the substituted or unsubstituted alicyclic heterocyclic group formed by $R_1$ and $R_2$ in combination together with the adjacent nitrogen atom is a substituted or unsubstituted morpholine ring, piperidine ring, piperazine ring or pyrrolidine ring, or a pharmacologically acceptable salt thereof.

10. The compound of claim 1, wherein $R_3$ is a hydrogen atom, an acetyl group, a substituted or unsubstituted benzoyl group or a benzyloxycarbonyl group, or a pharmacologically acceptable salt thereof.

11. The compound of claim 1, wherein $R_3$ is a hydrogen atom, a substituted or unsubstituted acetyl group or a benzoyl group, or a pharmacologically acceptable salt thereof.

12. The following compound
(1) 9-dihydro-pseudoerythromycin A 6,9-epoxide
(2) de(3'-N-methyl)-9-dihydro-pseudoerythromycin A 6,9-epoxide
(3) de(3'-N-methyl)-3'-N-benzyl-9-dihydro-pseudoerythromycin A 6,9-epoxide
(4) bis-de(3'-N-methyl)-9-dihydro-pseudoerythromycin A 6,9-epoxide
(5) bis-de(3'-N-methyl)-bis-(3'-N-benzyl)-9-dihydro-pseudoerythromycin A 6,9-epoxide
(6) de(3'-N-methyl)-3'-N-(p-chlorobenzyl)-9-dihydro-pseudoerythromycin A 6,9-epoxide
(7) de[12-(1-hydroxypropyl)]-9-dihydro-12-oxo-pseudoerythromycin A 6,9-epoxide
(8) de[12-(1-hydroxypropyl)]-9-dihydro-12-hydroxyoxime-pseudoerythromycin A 6,9-epoxide
(9) de[12-(1-hydroxypropyl)]-9-dihydro-pseudoerythromycin A 6,9-epoxide
(10) 12,13-epoxy-9-dihydro-pseudoerythromycin A 6,9-epoxide
(11) de(3-O-cladinosyl)-9-dihydro-pseudoerythromycin A 6,9-epoxide
(12) 4'',13-O-diacetyl-9-dihydro-pseudoerythromycin A 6,9-epoxide
(13) 2'-O-acetyl-9-dihydro-pseudoerythromycin A 6,9-epoxide
(14) de(3'-dimethylamino)-3'-morpholino-9-dihydro-pseudoerythromycin A 6,9-epoxide
(15) 2'-O-acetyl-de(3-O-cladinosyl)-9-dihydro-3-keto-pseudoerythromycin A 6,9-epoxide 12,13-carbonate
(16) de(3-O-cladinosyl)-9-dihydro-3-keto-pseudoerythromycin A 6,9-epoxide 12,13-carbonate
(17) de(3'-N-methyl)-3'-N-(p-chlorobenzyl)-de(3-O-cladinosyl)-9-dihydro-pseudoerythromycin A 6,9-epoxide
(18) 2'-O-acetyl-de(3-O-cladinosyl)-9-dihydro-3-keto-de(3'-dimethylamino)-3'-morpholino-pseudoerythromycin A 6,9-epoxide 12,13-carbonate
(19) de(3-O-cladinosyl)-9-dihydro-3-keto-de(3'-dimethylamino)-3'-morpholino-pseudoerythromycin A 6,9-epoxide 12,13-carbonate
(20) de(3'-N-methyl)-2'-O-3'-N-bis(benzyloxycarbonyl)-de(3-O-cladinosyl)-9-dihydro-pseudoerythromycin A 6,9-epoxide 12,13-carbonate
(21) de(3'-N-methyl)-3'-N-(p-chlorobenzyl)-de(3-O-cladinosyl)-9-dihydro-3-keto-pseudoerythromycin A 6,9-epoxide 12,13-carbonate
(22) de(3-O-cladinosyl)-9-dihydro-de(3'-dimethylamino)-3'-morpholino-pseudoerythromycin A 6,9-epoxide 12,13-carbonate
(23) de(3'-N-methyl)-3'-N-(p-chlorobenzyl)-de(3-O-cladinosyl)-9-dihydro-3-keto-pseudoerythromycin A 6,9-epoxide 12,13-isopropylidene acetal or
(24) de(3'-N-methyl)-3'-N-(p-chlorobenzyl)-de(3-O-cladinosyl)-9-dihydro-3-keto-pseudoerythromycin A 6,9-epoxide,
or a pharmacologically acceptable salt thereof.

13. The following compound
(1) 9-dihydro-pseudoerythromycin A 6,9-epoxide
(2) de(3'-N-methyl)-3'-N-(p-chlorobenzyl)-9-dihydro-pseudoerythromycin A 6,9-epoxide
(3) de(3'-dimethylamino)-3'-morpholino-9-dihydro-pseudoerythromycin A 6,9-epoxide or
(4) de(3'-N-methyl)-3'-N-(p-chlorobenzyl)-de (3-O-cladinosyl)-9-dihydro-3-keto-pseudoerythromycin A 6,9-epoxide 12,13-carbonate,
or a pharmacologically acceptable salt thereof.

14. A pharmaceutical composition comprising a compound of claim 1 or a pharmacologically acceptable salt thereof as an active ingredient.

15. A method for the treatment of an inflammatory disease, which comprises administering an effective amount of a compound of claim 1 or a pharmacologically acceptable salt thereof to a patient in need thereof.

16. The method of claim 15, wherein the inflammatory disease is an inflammatory bowel disease.

17. A commercial package comprising an agent for the treatment of an inflammatory disease, which comprises a compound of claim 1 or a pharmacologically acceptable salt thereof as an active ingredient, and a written matter stating that the agent can or should be used for the treatment of an inflammatory disease.

18. A pharmaceutical composition comprising a compound of claim 12 or a pharmacologically acceptable salt thereof as an active ingredient.

19. A pharmaceutical composition comprising a compound of claim 13 or a pharmacologically acceptable salt thereof as an active ingredient.

20. A method for the treatment of an inflammatory disease, which comprises administering an effective amount of a compound of claim 12 or a pharmacologically acceptable salt thereof to a patient in need thereof.

21. A method for the treatment of an inflammatory disease, which comprises administering an effective amount of a compound of claim 13 or a pharmacologically acceptable salt thereof to a patient in need thereof.

22. The method of claim 20, wherein the inflammatory disease is an inflammatory bowel disease.

23. The method of claim 21, wherein the inflammatory disease is an inflammatory bowel disease.

24. A commercial package comprising an agent for the treatment of an inflammatory disease, which comprises a compound of claim 12 or a pharmacologically acceptable salt thereof as an active ingredient, and a written matter stating that the agent can or should be used for the treatment of an inflammatory disease.

25. A commercial package comprising an agent for the treatment of an inflammatory disease, which comprises a compound of claim 13 or a pharmacologically acceptable salt thereof as an active ingredient, and a written matter stating that the agent can or should be used for the treatment of an inflammatory disease.

* * * * *